United States Patent
Winter et al.

(10) Patent No.: US 9,657,288 B2
(45) Date of Patent: *May 23, 2017

(54) CONNECTOR COMPOUND PEPTIDE PHAGE DISPLAY

(71) Applicant: BICYCLE THERAPEUTICS LIMITED, Cambridge (GB)

(72) Inventors: Gregory P. Winter, Cambridge (GB); Christian Heinis, Bern (CH)

(73) Assignee: BICYCLE THERAPEUTICS LIMITED, Cambridge (GB)

(*) Notice: Subject to any disclaimer, the term of this patent is extended or adjusted under 35 U.S.C. 154(b) by 561 days.

This patent is subject to a terminal disclaimer.

(21) Appl. No.: 13/973,297

(22) Filed: Aug. 22, 2013

(65) Prior Publication Data
US 2014/0187757 A1    Jul. 3, 2014

Related U.S. Application Data

(62) Division of application No. 12/866,214, filed as application No. PCT/GB2009/000301 on Feb. 4, 2009, now Pat. No. 8,680,022.

(30) Foreign Application Priority Data

Feb. 5, 2008 (GB) .................................. 0802079.4
Oct. 8, 2008 (GB) .................................. 0818399.8

(51) Int. Cl.
C40B 50/06 (2006.01)
C12N 15/10 (2006.01)
A61K 47/48 (2006.01)
C07K 1/107 (2006.01)
C40B 40/08 (2006.01)
(Continued)

(52) U.S. Cl.
CPC ........ *C12N 15/1062* (2013.01); *A61K 47/481* (2013.01); *A61K 47/48023* (2013.01); *A61K 47/48246* (2013.01); *C07K 1/1075* (2013.01); *C07K 1/1077* (2013.01); *C07K 14/005* (2013.01); *C12N 15/1037* (2013.01); *C12N 15/1041* (2013.01); *C12N 15/1068* (2013.01);
(Continued)

(58) Field of Classification Search
None
See application file for complete search history.

(56) References Cited

FOREIGN PATENT DOCUMENTS

| WO | WO 95/01438 | 1/1995 | |
|---|---|---|---|
| WO | WO 01/23619 A1 * | 4/2001 | .............. C12Q 1/68 |
| WO | WO 2008/013454 | 1/2008 | |

OTHER PUBLICATIONS

Millward et al. (Sep. 21, 2007) ACS Chemical Biology vol. 2 pp. 625 to 634.*

(Continued)

*Primary Examiner* — Christian Boesen
(74) *Attorney, Agent, or Firm* — Convergent Law Group LLP

(57) ABSTRACT

The invention relates to a complex comprising a phage particle, said phage particle comprising
(i) a polypeptide;
(ii) a nucleic acid encoding the polypeptide of (i);
(iii) a connector compound attached to said polypeptide wherein said connector compound is attached to the polypeptide by at least three discrete covalent bonds. The invention also relates to libraries, and to methods for making complexes and to methods of screening using same.

7 Claims, 20 Drawing Sheets

(51) Int. Cl.
*G01N 33/569* (2006.01)
*C07K 14/005* (2006.01)

(52) U.S. Cl.
CPC .............. *C40B 40/08* (2013.01); *C40B 50/06* (2013.01); *G01N 33/56983* (2013.01)

(56) References Cited

OTHER PUBLICATIONS

Smith et al. (2007) March's Advanced Organic Chemistry John Wiley and Sons Hoboken New Jersey pp. 478 to 483.*
Marsault et al. (Nov. 7, 2006) Journal of Medicinal Chemistry vol. 49 pp. 7190 to 7197.*
Marsault et al. (Nov. 7, 2006) Journal of Medicinal Chemistry vol. 49 pp. 7190 to 7197 supporting information.*
Timmerman et al. (Apr. 5, 2005) ChemBioChem vol. 6 pp. 821 to 824.*
Timmerman et al. (Apr. 5, 2005) ChemBioChem vol. 6 pp. 821 to 824 supporting information.*
Heinis et al. (May 31, 2009) Nature Chemical Biology vol. 5 pp. 502 to 507.*
Heinis et al. (May 31, 2009) Nature Chemical Biology vol. 5 pp. 502 to 507 Supplementary information.*
Kather et al. (Oct. 19, 2005) Journal of Molecular Biology vol. 354 pp. 666 to 678.*
Japanese Examination Report dated Oct. 1, 2013, for Japanese Patent Application No. 2010-545546, a Japanese counterpart of U.S. Appl. No. 13/973,297, pp. 1-3 of the Japanese language document, pp. 1-3 of the English translation.

* cited by examiner

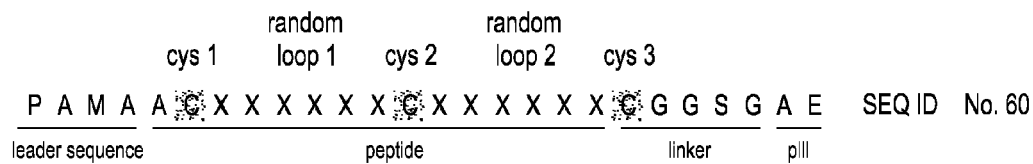

```
                 random        random
         cys 1   loop 1  cys 2 loop 2  cys 3
P A M A  A C X X X X X X C X X X X X X C G G S G A E   SEQ ID No. 60
leader sequence        peptide              linker  pIII
```

FIG. 3A

| Mutant: | Amino acid sequence: | IC$_{50}$(nM): | SEQ ID No.: |
|---|---|---|---|
| PK1 | A C D S R F R N C P W S M S G C G | 1500 | 36 |
| PK2 | A C S D R F R N C P L W S G T C G | 400 | 1 |
| PK3 | A C R D I R F R C N Y D V A V C G |  | 37 |
| PK4 | A C S T E R R Y C P I E I F P C G | 400 | 2 |
| PK5 | A C A P W R T M C L N I D G P C G |  | 38 |
| PK6 | A C A P W R T A C Y E D L M N C G | 500 | 3 |
| PK7 | A C P V W R T L C M E S E G V C G |  | 39 |
| PK8 | A C F P L W R T C V H E P P M C G |  | 40 |
| PK9 | A C W Q V Q V N C R V N F G K C G | 800 | 41 |
| PK10 | A C G G N S D R C R V N N I S C G | 2000 | 42 |
| PK11 | A C G R G D Q T C R V N W H P C G |  | 43 |
| PK12 | A C - - V H N Y C R V N W V T C G | 1800 | 44 |
| PK13 | A C G T G E G R C R V N W T P C G | 500 | 4 |

FIG. 3B

| Mutant: | Amino acid sequence: | IC$_{50}$(nM): | SEQ ID No.: |
|---|---|---|---|
| CG1 | A C E F G D L W C G W D P P V C G |  | 45 |
| CG2 | A C E F D V G F C W D G F G Q C G | 100 | 46 |
| CG3 | A C E F D A G F C Q Q H S T E C G |  | 47 |
| CG4 | A C W F D L G F C H N D W W N C G | 100 | 9 |
| CG5 | A C E F D L G F C G G G E G P C G | 150 | 48 |
| CG6 | A C P R I E G F C L P I F S D C G | 1000 | 49 |
| CG7 | A C L R A Q E D C V Y D R G F C G | 200 | 10 |
| CG8 | A C T R G S G D C T Y D F G F C G | 200 | 50 |

FIG. 3C

Library 2                                                     SEQ ID No. 61

P A M A A C S D R F R N C X X X X X X C G G S G A E

Library 3                                                     SEQ ID No. 62

P A M A A C A P W R T A C X X X X X X C G G S G A E

Library 4                                                     SEQ ID No. 63

P A M A A C X X X X X X C R V N W T P C G G S G A E
─────────────────────   ──────────────────────────   ─────────  ───
  leader sequence                peptide              linker   pIII

FIG. 4A

| Mutant: | Amino acid sequence: | IC$_{50}$ (nM): | SEQ ID No.: |
|---|---|---|---|
| PK14 | A C S D R F R N C P A D E R E C G |    | 51 |
| PK15 | A C S D R F R N C P A D E A L C G | 20 | 5  |
| PK16 | A C S D R F R N C P V D E A L C G | 20 | 52 |
| PK17 | A C S D R F R N C P V D E W L C G | 30 | 53 |
| PK18 | A C S D R F R N C P G D E S L C G |    | 54 |
| PK19 | A C S D R F R N C P Y T L H D C G | 30 | 55 |
| PK20 | A C S D R F R N C P Y V S S D C G |    | 56 |
| PK21 | A C S D R F R N C P Y S E G D C G |    | 57 |
| PK22 | A C S D R F R N C P V W D S S C G |    | 58 |
| PK23 | A C S D R F R N C P V S E S A C G | 50 | 59 |

FIG. 4B

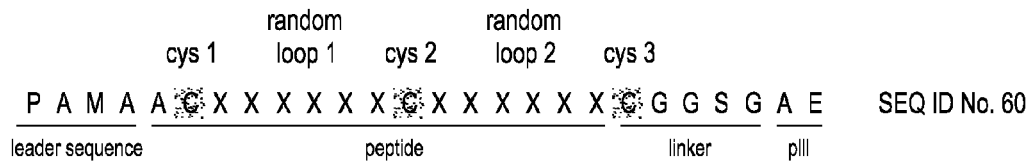

FIG. 11A

| Mutant: | Amino acid sequence: | IC₅₀ (nM): | SEQ ID No.: |
|---|---|---|---|
| PK1 | A C D S R F R N C P W S M S G C G | 1500 | 36 |
| PK2 | A C S D R F R N C P L W S G T C G | 400 | 1 |
| PK3 | A C R D I R F R C N Y D V A V C G |  | 37 |
| PK4 | A C S T E R R Y C P I E I F P C G | 400 | 2 |
| PK5 | A C A P W R T M C L N I D G P C G |  | 38 |
| PK6 | A C A P W R T A C Y E D L M N C G | 500 | 3 |
| PK7 | A C P V W R T L C M E S E G V C G |  | 39 |
| PK8 | A C F P L W R T C V H E P P M C G |  | 40 |
| PK9 | A C W Q V Q N C R V N F G K C G | 800 | 41 |
| PK10 | A C G G N S D R C R V N N I S C G | 2000 | 42 |
| PK11 | A C G R G D Q T C R V N W H P C G |  | 43 |
| PK12 | A C - - V H N Y C R V N W V T C G | 1800 | 44 |
| PK13 | A C G T G E G R C R V N W T P C G | 500 | 4 |

FIG. 11B

| Mutant: | Amino acid sequence: | IC₅₀ (nM): | SEQ ID No.: |
|---|---|---|---|
| CG1 | A C E Y G D L W C G W D P P V C G |  | 45 |
| CG2 | A C E Y D V G F C W D G F G Q C G | 100 | 46 |
| CG3 | A C F D A G F C Q Q H S T E C G |  | 47 |
| CG4 | A C V F D L G F C H N D W W N C G | 100 | 9 |
| CG5 | A C F D L G F C G G G E G P C G | 150 | 48 |
| CG6 | A C P R I E G F C L P I F S D C G | 1000 | 49 |
| CG7 | A C L R A Q E D C V Y D R G F C G | 200 | 10 |
| CG8 | A C T R G S G D C T Y D F G F C G | 200 | 50 |

FIG. 11C

Library 2                                               SEQ ID No. 61

P A M A A C S D R F R N C X X X X X X C G G S G A E

Library 3                                               SEQ ID No. 62

P A M A A C A P W R T A C X X X X X X C G G S G A E

Library 4                                               SEQ ID No. 63

P A M A A C X X X X X X C R V N W T P C G G S G A E leader sequence           peptide              linker    pIII

FIG. 12A

| Mutant: | Amino acid sequence: | IC$_{50}$(nM): | SEQ ID No.: |
|---|---|---|---|
| PK14 | A C S D R F R N C P A D E R E C G |  | 51 |
| PK15 | A C S D R F R N C P A D E A L C G | 20 | 5 |
| PK16 | A C S D R F R N C P V D E A L C G | 20 | 52 |
| PK17 | A C S D R F R N C P V D E W L C G | 30 | 53 |
| PK18 | A C S D R F R N C P G D E S L C G |  | 54 |
| PK19 | A C S D R F R N C P Y T L H D C G | 30 | 55 |
| PK20 | A C S D R F R N C P Y V S S D C G |  | 56 |
| PK21 | A C S D R F R N C P Y S E G D C G |  | 57 |
| PK22 | A C S D R F R N C P V W D S S C G |  | 58 |
| PK23 | A C S D R F R N C P V S E S A C G | 50 | 59 |

FIG. 12B

CONNECTOR COMPOUND PEPTIDE PHAGE DISPLAY

CROSS REFERENCE TO RELATED APPLICATIONS

This application is a continuation application of U.S. Ser. No. 12/866,214, filed 8 Aug. 2010, which is a 371(c)(1) filing of PCT/GB09/00301 filed 9 Feb. 2009; which claims priority to GB0802079.4, filed 5 Feb. 2008 and GB0818399.8, filed 8 Oct. 2008.

METHODS AND COMPOSITIONS

Field of the Invention

The invention relates to the modification and constraint of polypeptides, in particular to genetically encoded polypeptides in complexes with nucleic acid encoding them such as in the context of phage display.

Background to the Invention

The generation of molecules with high affinity and specificity for biological targets is a central problem in chemistry, biology and pharmaceutical sciences. In particular, binding ligands are important for the creation of drugs that can intervene with biological processes. The creation of ligands that bind to a chosen target ligand usually involves a process of generating a plurality of putative binding molecules and testing said molecules for their binding properties.

While biological in vitro selection techniques were used efficiently for the isolation of large biopolymeric structures such as antibodies, they were less practicable for the isolation of small molecule drugs to date. Biological in vitro selection techniques are generally limited to biological polymers such as polypeptides, RNA or DNA. Short biopolymers as for example peptides can also bind to biological targets but they can suffer from conformational flexibility and may be prone to proteolytic degradation in bodily fluids. In addition, binding affinities of short linear peptides are often weak. Various circularization strategies are known to constrain genetically encoded small peptide libraries. Phage displayed peptide repertoires are known for example to be circularized by the oxidation of two flanking cysteine residues. mRNA encoded cyclic peptide libraries are known to be generated by linking the N-terminal amine and a lysine residue of the peptide with a chemical cross-linking reagent. This strategy was used for the isolation of redox-insensitive macrocycles that bind to the signaling protein Gαi1 (Millward, S. W. et al., ACS Chem. Biol., 2007). Various strategies are also known for use to incorporate non-natural building blocks into genetically encoded polypeptide libraries to expand the diversity of the libraries or to insert properties that can not be provided by natural amino acids. However, the strategies allowed only the addition of a limited number of small organic appendages to linear genetically encoded polypeptides. Frankel, A. et al., for example had incorporated non-natural amino acids into natural polypeptides that were encoded by mRNA display (Frankel, A. et al., Chem. Biol., 2003). Jespers L. et al. had chemically linked a fluorescent reporter molecule to a hypervariable loop of an antibody repertoire displayed on phage, and selected this repertoire for antigen binding (Jespers, L., et al., Prot. Eng., 2004). Dwyer, M. A. et al. had joined synthetic peptides to a repertoire of phage displayed peptides by native chemical ligation for the generation of a protease inhibitor library containing a non-natural amino acid (Dwyer, M. A. et al., Chemistry & Biology, 2000). Small organic molecules have also been linked to mRNA encoded combinatorial peptide repertoires. The research team of Roberts, R. W. had attached a penicillin moiety to a fixed position of an mRNA-display peptide library to select inhibitors of the *Staphylococcus aureus* penicillin binding protein 2a (Li, S. and Roberts, W. R., Chem. & Biol., 2003).

In order to apply in vitro selection to combinatorial compound libraries having more diverse molecule architectures (e.g. branched molecules) and being formed of non-natural building blocks, various methodologies have been proposed. Unlike biological in vitro selection methods, these methodologies use chemical strategies to attach DNA tags to small organic molecules. Brenner S. and Lerner R. A. had proposed a process of parallel combinatorial synthesis to encode individual members of a large library of chemicals with unique nucleotide sequences on beads (Brenner, S. and Lerner, R. A., PNAS, 1992). After the chemical entity is bound to the target, the genetic code is decoded by sequencing of the nucleotide tag. Liu D. R. and co-workers had conjugated a small collection of organic molecules to DNA oligonucleotides and performed affinity selections with different antigens (Doyon, J. B. et al., JACS, 2003). Neri D. and co-workers had generated large repertoires of molecule pairs by self-assembly of smaller DNA encoded chemical sub-libraries through hybridization of two DNA strands (Melkko, S. et al., Nature Biotechnol., 2004). The methodology was successfully used for affinity maturation of small molecule ligands. Halpin D. R. and Harris P. B. developed a strategy for the in vitro evolution of combinatorial chemical libraries that involves amplification of selected compounds to perform multiple selection rounds (Halpin, D. R. and Harbury, P. B., PLOS Biology, 2004). Woiwode T. F. et al. attached libraries of synthetic compounds to coat proteins of bacteriophage particles such that the identity of the chemical structure is specified in the genome of the phage (Woiwode, T. F., Chem. & Biol., 2003). All these strategies employing DNA specified chemical compounds have proven to be efficient in model experiments and some have even yielded novel small molecule binders. However, it became apparent that the encoding of large compound libraries and the amplification of selected compounds is much more demanding than the equivalent procedures in biological selection systems.

Jespers et al (2004 Protein engineering design and selection, volume 17, no. 10, pages 709-713) describes the selection of optical biosensors from chemisynthetic antibody libraries. This document is concerned with the attachment of a fluorescent reporter molecule through the hypervariable loop of an antibody repertoire displayed on the phage. In particular, this document describes linking of a fluorescent reporter molecule into a hypervariable loop (complementarity determining region or CDR) of a synthetic antibody repertoire. The fluorescent reporter molecule is linked by a single covalent bond to an artificially introduced cysteine residue in the hypervariable loop. A one to one attachment is performed. The cysteine residues on the phage particles were reduced with DTT and the excess reducing agent was removed by conventional polyethylene glycol (PEG) precipitation as is well known in the art.

Dwyer et al disclose biosynthetic phage display, describing a novel protein engineering tool combining chemical and genetic diversity. Dwyer et al (Chem Biol 2000, volume 7, no. 4, pages 263-274) describe the chemical ligation of a synthetic peptide having a non-natural amino acid onto a library of synthetic peptides comprising the main structural residues of a protein of interest. The motivation for performing this was in order to generate a diverse range of protease sequences, each having a constant segment incorporating an unnatural amino acid. The synthetic peptide comprising the non-natural amino acid was simply joined by native chemical ligation, resulting in coupling of the two peptide fragments together. No connector compound is disclosed. No small molecule attachment is disclosed. No constraint or conformational restriction of the resulting polypeptide was achieved. No covalent bonding of particular moieties to the polypeptide chain is disclosed.

Different research teams have previously tethered polypeptides with cysteine residues to a synthetic molecular structure (Kemp, D. S. and McNamara, P. E., J. Org. Chem., 1985; Timmerman, P. et al., ChemBioChem, 2005). Meloen and co-workers had used tris(bromomethyl)benzene and related molecules for rapid and quantitative cyclisation of multiple peptide loops onto synthetic scaffolds for structural mimicry of protein surfaces (Timmerman, P. et al., ChemBioChem, 2005). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Methods provided in WO 2004/077062 and WO 2006/078161, are based on sampling individual compounds for example in a screening procedure. Screening of individual compounds or small sets of compounds is tedious and can be expensive if large numbers of compounds are analyzed. The number of compounds that can be assayed with screening assays generally does not exceed several thousands. Moreover, reaction conditions described in WO 2004/077062 to tether a cysteine containing peptide to a halomethyl containing scaffold as for example tris(bromomethyl)benzene are not suitable to modify a genetically encoded cysteine containing peptide.

WO2004/077062 discloses a method of selecting a candidate drug compound. In particular, this document discloses various scaffold molecules comprising first and second reactive groups, and contacting said scaffold with a further molecule to form at least two linkages between the scaffold and the further molecule in a coupling reaction. This method suffers from many restrictions. Firstly, it is based on the use of synthetic peptides and in vitro chemical reactions in separate vessels. For this reason, it is labour intensive. There is no opportunity to automate or to apply the method to the screening of many peptide variants without manually producing each variant by conducting numerous parallel independent reactions. There is no mention of genetically encoded diversity in this document, and certainly no mention of application to genetically encoded phage libraries. Indeed, the reaction conditions disclosed in this document mean that it would be difficult or impossible to perform the reactions disclosed on phage particles.

WO2006/078161 discloses binding compounds, immunogenic compounds and peptidomimetics. This document discloses the artificial synthesis of various collections of peptides taken from existing proteins. These peptides are then combined with a constant synthetic peptide having some amino acid changes introduced in order to produce combinatorial libraries. By introducing this diversity via the chemical linkage to separate peptides featuring various amino acid changes, an increased opportunity to find the desired binding activity is provided. FIG. 7 of this document shows a schematic representation of the synthesis of various loop peptide constructs. There is no disclosure of genetically encoded peptide libraries in this document. There is no disclosure of the use of phage display techniques in this document. This document discloses a process which is considered to be incompatible with phage display. For example, the chemistry set out in this document is likely to result in the linking molecule reacting with the phage coat. There is a risk that it could cross link phage particles. It is probable that phage particles would be inactivated (e.g. would lose their infectivity) if subjected to the chemistry described. This document is focussed on the manipulation of various synthetic peptides in independent chemical conjugation reactions.

Millward et al (2007 Chemical Biology, volume 2, no. 9, pages 625-634) disclose the design of cyclic peptides that bind protein surfaces with antibody like affinity. This document discloses cyclisation of various peptides produced from a genetically encoded library. The polypeptides are cyclised through reaction of a chemical cross-linker with the N-terminal amine and an amine of a lysine in the polypeptide. In this document, the genetically encoded library is a mRNA display library. This document does not disclose the attachment of any connector compound to the resulting polypeptides. This document is concerned with the production of redox insensitive cyclised peptides. The chemistry disclosed in this document is cyclisation through reaction of a chemical cross linker with the N-terminal amine and an amine of a lysine provided in the polypeptide. The cyclisation reaction is performed in a 50 milimolar phosphate buffer at pH 8 by the addition of DSG (1 mg per ml in DMF). At most, this document discloses the bridging of two parts of a polypeptide chain via a cross linking moiety in order to provide a cyclic peptide.

US2003/0235852 discloses nucleic acid-peptide display libraries containing peptides with unnatural amino acid residues, and methods of making these using peptide modifying agents. In other words, this document discloses genetically encoded polypeptide libraries that contain either a non-natural amino acid or an amino acid where a non-natural building block (e.g. penicillin) is post-translationally attached in a chemical reaction. This document is focused on known methods for associating a translated peptide with the nucleic acid which encoded it. The further problem addressed by this document is how to incorporate unnatural amino acids into that peptide. This is principally accomplished by the use of suppressor tRNAs in order to incorporate unnatural amino acids in response to amber/ochre/opal codons as is well known in the art. In other more minor embodiments, unnatural amino acids are created post-translationally by treatment of the translated peptide with a 'peptide modifying agent'. This reagent is typically aimed at altering an existing amino acid residue in order to convert it into an unnatural amino acid residue, or otherwise render it functionally reactive or receptive to the attachment of a further chemical moiety. Specifically, this document teaches the post-translational conjugation of a cysteine residue in the polypeptide of interest to the beta lactam antibiotic 6-bromoacetyl penicilamic acid. This results in the conjugation of this penicillin analogue onto the polypeptide of interest via a single bond to the cysteine residue side chain. No multiple bonding of the molecule being ligated to the polypeptide is disclosed. No conformational constraint of the polypeptide is described. No peptide loops or any other complex tertiary structures are formed by the methods disclosed in this document—it is purely a way of attaching a single further molecular group to a polypeptide via a single bond. Conventional conjugation chemistry is used in order to perform the modifications to the polypeptides in this document.

SUMMARY OF THE INVENTION

The present invention advantageously allows the combination of genetically encoded diversity, in particular genetically encoded polypeptide libraries, with chemical modification and conformational constraint.

Moreover, the techniques disclosed herein provide for the first time the linking of a connector compound to a polypeptide molecule by at least three covalent bonds. This provides the advantage of conformational constraint of the polypeptide, in particular conformational constraint of at least two segments of the polypeptide with respect to each other. By contrast, cross-linking techniques of the prior art, or the use of a connector which makes only two covalent bonds, will constrain only a single segment of the polypeptide.

Advantages of the invention flow from these technical features, for example due to their triple-bonded construction, the conjugated molecules of the invention have two or more peptide loops that can interact with a target. With multiple binding loops, higher binding affinities can be obtained than with molecules that have just a single peptide loop.

In addition, the interaction surface of a molecule of the invention with two or more binding loops for interaction with a target is larger than the one of a molecule with a single peptide loop with a target. The larger binding surface can provide improved binding affinity, and/or can also provide improved specificity.

Thus in one aspect the invention provides a complex comprising
(i) a polypeptide;
(ii) a nucleic acid encoding the polypeptide of (i);
(iii) a connector compound attached to said polypeptide wherein said connector compound is attached to the polypeptide by at least three discrete covalent bonds.

More in particular the invention provides a complex comprising a phage particle, said phage particle comprising
(i) a polypeptide;
(ii) a nucleic acid encoding the polypeptide of (i);
(iii) a connector compound attached to said polypeptide wherein said connector compound is attached to the polypeptide by at least three discrete covalent bonds.

The covalent bonds are suitably discrete covalent bonds in the sense of each being a separate bond between the connector compound and a part of the polypeptide. For example, a single bridge between the polypeptide and the connector compound which single bridge is made up of three covalent bonds (e.g. connector -x-y-polypeptide where "-" represents a covalent bond) would not be considered to comprise at least three discrete covalent bonds because the three bonds are not three separate bridges or connections from the connector compound to the target polypeptide. The underlying principle is that the connector compound/molecular core and the polypeptide are joined by at least three separate covalent bridging bonds.

Suitably each of the at least three covalent bonds is formed with a separate amino acid residue of the polypeptide. In other words, a separate amino acid residue is suitably an individual or distinct amino acid residue—more than one bond may be formed with a single species or type of amino acid residue e.g. two of the bonds may each be formed with cysteine residues but suitably those two cysteine residues will be separate cysteine residues.

The connector compound-polypeptide part of the complex described above is sometimes referred to as the 'conjugate'. In some embodiments the conjugate (i.e. a polypeptide-connector compound moiety corresponding to that comprised by the complex of the invention) may be separately synthesised. In this embodiment the conjugate may not be complexed with a nucleic acid. This is discussed in more detail below.

Suitably 'encoding' has its natural meaning in the art, i.e. encoding in the sense of the universal triplet code to convert nucleotide sequence into polypeptide sequence. In the prior art, 'encoding' might have been used in the sense of 'tagging' or 'deconvoluting' e.g. when a unique nucleotide sequence is used to tag a moiety and that knowledge of the nucleotide sequence can 'decode' i.e. tell the user which tagged moiety was present, yet without bearing any biological relationship to its structure. However, in the present invention, 'encode' and 'decode' are used in the traditional natural manner to refer to encoding in the sense of translation from nucleotide sequence to amino acid sequence.

Suitably the connector compound comprises an organic molecule. Suitably the connector compound comprises a small organic molecule.

Suitably the covalent bonds are formed between the connector compound and amino acid residues of the polypeptide.

Suitably said polypeptide comprises a cysteine residue, and suitably at least one of said three discrete covalent bonds for attachment of said connector compound to the polypeptide comprises a bond to said cysteine residue.

Suitably the connector compound has molecular symmetry corresponding to the number of covalent bonds by which it is attached to the polypeptide.

Suitably the connector compound possesses threefold molecular symmetry and the connector compound is attached to the polypeptide by three covalent bonds.

Suitably the connector compound comprises a structurally rigid chemical group.

Suitably the connector compound comprises tris-(bromomethyl)benzene (TBMB).

In another aspect, the invention relates to a complex as described above.

Suitably said polypeptide is an mRNA displayed polypeptide.

Suitably said polypeptide is comprised by a phage particle.

Nucleic acid has its usual meaning in the art and may comprise DNA, RNA or any other suitable nucleic acid. Nucleic acid may comprise oligonucleotides(s) or phage genome(s) or any other suitable example of nucleic acids known to the skilled worker.

Suitably said nucleic acid is comprised by said phage particle.

In another aspect, the invention relates to a genetically encoded polypeptide library comprising at least two different complexes as described above.

In another aspect, the invention relates to a method for making a complex, said method comprising
(i) providing a polypeptide
(ii) providing a connector compound
(iii) attaching said connector compound to said polypeptide by formation of at least
three covalent bonds between said connector compound and polypeptide.

Suitably the reactive groups of said polypeptide are reduced, and suitably the polypeptide comprising reduced reactive groups is purified by filtration before step (iii). Suitably when the reactive groups comprise cysteine they are reduced; in this embodiment the purification is purification from reducing agent, for example by filtration.

Suitably following the filtration purification step, the polypeptide is maintained in the reduced state for bonding to the connector compound by incubation in degassed buffer and in the presence of chelating agent.

Suitably step (iii) comprises incubation of the polypeptide and connector compound together at 30° C. at pH 8 in aqueous buffer comprising acetonitrile.

Suitably the polypeptide is comprised by a phage particle.

Suitably the connector compound comprises tris-(bromomethly)benzene (TBMB).

Suitably the tris-(bromomethly)benzene is present at 10 μm.

Suitably the tris-(bromomethly)benzene is present at 10 μm, the chelating agent is ethylenediaminetetraaceticacid (EDTA), the acetonitrile is present at 20% and the incubation step (iii) is conducted for 1 hour.

Suitably said method comprises the further step of (iv) cleaving one or more bonds of the polypeptide chain. This has the advantage of modifying the polypeptide chain. For example, this may have the benefit of producing multiple polypeptides attached to a single connector compound e.g. when the cleavage takes place on the polypeptide chain in between bonds between the polypeptide and the connector compound. Suitably said cleavage step comprises contacting said polypeptide with a protease.

In another aspect, the invention relates to a complex obtained by a method as described above.

In another aspect, the invention relates to a method for identifying a complex according to any preceding claim which is capable of binding to a ligand, the method comprising
(i) providing a complex as described above
(ii) contacting said complex with the ligand, and
(iii) selecting those complexes which bind said ligand.

Such selection method may be conducted in any suitable format. Suitably the ligand is immobilised. The complex is then contacted with the immobilised ligand. Non-binding complex(es) are then washed away. In this manner, those complexes which bind the immobilised ligand are enriched or selected. In one embodiment it is possible that the complexes may be recovered by release of the ligand i.e. releasing or eluting the complex-ligand moiety. However, suitably the complexes are recovered by elution (separation) from the immobilised ligand. In this embodiment the eluted complexes are no longer bound to the ligand at the elution step.

The complexes, or the polypeptide(s) of said complexes, or the polypeptide-connector compound conjugates of said complexes, may be useful in other settings. For example they may be useful as a basis for the design of drugs such as small drugs, or may be useful as CDRs or as binding moieties (e.g. for tagging or detection of their binding partner(s)) or other applications where the intimate knowledge of the interaction can be exploited.

In another aspect, the invention relates to a method as described above further comprising determining the sequence of the nucleic acid of said complex.

In another aspect, the invention relates to a method as described above further comprising the step of manufacturing a quantity of the complex isolated as capable of binding to said ligand.

In another aspect, the invention relates to a method as described above further comprising the step of manufacturing a quantity of the polypeptide-connector compound moiety comprised by the complex isolated as capable of binding to said ligand. In this embodiment the polypeptide-connector compound moiety may be advantageously synthesised in the absence of nucleic acid.

In another aspect, the invention relates to a method as described above further comprising the step of manufacturing a quantity of a polypeptide isolated or identified by a method of the invention, said manufacture comprising attaching the connector compound to the polypeptide, wherein said polypeptide is recombinantly expressed or chemically synthesized. In another embodiment the invention relates to a method as described above further comprising the step of manufacturing a quantity of a polypeptide isolated or identified by a method of the invention, said manufacture comprising attaching a connector compound to the polypeptide, wherein the connector compound may be different from the connector compound attached during isolation or identification of the polypeptide, provided that said connector compound is attached to said polypeptide by at least three covalent bonds, and wherein said polypeptide is recombinantly expressed or chemically synthesized.

In another aspect, the invention relates to a conjugate comprising
(i) at least two polypeptide molecules, and
(ii) at least one connector compound molecule,
wherein said at least two polypeptide molecules are each attached to said connector compound molecule by at least one covalent bond. Suitably said connector compound is bonded to said at least two polypeptide molecules by a total of at least three discrete covalent bonds.

In another aspect, the invention relates to a conjugate as described above wherein said conjugate comprises at least three polypeptide molecules, and wherein said at least three polypeptide molecules are each attached to said connector compound molecule by at least one covalent bond. Suitably said connector compound comprises tris-(bromomethly)benzene (TBMB).

In another aspect, the invention relates to a human plasma kallikrein inhibitor comprising an amino acid sequence selected from the group consisting of ACSDRFRNCPLWSGTCG (SEQ ID No. 1), ACSTERRYCPIEIFPCG (SEQ ID No. 2), ACAPWRTACYEDLMWCG (SEQ ID No. 3), ACGTGEGRCRVNWTPCG (SEQ ID No. 4), and ACSDRFRNCPADEALCG (SEQ ID No. 5).

BRIEF DESCRIPTION OF THE DRAWINGS

FIG. 2 shows assessment of the reaction conditions for linking phage displayed peptides to tris-(bromomethyl)benzene (TBMB).

FIG. 3 shows phage library design and sequences of selected clones. FIG. 3A: Amino acid sequence of peptide fusion proteins expressed by clones of library 1. The leader sequence is removed upon secretion of the protein by an *E. coli* protease leaving a peptide with an N-terminal alanine, two random 6-amino acid sequences flanked by three cysteines and a Gly-Gly-Ser-Gly (SEQ ID No. 20) linker that connects the peptide to the gene-3-protein. FIGS. 3B and 3C: Amino acid sequences of clones selected with human plasma kallikrein (B) and cathepsin G (C). Inhibitory activities of the TBMB modified peptide-D1-D2 fusion proteins are indicated. Sequence similarities are highlighted.

FIG. 4 shows affinity maturation of human plasma kallikrein inhibitors. FIG. 4A: Design of library 2, 3 and 4. In each library, one of the peptide loops has the sequence of a consensus motif identified in the first selections and the other contains six random amino acids. FIG. 4B: Amino acid sequences of clones selected with human plasma kallikrein. All clones derive from library 2. The inhibitory activities of TBMB modified peptide-D1-D2 fusion proteins are indicated. The colours highlight sequence similarities in the second binding loop.

FIG. 7 shows chemical reaction of the tri-functional compound TBMB with peptides containing one or two cysteines.

FIG. 10 shows assessment of the reaction conditions for linking phage displayed peptides to tris-(bromomethyl)benzene (TBMB).

FIG. 11 shows phage library design and sequences of selected clones. FIG. 11a: Amino acid sequence of peptide fusion proteins expressed by clones of library 1. The leader sequence is removed upon secretion of the protein by an *E. coli* protease leaving a peptide with an N-terminal alanine, two random 6-amino acid sequences flanked by three cysteines and a Gly-Gly-Ser-Gly (SEQ ID No. 20) linker that connects the peptide to the gene-3-protein. FIGS. 11b and 11c: Amino acid sequences of clones selected with human plasma kallikrein (b) and cathepsin G (c). Inhibitory activities of the TBMB modified peptide-D1-D2 fusion proteins are indicated. Sequence similarities are highlighted.

FIG. 12 shows affinity maturation of human plasma kallikrein inhibitors. FIG. 12a: Design of library 2, 3 and 4. In each library, one of the peptide loops has the sequence of a consensus motif identified in the first selections and the other contains six random amino acids. FIG. 12b: Amino acid sequences of clones selected with human plasma kallikrein. All clones derive from library 2. The inhibitory activities of TBMB modified peptide-D1-D2 fusion proteins are indicated. The sequence similarities in the second binding loop are highlighted.

FIG. 15 shows chemical reaction of the tri-functional compound TBMB with peptides containing one or two cysteine residues.

DETAILED DESCRIPTION OF THE INVENTION

Figure 1:
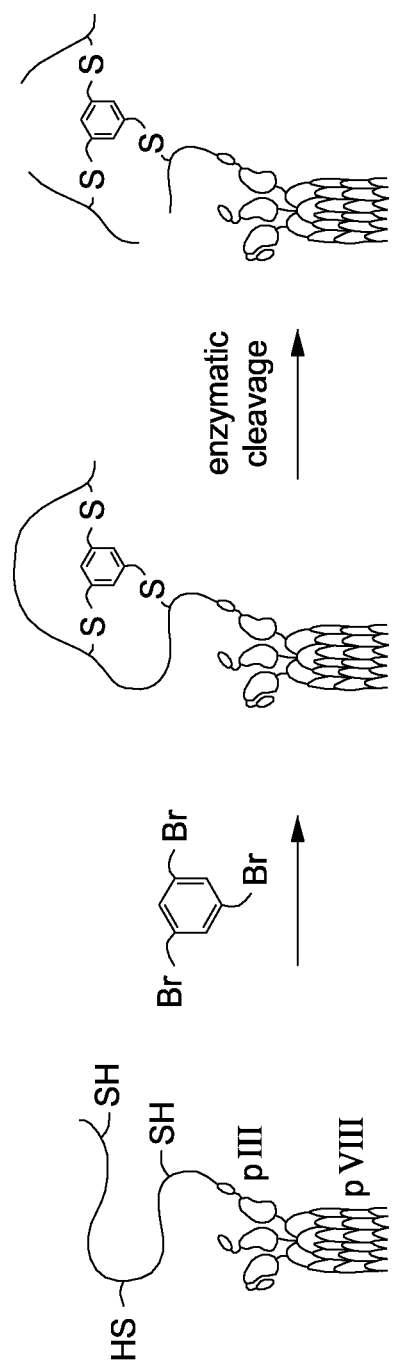
FIG. 1 shows generation of phage encoded combinatorial small chemical libraries. A phage encoded peptide with three cysteine residues is tethered to the tri-functional compound tris-(bromomethyl)benzene in a nucleophilic substitution reaction. The resulting chemical entities may be further modified through enzymatic reactions.

The invention brings novel features and attendant advantages which can be explained in more detail in connection with the generation of genetically encoded molecules with a core structure. In particular, the invention provides conformational restraint which is not achieved by known peptide cyclisation techniques. Moreover, the cross-linker in known systems such as those of Roberts (ibid) does not have the character of a central core/connector compound of the present invention. In the known systems, the cross-linker was used purely to replace a disulfide bond to generate a redox-insensitive cyclic peptide. There is no mention or suggestion of the concept of a central core with multiple appendages such as a triple covalently bonded connector compound-polypeptide complex as is taught herein. Indeed, it must be noted that in the present invention the polypeptide is linked to the core structure via at least three covalent bonds, providing a key structural difference compared to known systems. The linkage of a core structure (connector compound) to a genetically encoded polypeptide via three or more bonds is a complex reaction that has not been shown before.

Furthermore, the linkage of a polypeptide to a connector compound via at least three covalent bonds could yield several different products. This could cause difficulties in the selection process and in the decoding procedure. However, according to the present invention, a solution is provided using a connector compound with three reactive groups and preferably 3-fold rotational symmetry, which combination has the advantage of yielding a single product. Of course the skilled reader will appreciate that in certain obscure circumstances a connector compound with a 3-fold rotational symmetry may yield multiple products, most notably in the example of a tetrahedral molecule with three identical reactive groups; this also has a 3-fold rotational symmetry but it would yield two stereoisomers. Nevertheless, for ease of understanding such theoretical exceptions to the formation of a single product are acknowledged to be possible, suitably connector compounds with a 3-fold rotational symmetry yield a single product according to the present invention; in the rare circumstances noted above then suitably the polypeptide is chosen to avoid tetrahedral molecule formation and therefore maintain formation of only a single product.

The connector compound used in methods and compositions described herein is different from known bivalent cross-linkers (e.g. as used by Millward et al. ibid.) in the key requirement that a connector compound of the invention has at least three reactive groups that can form at least three covalent bonds with the target polypeptide. This feature yields numerous technical benefits to the invention. Firstly, by bonding the connector compound to the polypeptide via at least three covalent bonds, at least two polypeptide loops are created. These loops are formed between the first and second bonds, and between the second and third bonds of the connector compound to the polypeptide. The known linker described by Millward et al. can only connect two functional groups of a peptide, and cannot form two or more constrained peptide loops.

Advantages of Connector Compound—Polypeptide Bonding

There are a number of properties that distinguish molecules of the invention having 3 or more linkages to a connector compound from other molecules such as those with only 2 linkages. Some of these are explained below.

Firstly, it will be appreciated that molecules with two linkages to a connector compound are constrained through linking the flexible ends of a linear peptide together. This is also the case for molecules according to the present invention with 3 or more covalent bonds to a connector compound. However, the conformation of molecules according to the present invention with 3 or more covalent bonds to a connector compound is constrained by two additional effects that do not apply to a molecule with just two links:

i) the polypeptide bonded to the connector compound via at least three covalent bonds will comprise at least two constrained polypeptide loops ii) the polypeptide loops can interact with each other through non-covalent interactions to generate additional constraint, and iii) each of the loops occupies space that can not be occupied by the other loop(s) which additionally restricts their conformational flexibility.

In order to illustrate these points, the possible paths that can be taken by a polypeptide anchored at points A and C to a connector compound can be imagined. The introduction of an anchor point B, between points A and C, and to the same connector compound, will further limit the possible paths taken by the polypeptide, and thereby its conformational entropy. As binding of the peptide to a ligand requires loss of conformational entropy (and provided the peptide can adopt a conformation that is complementary to a ligand), the binding affinity between the peptide ABC constrained at the intermediate point B and the ligand is expected to be higher than the peptide AC. Thus, higher binding affinities are achievable using the constrained molecules of the present invention than has been possible in the prior art.

In addition to these key points, further advantages of the three or more covalent linkages between polypeptide and connector compound are set out below.

The molecules of the invention can bind to a target through the interaction of two or more conformationally constrained peptide loops. The more binding loops, the higher affinities and specificities can be obtained. A parallel effect occurs with antibodies—they bind best when multiple CDRs interact with the target. The molecules according to the present invention thus advantageously provide this technical benefit of multiple loops for interaction, which benefit is absent from molecules with fewer than three bonds.

In addition to the actual provision of a second (or subsequent) peptide loop, it is important to note that such a loop also brings the advantage of conformationally constraining the other loop(s). This can be through occupying some of the limited three-dimensional space which can then not be occupied by the other loop(s). Alternatively this can be through non-covalent interactions between the multiple loops.

From these advantages it can also be noted that more structured ligands generally bind with higher affinities (less entropy is lost upon binding) and specificities.

As discussed herein, the invention also provides for the production of looped peptide structures in which each of the two (or more) loops has a different property. Such structures are referred to as "dual specifics" to reflect the fact that a single molecular entity has dual specificities attributable to two different parts (loops) of the same overall structure. The advantage of such embodiments is that each loop can be selected or constructed to bind to a different target (such as an "antigen"). This represents a further distinguishing feature of a three bond system according to the present invention.

In addition to these effects, the molecules of the invention also provide the possibility of sandwiching a single antigen (or other entity) between two segments of polypeptide chain. This possibility is of course absent from polypeptide constructs with fewer than two loops. Of course the particular arrangement adopted may depend on the geometry of the particular construct being used, but the invention renders this possible which is in contrast to prior art techniques.

Of course the above discussion has made mention of the loops generated according to the present invention. In some embodiments, those loops are then cleaved. It is important to note that even in such embodiments, the loops are formed, it is simply that the looped molecule is treated as an intermediate which is then further processed by cleavage of the loops to produce a tethered-multiple-linear-peptide structure. In these embodiments, because the peptide is initially linked to the connector compound via three or more covalent bonds, after peptide cleavage the molecules will be decorated with three or more peptide moieties. Such molecules can form more interactions to targets and higher binding affinities/specificities are expected, which is a further advantage of the three-bonded system of the invention.

It is an advantage that molecules of the invention having two or more polypeptide loops can form more interactions with a target ligand and therefore can have higher affinities and/or specificities than polypeptide molecules with only a single loop. For example, it may be desirable to refine the second loop for better affinity, which is clearly not possible for single-loop molecules.

It is an advantage that in the complexes of the invention, the connector compound holds at least two polypeptide loops in close spatial proximity. These two or more loops can interact simultaneously with different epitopes on the same target ligand.

Moreover, the benefit of having two or more loops can be exploited in the manufacture of 'dual specific' molecules, where one loop has or is selected for a particular property or binding affinity, and the other loop for a different property or affinity. These molecules are referred to as "bispecifics" or "dual specifics". There are several types possible. For example, (a) bispecifics made by selecting on loop 1 and then on loop 2 (or more)
(b) two linked bicyclic macrocycles
(c) one bicyclic macrocycle plus peptide or drug.

For (a), this might typically be done by making/selecting one aliquot of a library against a first antigen, and another aliquot against a second antigen. The selected loops could then be combined pairwise, for example by standard techniques such as recombining the nucleic acid segments encoding the two loops to provide a new library of different combinations of first and second loops. The pairwise combined molecules (e.g. phage) may then be screened and/or selected for binding against both antigens sequentially. In this way, bispecifics capable of binding to two separate antigens may be made. Naturally this method can be augmented with further optional steps such as the binding affinities for each antigen could be improved by mutation of each loop, which may be directed or even random mutation.

In a variation of this technique, one aliquot of library could be selected for binding to a first antigen. The loop most important for binding could be identified, for example by inspection of "consensus sequences" among those selected as binders, and the other loop could be randomized and selected against the second antigen.

Most suitably bispecifics of this type such as described in (a) would be made on phage.

Variant molecules noted in (b) and (c) above could equally be made as phage (in a similar manner to above). Alternatively, most likely the two linked entities could be selected separately then fused at the step of chemical synthesis, which might simplify their selection/construction.

It is a further significant advantageous feature of aspects of the invention that, in addition to the connector compound of the invention serving to connect polypeptide segments through covalent bonds via the amino acid residues at the base of each peptide loop, the connector compound also engages in further non-covalent interactions (such as ionic bonds, hydrophobic interactions, hydrogen bonds, Van der Waals interactions) with additional elements of the polypeptide chain such as other amino acid residues. By contrast, the bivalent linker of Millward et al. is linear and highly flexible (propyl), and its sole role is to connect two ends of a polypeptide to create a redox-insensitive cyclic peptide. The linker of Millward et al. would not be expected to make significant non-covalent interactions with the polypeptide loop, as it is small and highly flexible, and indeed there is no evidence that it does. This advantage of the invention is further illustrated in the examples section, together with evidence of the advantageous noncovalent interactions. Thus suitably the polypeptide is joined to the connector compound by one or more non-covalent interactions, in addition to the covalent bond(s) discussed herein. This has the further advantage of providing additional level of structural constraint to the complex/conjugate of the invention.

It is an advantage of the invention that a molecule with multiple peptide loops is generally more structured than a polypeptide with a single peptide loop. Highly structured molecules tend to be more specific. Also, well structured molecules have generally better binding affinities. In addition, a molecule with multiple peptide loops can form more interactions with a target ligand than a polypeptide with a single peptide loop.

It is a further benefit of aspects of the invention that the connector compound of the invention also imposes conformational constraints deriving from its own chemical structure. For example, some chemical groups are known to be inflexible, to prevent rotation, to provide steric hindrance or restriction, to present a rigid structure or otherwise to provide scaffold or constraint to the complex. Thus suitably the connector compound of the invention comprises a scaffold group such as a rigid scaffold group. The function of this scaffold group is to provide molecular structure or constraint to the complex of the invention. In connection with a preferred connector compound of the invention, tris-(bromomethly)benzene (TBMB), this feature may be illustrated with reference to the planar structure of the benzene group of TBMB. This benzene group is rigid due to its planar character, and thus is able to serve as a scaffold group of the connector compound, in particular a rigid scaffold group.

Thus in a most preferred embodiment of the invention, the connector compound provides conformational constraints imposed by the at least three covalent bonds to the polypeptide, provides further structure via the non-covalent bonds between the connector compound and the polypeptide, and further the connector compound of the invention also imposes conformational constraints by nature of its own chemical structure serving as a rigid scaffold. For example, the planar structure of the benzene group when the connector compound comprises same such as when the connector compound is tris-(bromomethly)benzene (TBMB).

Connector Compound

The connector compound is sometimes referred to as the 'molecular core'. Suitably, the connector compound possesses molecular symmetry. Suitably, the connector compound possesses three reactive groups and possesses threefold symmetry. This has the advantage of producing only a single reaction product. If the connector compound is not a symmetric molecule, then multiple reaction products can be produced. This can lead to complications, or require that the desired isomer be separated from the other reaction products. By using a connector compound having the appropriate symmetry, such problems are advantageously ameliorated.

It is an advantage of the invention that the polypeptides produced have a greater complexity than prior art cyclic peptides. For example, polypeptides produced according to the present invention may possess more than two loops for interaction with other chemical entities. In addition, polypeptides produced according to the present invention enjoy a greater level of constraint than prior art based polypeptides. These two effects together create a further advantage in that multiple loops (or 'cycles') of the polypeptide are retained in close physical proximity to one another via their bonds to the common connector compound. This provides a further level of constraint on the conformation of those polypeptides.

Typically, cyclic polypeptides of the prior art are joined using multiple cysteine residues such as two cysteine residues to form a bridge between two parts of the peptide and thereby form a cyclic polypeptide. However, such molecules are redox sensitive. The method of Millward et al is directly focused at the production of cyclic peptides which are redox insensitive. In this regard, Millward et al's method departs from the prior art and teaches away from the use of cysteines as reactive groups for the modification of polypeptides. By contrast, according to the present invention, cysteines are preferred reactive groups.

When there are three or more reactive groups for at least three discrete covalent bonds to the connector compound, said reactive groups need not each be cysteines. For example, the three reactive groups may comprise one cysteine and two further suitable reactive groups, which might for example comprise lysine, selenocysteine or other(s). Most suitably all three reactive groups are cysteines.

Prior art techniques have only led to the production of single loop polypeptides. According to the present invention, at least two loops or even more may be produced by tethering the polypeptide at different points to the connector compound.

The method of the present invention involves a minimum of three bonds with the polypeptide. This has the advantage of greater molecular constraint. This has the further advantage of the presentation of multiple polypeptide loops for interaction with other moieties.

In known techniques, at best a cross linking agent has been introduced or joined to the polypeptide such as a genetically encoded polypeptide. By contrast, the present invention provides a connector compound for the multiple coordination of different parts of the same polypeptide.

Suitably the connector compound may be a small molecule. Suitably the connector compound is a small organic molecule.

Suitably the connector compound may be, or may be based on, natural monomers such as nucleosides, sugars, or steroids. Suitably the connector compound may comprise a short polymer of such entities, such as a dimer or a trimer.

Suitably the connector compound is a compound of known toxicity, suitably of low toxicity. Examples of suitable compounds include cholesterols, nucleotides, steroids, or existing drugs such as tamazapan.

Suitably the connector compound may be a macromolecule. Suitably the connector compound is a macromolecule composed of amino acids, nucleotides or carbohydrates.

Suitably the connector compound comprises reactive groups that are capable of reacting with functional group(s) of the target polypeptide to form covalent bonds.

The connector compound may comprise chemical groups as amines, thiols, alcohols, ketones, aldehydes, nitriles, carboxylic acids, esters, alkenes, alkynes, azides, anhydrides, succinimides, maleimides, alkyl halides and acyl halides.

Suitably the connector compound may comprise or may consist of tris(bromomethyl)benzene or a derivative thereof.

Suitably the connector compound has a 3-fold rotational symmetry such that reaction of three functional groups of the target polypeptide with the connector compound generates a single product isomer.

In some embodiments the connector compound may have a tetrahedral geometry such that reaction of four functional groups of the encoded polypeptide with the connector compound generates not more than two product isomers.

A suitable connector compound is 1,3,5-Tris(bromomethyl)benzene ('TBMB').

A suitable connector compound is 2,4,6-Tris(bromomethyl)mesitylene. It is similar to 1,3,5-Tris(bromomethyl)benzene but contains additionally three methyl groups attached to the benzene ring. This has the advantage that the additional methyl groups may form further contacts with the polypeptide and hence add additional structural constraint.

The connector compound of the present invention is selected from either a small molecule or a macromolecular structure. The said connector compound is composed of organic, inorganic or organic and inorganic components.

In a preferred embodiment, the connector compound is a small organic molecule as for example a linear alkane. More suitably the connector compound is a branched alkane, a cyclic alkane, a polycyclic alkane, an aromate, a heterocyclic alkane or a herterocyclic aromate, which offer the advantage of being less flexible (i.e. more rigid).

In another embodiment, the connector compound is selected from a macromolecular structure as for example a polypeptide, a polynucleotide or a polysaccharide.

The connector compound of the invention contains chemical groups that allow functional groups of the polypeptide of the encoded library of the invention to form covalent links with the connector compound. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

In one embodiment, the connector compound of the invention is tris(bromomethyl)benzene or a derivative thereof.

Polypeptide

The functional groups of the encoded polypeptides are suitably provided by side chains of natural or non-natural amino acids. The functional groups of the encoded polypeptides are suitably selected from thiol groups, amino groups, carboxyl groups, guanidinium groups, phenolic groups or hydroxyl groups. The functional groups of the encoded polypeptides may suitably be selected from azide, keto-carbonyl, alkyne, vinyl, or aryl halide groups. The functional groups of the encoded polypeptides for linking to a connector compound may suitably be the amino or carboxy termini of the polypeptide.

In some embodiments each of the functional groups of the polypeptide for linking to a connector compound are of the same type. For example, each functional group may be a cysteine residue.

In some embodiments the functional groups for linking to a connector compound may comprise two or more different types, or may comprise three or more different types. For example, the functional groups may comprise two cysteine residues and one lysine residue, or may comprise one cysteine residue, one lysine residue and one N-terminal amine.

In some embodiments, alternative amino acids such as natural amino acids may be suitable to chemically modify polypeptides such as phage displayed peptides of the invention.

Cysteine is the most suitable amino acid because it has the advantage that its reactivity is most different from all other amino acids. Reactive groups that could be used on the connector compound to react with thiol groups of cysteines are alkyl halides (or also named halogenoalkanes or haloalkanes). Examples are bromomethylbenzene (the reactive group exemplified by TBMB) or iodoacetamide. Other reactive groups that are used to couple selectively compounds to cysteines in proteins are maleimides. Examples of maleimides which may be used as connector compounds in the invention include: tris-(2-maleimidoethyl)amine, tris-(2-maleimidoethyl)benzene, tris-(maleimido)benzene. Selenocysteine is also a natural amino acid which has a similar reactivity to cysteine and can be used for the same reactions. Thus, wherever cysteine is mentioned, it is typically acceptable to substitute selenocysteine unless the context suggests otherwise. Most suitably cysteine is used.

Lysines (and primary amines of the N-terminus of peptides) are also suited as functional groups to modify peptides on phage by linking to a connector compound. However, they are more abundant in phage proteins than cysteines and there is a higher risk that phage particles might become cross-linked or that they might lose their infectivity. Nevertheless, we found that lysines are especially useful in intramolecular reactions (e.g. when a connector compound is already linked to the phage peptide) to form a second or consecutive linkage with the connector compound. In this case the connector compound reacts preferentially with lysines of the displayed peptide (in particular lysines that are in close proximity). Functional groups that react selectively with primary amines are succinimides, aldehydes or alkyl halides. Regarding alkyl halides, the reader will know that alkyl halides with different reactivities exist. In the bromomethyl group that we have used in a number of the accompanying examples, the electrons of the benzene ring can stabilize the cationic transition state. This particular alkyl halide is therefore 100-1000 times more reactive than alkyl halides that are not connected to a benzene group. Examples of succinimides for use as connector compound include tris-(succinimidyl aminotriacetate), 1,3,5-Benzenetriacetic acid. Examples of aldehydes for use as connector compound include Triformylmethane. Examples of alkyl halides for use as connector compound include 1,3,5-Tris(bromomethyl)-2,4,6-trimethylbenzene, 1,3,5-Tris(bromomethyl)benzene, 1,3,5-Tris(bromomethyl)-2,4,6-triethylbenzene.

In some embodiments, molecular linkers or modifications may be added to (or to create) functional groups of the encoded polypeptides before attachment of the connector compound wherein said linkers or modifications are capable to react with the connector compound.

The amino acids with functional groups for linking to a connector compound may be located at any suitable positions within the encoded polypeptide. In order to influence the particular structures or loops created, the positions of the amino acids having the functional groups may be varied by the skilled operator, e.g. by manipulation of the nucleic acid encoding the polypeptide in order to mutate the polypeptide produced.

Each of the amino acids of the encoded polypeptide may be a target for mutagenesis (e.g. restricted variance mutagenesis) according to the needs of the skilled worker or the purpose to which the invention is being applied. Clearly at least three functional groups for bonding to the connector compound are required on the polypeptide of interest. Amino acids other than those required for bonding to the connector compound may be freely varied according to operator needs and are termed 'variable amino acids'. Said variable amino acids of the encoded polypeptide (e.g. polypeptide library member(s)) may be randomised, partially randomised, or constant.

The target polypeptide comprises a connector compound binding segment. This is the region to which the connector compound is attached. Suitably the commentary regarding functional groups on the polypeptide is applied to this binding segment. Suitably the connector compound binding segment of the target polypeptide comprises 1 to 20 amino acid residues. Suitably the connector compound binding segment of the target polypeptide comprises fewer than 10 amino acids. This has the advantage of imposing further conformational constraint onto the polypeptide segment when it is attached to the connector compound.

The target polypeptide suitably comprises the sequence $AC(X)_6C(X)_6CG$ (SEQ ID No. 6), wherein X stands for a random natural amino acid, A for alanine, C for cysteine and G for glycine.

The target polypeptide suitably comprises the sequence $(X)lY(X)mY(X)nY(X)o$ (SEQ ID No. 67), wherein Y represents an amino acid with a functional group, X represents a random amino acid, m and n are numbers between 1 and 20 defining the length of intervening polypeptide segments and l and o are numbers between 0 and 20 defining the length of the flanking polypeptide segments.

In some embodiments, the complex of the invention may comprise a polypeptide with the sequence $AC(X)_6C(X)_6CG$ (SEQ ID No. 6). In one embodiment, a library member or complex of the invention may comprise a mesitylene connector compound and a polypeptide with the sequence $AC(X)_6C(X)_6CG$ (SEQ ID No. 6), wherein the polypeptide is tethered to the exo-cyclic methyl groups of the connector compound via the cysteine residues of the polypeptide forming three thioether bonds therewith, and wherein X stands for an amino acid, (suitably a natural amino acid), A for alanine, C for cysteine and G for glycine.

Suitably the target polypeptide comprises an inhibitor of human plasma kallikrein and the polypeptide comprises one or more of the amino acid sequences GCSDRFRNCPADEALCG (SEQ ID No. 7), ACSDRFRNCPLWSGTCG (SEQ ID No. 1), ACSTERRYCPIEIFPCG (SEQ ID No. 2), ACAPWRTACYEDLMWCG (SEQ ID No. 3), ACGTGEGRCRVNWTPCG (SEQ ID No. 4) or a related sequence.

By related sequence is meant an amino acid sequence having at least 50% identity, suitably at least 60% identity, suitably at least 70% identity, suitably at least 80% identity, suitably at least 90% identity, suitably at least 95% identity, suitably at least 98% identity, suitably at least 99% identity. Identity is suitably judged across a contiguous segment of at least 10 amino acids, suitably least 12 amino acids, suitably least 14 amino acids, suitably least 16 amino acids, suitably least 17 amino acids or the full length of the reference sequence.

Suitably the target polypeptide comprises an inhibitor of human cathepsin G and the polypeptide comprises one or more of the amino acid sequences ACEYGDLWCGWDP-PVCG (SEQ ID No. 8), ACIFDLGFCHNDWWNCG (SEQ ID No. 9), ACLRAQEDCVYDRGFCG (SEQ ID No. 10) or a related sequence.

Suitably the target polypeptide comprises an inhibitor of human urokinase-type plasminogen activator and the polypeptide comprises one or more of the amino acid sequences ACNSRFSGCQIDLLMCG (SEQ ID No. 11), ACSRYEVDCRGRGSACG (SEQ ID No. 12) or a related sequence.

Suitably the target polypeptide is comprised by a library of polypeptides containing at least 10exp5 members, more suitably at least 10exp9 members. The invention also relates to such libraries.

Reactive Groups of Polypeptide

The connector compound of the invention may be bonded to the polypeptide via functional or reactive groups on the polypeptide. These are typically formed from the side chains of particular amino acids found in the polypeptide polymer. Such reactive groups may be a cysteine side chain, a lysine side chain, or an N-terminal amine group or any other suitable reactive group.

Suitably at least one functional group is a cysteine group. Groups such as lysine or the N-terminal amines are typically not reactive enough to bond with the connector compound on their own within a convenient time frame. However, once the connector compound has been attracted or bonded to at least one cysteine, then ordinary reaction kinetics mean that the lysine or amine bonds can rapidly and stably form thereafter. For this reason, suitably at least one of the functional groups is a cysteine group.

If reactive groups on the polypeptide other than cysteine/lysine/amine groups are desired, then a different connector compound may be chosen in order to pair with the particular functional reactive groups of choice on the target polypeptide.

Suitably cysteine, lysine or amine groups are used as the functional or reactive groups on the polypeptide of interest.

Suitably at least three covalent bonds are formed between the connector compound and the polypeptide of interest.

In some embodiments, four bonds or even more may be formed between the connector compound and the polypeptide of interest. However, if more than four bonds are used, then typically the product mixtures formed become increasingly complex and may hinder the subsequent uses or applications. For this reason, three bonds or four bonds between the connector compound and the polypeptide of interest are preferred. In any embodiment, molecular symmetry of the connector compound is preferred. Most preferred are connector compounds having three functional or reactive groups. Most preferred are connector compounds having three fold molecular symmetry.

The functional groups of the genetically encoded polypeptides of the invention are capable of forming covalent bonds to the connector compound/molecular core. Functional groups are specific groups of atoms within either natural or non-natural amino acids. Preferentially, functional groups with a distinctive chemical reactivity are used to link the polypeptide the connector compound to form the complex of the invention. The usage of said distinctive functional groups allows bonding of the connector compound/molecular core exclusively to the designated functional groups of the polypeptide but not to other chemical groups of either the diversity elements of the polypeptide, the nucleic acid or other components of the complex.

Suitable functional groups of natural amino acids are the thiol group of cysteine, the amino group of lysine, the carboxyl group of aspartate or glutamate, the guanidinium group of arginine, the phenolic group of tyrosine or the hydroxyl group of serine. Non-natural amino acids can provide a wide range of functional groups including an azide, a keto-carbonyl, an alkyne, a vinyl, or an aryl halide group. The amino and carboxyl group of the termini of the polypeptide can also serve as functional groups to form covalent bonds to a connector compound/molecular core.

The encoded polypeptides of the invention suitably contain at least three functional groups. Said polypeptides can also contain four or more functional groups. The more functional groups are used, the more diversity segments can be tethered to the connector compound/molecular core. However, the linkage of excessive numbers of functional groups to a connector compound/molecular core is not recommended since this can lead to an unmanageable number of product isomers. Suitably three, four or five covalent bonds to a connector compound are used; most suitably three or four covalent bonds; most suitably three covalent bonds.

In a preferred embodiment, encoded polypeptides with three functional groups are generated. Reaction of said polypeptides with a connector compound/molecular core having a three-fold rotational symmetry generates a single product isomer. The generation of a single product isomer is favourable for several reasons. The nucleic acids (sometimes referred to as the 'genetic codes') of the compound libraries do encode only the primary sequences of the polypeptide but not the isomeric state of the molecules that are formed upon reaction of the encoded polypeptide with the molecular core. If only one product isomer can be formed, the assignment of the nucleic acid to the product isomer is clearly defined. If multiple product isomers are formed, the nucleic acid can not give information about the nature of the product isomer that was isolated in a screening or selection process. The formation of a single product isomer is also advantageous if a specific member of a library of the invention is synthesized. In this case, the chemical reaction of the polypeptide with the connector compound yields a single product isomer rather than a mixture of isomers.

In another embodiment of the invention, encoded polypeptides with four functional groups are generated. Reaction of said polypeptides with a connector compound/molecular core having a tetrahedral symmetry generates two product isomers.

Even thought the two different product isomers are encoded by one and the same nucleic acid ('genetic code'), the isomeric nature of the isolated isomer can be determined by chemically synthesizing both isomers, separating the two isomers and testing both isomers for binding to a target ligand.

In one embodiment of the invention, at least one of the functional groups of the polypeptides is orthogonal to the remaining functional groups. The use of orthogonal functional groups allows to directing said orthogonal functional groups to specific sites of the molecular core. Linking strategies involving orthogonal functional groups may be used to limit the number of product isomers formed. In other words, by choosing distinct or different functional groups for one or more of the at least three bonds to those chosen for the remainder of the at least three bonds, a particular order of bonding or directing of specific functional groups of the polypeptide to specific positions on the connector compound may be usefully achieved.

In another embodiment, the functional groups of the encoded polypeptide of the invention are reacted with molecular linkers wherein said linkers are capable to react with a connector compound/molecular scaffold so that the linker will intervene between the connector compound and the polypeptide in the final bonded state.

Suitable amino acids of the members of the genetically encoded combinatorial chemical libraries can be replaced by any natural or non-natural amino acid. Excluded from these exchangeable amino acids are the ones harbouring functional groups for cross-linking the polypeptides to a molecular core. A group of adjacent amino acids that can be varied is defined as a polypeptide segment. The size of a single polypeptide segment suitably ranges from 1 to 20 amino acids. The polypeptide segments have either random sequences, constant sequences or sequences with random and constant amino acids. The amino acids with functional groups are either located in defined or random positions within the encoded polypeptide of the invention.

In one embodiment, the polypeptide segments that are bounded by two amino acids harbouring functional groups for bonding with a connector compound/molecular core are short amino acid sequences of 10 or fewer amino acids. Reaction of said encoded polypeptide sequences with a molecular core generates library members with high conformational constraint. Conformational constrained ligands are generally more specific and have higher binding affinities. The conformational constraint can also protect the ligands from proteolytic degradation for example in bodily fluids.

In one embodiment, an encoded polypeptide with three functional groups has the sequence (X)lY(X)mY(X)nY(X)o (SEQ ID No. 67), wherein Y represents an amino acid with a functional group, X represents a random amino acid, m and n are numbers between 1 and 20 defining the length of intervening polypeptide segments and l and o are numbers between 0 and 20 defining the length of the flanking polypeptide segments.

In a preferred embodiment, an encoded polypeptide library of the invention has the sequence $AC(X)_6C(X)_6CG$, wherein A represents alanine, C represents cysteine, X represents a random natural amino acid and G represents glycine.

Alternatives to thiol-mediated conjugations can be used to attach the connector compound to the peptide via covalent interactions. Alternatively these techniques may be used in modification or attachment of further moieties (such as small molecules of interest which are distinct from the connector compound) to the polypeptide after they have been selected or isolated according to the present invention—in this embodiment then clearly the attachment need not be covalent and may embrace non-covalent attachment. These methods may be used instead of (or in combination with) the thiol mediated methods by producing phage that display proteins and peptides bearing unnatural amino acids with the requisite chemical functional groups, in combination small molecules that bear the complementary functional group, or by incorporating the unnatural amino acids into a chemically or recombinantly synthesised polypeptide when the molecule is being made after the selection/isolation phase.

The unnatural amino acids incorporated into peptides and proteins on phage may include 1) a ketone functional group (as found in para or meta acetyl-phenylalanine) that can be specifically reacted with hydrazines, hydroxylamines and their derivatives (Addition of the keto functional group to the genetic code of *Escherichia coli*. Wang L, Zhang Z, Brock A, Schultz P G. Proc Natl Acad Sci USA. 2003 Jan. 7; 100(1):56-61; Bioorg Med Chem. Lett. 2006 Oct. 15; 16(20):5356-9. Genetic introduction of a diketone-containing amino acid into proteins. Zeng H, Xie J, Schultz P G), 2) azides (as found in p-azido-phenylalanine) that can be reacted with alkynes via copper catalysed "click chemistry" or strain promoted (3+2) cyloadditions to form the corresponding triazoles (Addition of p-azido-L-phenylalanine to the genetic code of *Escherichia coli*. Chin J W, Santoro S W, Martin A B, King D S, Wang L, Schultz P G. J Am Chem. Soc. 2002 Aug. 7; 124(31):9026-7; Adding amino acids with novel reactivity to the genetic code of *Saccharomyces cerevisiae*. Deiters A, Cropp T A, Mukherji M, Chin J W, Anderson J C, Schultz P G. J Am Chem. Soc. 2003 Oct. 1; 125(39):11782-3), or azides that can be reacted with aryl phosphines, via a Staudinger ligation (Selective Staudinger modification of proteins containing p-azidophenylalanine. Tsao M L, Tian F, Schultz P G. Chembiochem. 2005 December; 6(12):2147-9), to form the corresponding amides, 4) Alkynes that can be reacted with azides to form the corresponding triazole (In vivo incorporation of an alkyne into proteins in *Escherichia coli*. Deiters A, Schultz P G. Bioorg Med Chem. Lett. 2005 Mar. 1; 15(5):1521-4), 5) Boronic acids (boronates) than can be specifically reacted with compounds containing more than one appropriately spaced hydroxyl group or undergo palladium mediated coupling with halogenated compounds (Angew Chem Int Ed Engl. 2008; 47(43):8220-3. A genetically encoded boronate-containing amino acid., Brustad E, Bushey M L, Lee J W, Groff D, Liu W, Schultz P G), 6) Metal chelating amino acids, including those bearing bipyridyls, that can specifically co-ordinate a metal ion (Angew Chem Int Ed Engl. 2007; 46(48):9239-42. A genetically encoded bidentate, metal-binding amino acid. Xie J, Liu W, Schultz P G).

Unnatural amino acids may be incorporated into proteins and peptides displayed on phage by transforming *E. coli* with plasmids or combinations of plasmids bearing: 1) the orthogonal aminoacyl-tRNA synthetase and tRNA that direct the incorporation of the unnatural amino acid in response to a codon, 2) The phage DNA or phagemid plasmid altered to contain the selected codon at the site of unnatural amino acid incorporation (Proc Natl Acad Sci USA. 2008 Nov. 18; 105(46):17688-93. Protein evolution with an expanded genetic code. Liu C C, Mack A V, Tsao M L, Mills J H, Lee H S, Choe H, Farzan M, Schultz P G, Smider V V; A phage display system with unnatural amino acids. Tian F, Tsao M L, Schultz P G. J Am Chem. Soc. 2004 Dec. 15; 126(49):15962-3). The orthogonal aminoacyl-tRNA synthetase and tRNA may be derived from the *Methancoccus janaschii* tyrosyl pair or a synthetase (Addition of a photocrosslinking amino acid to the genetic code of *Escherichia coli*. Chin J W, Martin A B, King D S, Wang L, Schultz P G. Proc Natl Acad Sci USA. 2002 Aug. 20; 99(17):11020-4) and tRNA pair that naturally incorporates pyrrolysine (Multistep engineering of pyrrolysyl-tRNA synthetase to genetically encode N(epsilon)-(o-azidobenzyloxycarbonyl)lysine for site-specific protein modification. Yanagisawa T, Ishii R, Fukunaga R, Kobayashi T, Sakamoto K, Yokoyama S. Chem. Biol. 2008 Nov. 24; 15(11):1187-97; Genetically encoding N(epsilon)-acetyllysine in recombinant proteins. Neumann H, Peak-Chew S Y, Chin J W. Nat Chem. Biol. 2008 April; 4(4):232-4. Epub 2008 Feb. 17). The codon for incorporation may be the amber codon (UAG) another stop codon (UGA, or UAA), alternatively it may be a four base codon. The aminoacyl-tRNA synthetase and tRNA may be produced from existing vectors, including the pBK series of vectors, pSUP (Efficient incorporation of unnatural amino acids into proteins in *Escherichia coli*. Ryu Y, Schultz P G. Nat. Methods. 2006 April; 3(4):263-5) vectors and pDULE vectors (Nat. Methods. 2005 May; 2(5):377-84. Photo-cross-linking interacting proteins with a genetically encoded benzophenone. Farrell I S, Toroney R, Hazen J L, Mehl R A, Chin J W). The *E. coli* strain used will express the F' pilus (generally via a tra operon). When amber suppression is used the *E. coli* strain will not itself contain an active amber suppressor tRNA gene. The amino acid will be added to the growth media, preferably at a final concentration of 1 mM or greater. Efficiency of amino acid incorporation may be enhanced by using an expression construct with an orthogonal ribosome binding site and translating the gene with ribo-X (Evolved orthogonal ribosomes enhance the efficiency of synthetic genetic code expansion. Wang K, Neumann H, Peak-Chew S Y, Chin J W. Nat. Biotechnol. 2007 July; 25(7):770-7). This may allow efficient multi-site incorporation of the unnatural amino acid providing multiple sites of attachment to the ligand.

Phage Purification

Any suitable means for purification of the phage may be used. Standard techniques may be applied in the present invention. For example, phage may be purified by filtration or by precipitation such as PEG precipitation; phage particles may be produced and purified by polyethylene-glycol (PEG) precipitation as described previously.

In case further guidance is needed, reference is made to Jespers et al (Protein Engineering Design and Selection 2004 17(10):709-713. Selection of optical biosensors from chemisynthetic antibody libraries.) Suitably phage may be purified as taught therein. The text of this publication is specifically incorporated herein by reference for the method of phage purification; in particular reference is made to the materials and methods section starting part way down the right-column at page 709 of Jespers et al.

Moreover, the phage may be purified as published by Marks et al J. Mol. Biol. vol 222 pp 581-597, which is specifically incorporated herein by reference for the particular description of how the phage production/purification is carried out.

In case any further guidance is needed, phage may be reduced and purified as follows. Approximately $5 \times 10^{12}$ phage particles are reacted with 1 mM dithiothreitol (DTT) for 30 min at room temperature, then PEG precipitated. After rinsing with water, the pellet is resuspended in 1 ml of reaction buffer (10 mM phosphate buffer, 1 mM EDTA, pH 7.8). The phage are then optionally reacted with 50 µl of 1.6 mM N-[(2-iodoacetoxy)ethyl]-N-methylamino-7-nitrobenz-2-oxa-1,3-diazole (NBDIA) (Molecular Probes) for 2 h at room temperature, or more suitably reacted with the connector compound as described herein. The reaction is terminated by PEG precipitation of phage particles.

A yet still further way in which the phage may be produced/purified is as taught in Schreier and Cortese (A fast and simple method for sequencing DNA cloned in the single-stranded bacteriophage M13. Journal of molecular biology 129(1):169-72, 1979). This publication deals with the chain termination DNA sequencing procedure of Sanger et al. (1977), which requires single-stranded DNA as template. M13 phage DNA exists as a single strand and therefore every DNA sequence cloned in M13 can be easily obtained in this form. Schreier and Cortese show that M13 single-stranded DNA pure enough to be used as a template for sequence determination can be prepared by simple centrifugation of the phage particle and extraction with phenol. The Schreier and Cortese publication is specifically incorporated herein by reference for the method of purification of the phage. For the avoidance of doubt, the phenol extraction is not performed for making complexes according to the present invention since that is for the purpose of nucleic acid purification. Thus the phenol step of Schreier and Cortese is suitably omitted. The Schreier and Cortese method is followed only to the point of purified phage particles.

Thus there are myriad techniques well known in the art for purification of phage. In the context of the present invention such purification is used for the removal of reducing agent used to reduce the functional groups in the polypeptide of interest for bonding to the connector compound, particularly when such bonding is via cysteine residues.

Optionally, especially advantageous techniques for phage purification may be adopted as discussed in the reaction chemistry section below. It should be expressly noted that these techniques are not regarded as essential for the invention, but may represent especially helpful methods or even the best mode of making the phage particles of the invention. However, provided attention is paid to avoiding reoxidation of the reduced functional/reactive groups on the phage at the stage of removal of the reducing agent before attachment of the connector compound then in principle any technique may be used to accomplish this. The filtration techniques described are particularly effective but also more complicated than standard techniques so the operator will choose the technique best suited to their particular working of the invention. Most suitably the filtration technique is employed.

Reaction Chemistry

In addition to the conceptual insights in connection with the triply bonded connector compound—polypeptide conjugates and phage particles of the invention, the inventors have also derived a precise set of chemical conditions which can be deployed in order to achieve the chemical linking whilst maintaining the integrity of the genetically encoded portion of the product. Prior art technologies for modification of polypeptides have involved harsh chemistry and independent polypeptide modification reactions. By contrast, the present invention provides novel chemical conditions for the modification of polypeptides whilst advantageously retaining the function and integrity of the genetically encoded element of the product. Specifically, when the genetically encoded element is a polypeptide displayed on the surface of a phage encoding it, the chemistry advantageously does not compromise the biological integrity of the phage. It is disclosed herein that there is a narrow window of conditions for which these chemical reactions can be enhanced or facilitated. In particular, as will be explained in more detail below, the solvents and temperatures used are important to an efficient reaction. Furthermore, the concentration of the reagents used are also instrumental in promoting the correct bonding, whilst ameliorating or eliminating cross linking or damaging of the polypeptide moieties which are being modified.

In particular, it is disclosed that the reduction of the cysteines in the target polypeptide is required for the most efficient reaction. Clearly, the reducing agent used to chemically reduce those cysteines must be removed in order to perform the desired attachment. One known technique is to use dithiothreitol (DTT) for reduction of the cysteines, and for the removal of the reducing agent to precipitate the particles such as the phage particles in a precipitation reaction. Such precipitation reactions typically involve 20% polyethylene glycol (PEG) together with 2.5 molar NaCl which leads to precipitation of the phage particles. However, the inventors disclose that in some experiments these specific standard conditions did not lead to an efficient reaction of the cysteine residues in the polypeptide with the connector compound, most likely due to reoxidation of a proportion of the cysteine residues which had been reduced. This could not have been predicted from an understanding of the prior art. It should be noted that this standard technique may still find application in the invention, in particular when the skilled worker is alert to the disclosed need to be vigilant in assessing/avoiding reoxidation. However, the inventors have addressed this cryptic problem of how to remove the reducing agent whilst maintaining the cysteines in their reduced state. As will be disclosed in more detail below, the solutions are found in a range of strategies including the use of tris carboxyethyl-phosphine, degassed buffer, the use of chelators in the reaction mixture, and filtration in order to extract the particles under favourable chemical conditions.

Reaction conditions e.g. for attachment of the connector compound to the target polypeptide should be chosen carefully. Choice of conditions may vary depending upon the application to which the invention is being put. Particular care is required when the target polypeptide is comprised by a phage particle. Guidance is provided throughout the specification and examples section.

Reaction conditions as reaction temperature, connector compound concentration, solvent and/or pH should be chosen to allow efficient reaction of the functional groups of the target polypeptide with the connector compound, but leave the nucleic acid encoding the polypeptide in a condition that allows to decode (e.g. to sequence) and/or propagate the isolated molecules (e.g. by PCR or by phage propagation or any other suitable technique). Moreover, the reaction conditions should leave the phage coat protein in a condition that allows it to propagate the phage.

Thiol groups of a phage encoded polypeptide may be reduced with reducing agent prior to connector compound attachment. In such embodiments, in particular in phage display embodiments, or in particular when the reducing agent is TCEP, the excess of reducing agent is suitably removed by filtration e.g. filtration of the phage. This is especially advantageous since the present inventors disclose for the first time that conventional techniques for removal of reducing agents such as PEG/NaCl precipitation can sometimes lead to sub-optimal reaction with connector compound, likely due to reoxidation of the reduced functional side groups of the target polypeptide. Thus it is an advantage of embodiments in which the target polypeptide is prepared by reduction followed by purification (removal of reducing agent) via filtration that superior preservation of the reduced (and hence reactive) functional groups of the polypeptide is achieved.

In the present invention, reaction conditions are applied that on the one hand allow to efficiently link the encoded polypeptide to a connector compound and on the other hand leave the appended nucleic acid (and phage coat proteins) in a condition that allows its propagation or decoding. Said reaction conditions are for example the reaction temperature, connector compound concentration, solvent composition or pH.

In one embodiment of the present invention, thiol groups of cysteine residues are used as functional groups to link polypeptides to a molecular core. For some chemical reactions, the thiol groups of the polypeptides need to be reduced. Thiol groups in phage displayed polypeptides are efficiently reduced by addition of a reducing agent as for example tris(carboxyethyl)phosphine (TCEP). Since an excess of reducing agent can interfere with the attachment reaction it is efficiently removed by filtration of the phage.

Re-oxidation of the thiol groups after removal of TCEP is suitably prevented by degassing of the reaction buffer.

Re-oxidation of the thiol groups is also suitably prevented by complex formation of metal ions by chelation, for example chelation with ethylenediaminetetraacetic acid (EDTA).

Most suitably re-oxidation of the thiol groups is prevented or inhibited by both chelation and use of degassed buffers.

In one embodiment of the present invention, attachment of the polypeptide to the connector compound is accomplished by reacting the reactive groups of the polypeptide such as thiol groups of a phage encoded polypeptide with the connector compound for one hour.

Suitably they are reacted at 30° C.

Suitably they are reacted with connector compound (such as tris(bromomethyl)benzene) at a concentration of 10 µM.

Suitably reaction is in aqueous buffer.

Suitably reaction is at pH 8.

Suitably reaction buffer contains acetonitrile. Suitably reaction buffer contains 20% acetonitrile.

Most suitably the reaction features two or more of the above conditions. Suitably the reaction features three or more of the above conditions. Suitably the reaction features four or more of the above conditions. Suitably the reaction features five or more of the above conditions. Suitably the reaction features six or more of the above conditions. Suitably the reaction features each of the above conditions.

These reaction conditions are optimized to quantitatively react thiol groups of a polypeptide with the reactive groups of tris(bromomethyl)benzene. Under the same reaction conditions, about 20% of the phage particles remain infective to bring the genetic code into bacterial cells for propagation and decoding.

In one embodiment the connector compound, such as TBMB, may be attached to the target polypeptide, such as a phage encoded polypeptide, by reaction (incubation) of thiol groups of the polypeptide for one hour at 30° C. with TBMB (i.e. tris(bromomethyl)benzene) at a concentration of 10 µM in aqueous buffer pH 8 containing 20% acetonitrile.

The inventors also disclose the effect of concentration of the connector compound in the reaction on phage infectivity. In particular the invention suitably minimises the concentration of connector compound used in the reaction. In other words, the lower the concentration of connector compound used at the time of reaction with the polypeptide of the phage, the better, provided always that sufficient connector compound becomes joined to the phage polypeptide. The advantage of minimising the connector compound present in this way is superior preservation of phage infectivity following coupling of the connector compound. For example, when the connector compound is TBMB, concentrations of connector compound greater than 100 µM can compromise infectivity. Thus suitably when the connector compound is TBMB then suitably the concentration of TBMB present at the time of bonding to the polypeptide is less than 100 µM. Most suitably the concentration is as disclosed in the examples section.

Post Attachment Modification

In some embodiments the polypeptide-connector compound complex may be modified at a time following attachment.

In some embodiments, the polypeptide elements of the invention are proteolytically cleaved once they are tethered to a connector compound/molecular core. The cleavage generates ligands having discrete peptide fragments tethered to a connector compound/molecular core.

For example, one or more amide bonds of the polypeptide may be proteolytically cleaved after tethering the polypeptide to the molecular core. This has the advantage of creating short polypeptides, each joined to the connector compound by at least one covalent bond, but which present different molecular structures which are retained in a complex comprising the nucleic acid encoding the parent polypeptide. The polypeptide cleavage is suitably catalysed by any suitable means known in the art such as controlled hydrolysis or more suitably enzymatic cleavage by a suitable protease. The protease may be any suitable protease but is preferably a protease with a specific polypeptide recognition sequence or motif. This advantageously leads to production of more defined and/or more predictable polypeptide cleavage products. Indeed, in this embodiment, protease recognition sequences may be systematically added or removed from the target polypeptide, for example by manipulation of the nucleic acid(s) encoding it. This advantageously provides a greater degree of control and permits greater diversity to be produced in the molecules displayed according to the present invention. Most suitably the polypeptide comprises at least one protease recognition site. Suitably each said cleavage site is comprised within amino acid sequence(s) in between functional groups on the polypeptide used for covalent bonding to the connector compound. Suitably each said recognition site is comprised within amino acid sequence(s) in between functional groups on the polypeptide used for covalent bonding to the connector compound.

The peptide loops are suitably cleaved with a protease that recognizes and processes polypeptides at specific amino acid positions such as trypsin (arginine or lysine in P1 position) or thermolysin (aliphatic side chains in P1 position). The enzyme is used at a concentration that allows efficient processing of the peptide loops of the displayed molecule but spares the phage particle. The optimal conditions can vary depending on the length of the polypeptide loops and on the protease used. Trypsin for example is typically used at 200 nM in TBS-Ca buffer (25 mM Tris HCl/137 mM NaCl/1 mM $CaCl_2$, pH 7.4) for 10 min at 10° C. A whole range of proteases that are suitable to modify displayed polypeptides but that spare the phage are described in Kristensen, P. and Winter, G. (Proteolytic selection for protein folding using filamentous bacteriophages Fold Des. 1998; 3(5):321-8). The enzymatic processing of peptide on phage may be a 'partial proteolysis' since it can not be excluded that a limited number of phage coat proteins are cleaved. Thus in optimisation of the conditions, the best balance between maximised cleavage of the target and maximum sparing of the phage particles is suitably chosen.

Suitably the target polypeptide comprises at least one such proteolytic cleavage site. Suitably the target polypeptide comprises at least two such proteolytic cleavage sites. Suitably the target polypeptide comprises at least three such proteolytic cleavage sites.

In each such proteolysis embodiment, suitably the first such protease site occurs distal to the first covalent bond between the target polypeptide and the connector compound. This has the advantage that the connector compound is retained on the complex since if the target polypeptide is cleaved before the first such covalent bond, then the polypeptide-connector compound complex will be separated from the nucleic acid encoding the target polypeptide, which is undesirable for the majority of applications of the invention.

The use of short loops (short being e.g. 6 amino acid residues or less) may compromise the ability of some proteases to cleave within the loops. In this case it may be desirable to select longer loops which are likely to be more accessible to the protease. Furthermore after cleavage of the loops by endoprotease, it may be desirable to cut back the loops further with other endoproteases, or indeed by exoproteases, such as carboxypeptidases or aminopeptidases.

When the target polypeptide comprises more than one such protease site, suitably each of the sites occurs between two covalent bonds made between the target polypeptide and the connector compound. Multiple cleavage sites may occur between bonds if necessary.

In cleavage embodiments, suitably the parent polypeptide will be considered as a whole for the assessment of whether or not it is attached to the connector compound by at least three covalent bonds. More suitably the target polypeptide will be considered to be the intact (uncleaved) polypeptide when assessing whether or not it is attached to the connector compound by at least three covalent bonds. Such uncleaved polypeptides will typically be bicyclic.

Synthesis

It should be noted that once the polypeptide of interest is isolated or identified according to the present invention, then its subsequent synthesis may be simplified wherever possible. For example, the sequence of the polypeptide of interest may be determined, and it may be manufactured synthetically by standard techniques followed by reaction with a connector compound in vitro. When this is performed, standard chemistry may be used since there is no longer any need to preserve the functionality or integrity of the genetically encoded carrier particle. This enables the rapid large scale preparation of soluble material for further downstream experiments or validation. In this regard, large scale preparation of the candidates or leads identified by the methods of the present invention could be accomplished using conventional chemistry such as that disclosed in Meloen and Timberman.

Thus, the invention also relates to manufacture of polypeptides or conjugates selected as set out herein, wherein the manufacture comprises optional further steps as explained below. Most suitably these steps are carried out on the end product polypeptide/conjugate made by chemical synthesis, rather than on the phage.

Optionally amino acid residues in the polypeptide of interest may be substituted when manufacturing a conjugate or complex e.g. after the initial isolation/identification step.

In order to illustrate the modifications/additions being described, it is helpful to consider the example of selection of a polypeptide that reacts with a receptor. It may be desirable to extend the peptide at its N-terminus or C-terminus. This may be useful for example in making a macrocyclic peptide that binds to one target, with a tail such as a linear tail that binds to a second target, for example a cell penetrating peptide such as those derived from such as VP22, HIV-Tat, a homeobox protein of *Drosophila* (Antennapedia) or chemically designed proteins such as polyarginine, or other such peptide e.g. as described in (Chen and Harrison Biochemical Society Transactions (2007) Volume 35, part 4, p821 "Cell-penetrating peptides in drug development: enabling intracellular targets"). This would have the advantage of assisting or enabling a macrocycle that had been selected against an particular target such as an intracellular target to enter a cell.

To extend the peptide, it may simply be extended chemically at its N-terminus or C-terminus using standard solid phase or solution phase chemistry. Standard protein chemistry may be used to introduce an activatable N- or C-terminus. Alternatively additions may be made by fragment condensation or native chemical ligation e.g. as described in (Dawson P E, Muir T W, Clark-Lewis I, Kent, S B H. 1994. Synthesis of Proteins by Native Chemical Ligation. Science 266:776-779), or by enzymes, for example using subtiligase as described in (Subtiligase: a tool for semisynthesis of proteins Chang T K, Jackson D Y, Burnier J P, Wells J A Proc Natl Acad Sci USA. 1994 Dec. 20; 91 (26):12544-8 or in Bioorganic & Medicinal Chemistry Letters Tags for labeling protein N-termini with subtiligase for proteomics Volume 18, Issue 22, 15 Nov. 2008, Pages 6000-6003 Tags for labeling protein N-termini with subtiligase for proteomics Hikari A. I. Yoshihara, Sami Mahrus and James A. Wells).

Alternatively, the peptides may be extended or modified by further conjugation through disulphide bonds. This has the additional advantage of allowing the first and second peptide to dissociate from each other once within the reducing environment of the cell. In this case, the connector compound (eg. TBMB) could be added during the chemical synthesis of the first peptide so as to react with the three cysteine groups; a further cysteine could then be appended to the N-terminus of the first peptide, so that this cysteine only reacted with a free cysteine of the second peptide.

Similar techniques apply equally to the synthesis/coupling of two bicyclic macrocycles.

Furthermore, addition of other drugs may be accomplished in the same manner, using appropriate chemistry, coupling at the N- or C-termini or via side chains. Suitably the coupling is conducted in such a manner that it does not block the activity of either entity.

Thus the invention further relates to a method as described above further comprising the step of extending the polypeptide at one or more of the N-terminus or the C-terminus of the polypeptide.

Thus the invention further relates to a method as described above further comprising the step of conjugating said complex or said polypeptide-connector compound conjugate to a further polypeptide.

Thus the invention further relates to a method as described above wherein said conjugation is performed by
(i) appending a further cysteine to the polypeptide after bonding to the connector compound, and
(ii) conjugating said polypeptide to said further polypeptide via disulphide bonding to said further cysteine.

Genetically Encoded Diversity

The polypeptides of interest are suitably genetically encoded. This offers the advantage of enhanced diversity together with ease of handling. An example of a genetically encoded polypeptide library is a mRNA display library. Another example is a replicable genetic display package (rgdp) library such as a phage display library. Suitably, the polypeptides of interest are genetically encoded as a phage display library.

Thus, suitably the complex of the invention comprises a replicable genetic display package (rgdp) such as a phage particle. In these embodiments, suitably the nucleic acid is comprised by the phage genome. In these embodiments, suitably the polypeptide is comprised by the phage coat.

In some embodiments, the invention may be used to produce a genetically encoded combinatorial library of polypeptides which are generated by translating a number of nucleic acids into corresponding polypeptides and linking molecules of said connector compound to said polypeptides.

The genetically encoded combinatorial library of polypeptides may be generated by phage display, yeast display, ribosome display, bacterial display or mRNA display.

Suitably the genetically encoded combinatorial library of polypeptides is generated by phage display. In phage display embodiments, suitably the polypeptides are displayed on phage according to established techniques such as described below. Most suitably such display is accomplished by fusion of the target polypeptide of interest to an engineered gene permitting external display of the polypeptide of interest; suitably said engineered gene comprises an engineered gene 9 (p9 or gene IX), gene 8 (gene VIII), gene 7 (p7 or gene VII), gene 6 (p6 or gene VI) or gene 3 (p3 or gene III) of the phage. These proteins offer the advantage that they contain fewer or no cysteines that can react with connector compounds such as TBMB and produce side products. For p6, it is advantageous to mutate cysteine 84 to serine. The cysteines in p7 and p9 are most likely buried and therefore may not necessarily need to be mutated to remove them. p8 offers the advantage that it does not contain a cysteine residue. Thus, more suitably said engineered gene comprises an engineered gene 8 (gene VIII), gene 6 (gene VI) or gene 3 (gene III) of the phage.

Most suitably such display is accomplished by fusion of the target polypeptide of interest to an engineered gene 3 protein lacking cysteine residues in domain 1 and 2. This fusion may be accomplished by any suitable technique known in the art such as by manipulation of the nucleic acid encoding the phage gene III protein to change the codons encoding cysteine to codon(s) encoding other amino acid(s), and by inserting a nucleic acid sequence encoding the target polypeptide into the gene III coding sequence in frame so that it is displayed as a gene III fusion protein on the outside of the phage particle.

It is a benefit of the invention that the resulting engineered gene(s) leave the phage infective i.e. capable of infection and propagation. Even when the engineered gene is a gene other than gene 3, (such as gene 6 or gene 8), it may still be desirable to engineer gene 3 to remove one or more of the cysteine residue(s) (such as all of the cysteine residues).

In a preferred embodiment, the genetically encoded polypeptides of the invention are generated by translating a nucleic acid and linking the generated polypeptide to said code. The linkage of phenotype with the genotype allows propagating or decoding the encoded ligand repertoires. Various techniques are available to link the polypeptide to its polynucleotide code. The techniques include phage display, ribosome display, mRNA display, yeast display and bacterial display and others. Encoded polypeptide repertoires comprising up to 10exp13 individual members have been generated with said methods. The number of individual ligands that can be generated according to the invention outperforms clearly the number of individual molecules that are generally assayed in conventional screens.

In a preferred embodiment, phage display technology is used to genetically encode polypeptides of the invention. Phage display is a method in which the gene of a polypeptide is fused to the gene of a phage coat protein. When phage are produced in a bacterial cell, the polypeptide is expressed as a fusion of the coat protein. Upon assembly of a phage particle the polypeptide is displayed on the surface of the phage. By contacting a phage repertoire with an immobilized antigen some phage remain bound to the antigen while others are removed by washing. The phage can be eluted and propagated. The DNA encoding the polypeptide of selected phage can be sequenced. Phage display can be used to encode more than 10exp10 individual polypeptides. A favourable aspect of phage display is that the genetic code, a single stranded DNA is packed in a coat. The coat may protect the DNA from reaction with the molecular core.

In another preferred embodiment, the polypeptide library of the invention is displayed on phage as a gene 3 protein fusion. Each phage particle has about 3 to 5 copies of said phage coat protein. As a result of the display of multiple copies of the modified polypeptide, ligands with micromolar affinities (weak binders) can also be isolated in phage selections. Alternatively, phagemids are used to reduce the number of polypeptides per phage to avoid avidity effects and select ligands with higher affinities.

In another preferred embodiment, phage with modified coat proteins are used for encoding the polypeptide libraries of the invention. In particular, phage lacking or having a reduced number of a specific type of amino acid in coat proteins are used. Using said coat proteins can be advantageous when the molecular core is reactive towards said specific type of amino acid. This is explicitly the case when the functional groups of the displayed polypeptide for cross-linking a molecular core are natural amino acids and the same type of natural amino acid is present at a surface exposed region in the phage coat. Using said phage with modified coat proteins can prevent cross-linking of phage particles through reaction of amino acids of multiple phage with the same molecular core. In addition, using said phage can reduce the cross-linkage of both, amino acid side chains of the functional groups in the polypeptide and of phage coat protein to the same molecular core.

In yet another preferred embodiment, phage with a gene 3 protein lacking the cysteine residues of the disulfide bridges C7-C36, C46-C53, C188-C201 in domain 1 and 2 are used to display polypeptide libraries of the invention. A phage with mutations in said positions (C7C, C36I, C46I, C53V, C188V, C201A) and 14 additional mutations in the gene 3 protein to compensate for the reduced thermal stability (T13I, N15G, R29W, N39K, G55A, T56I, I60V, T101I, Q129H, N138G, L198P, F199L, S207L, D209Y) was generated by Schmidt F. X. and co-workers (Kather, I. et al., J. Mol. Biol., 2005). Phage without thiol groups in said minor coat protein are suited if one or more of the functional amino acids for cross-linking the polypeptide to a molecular core are cysteine residues. Removal of the cysteine residues in the phage coat protein prevents their interference with said bonding reaction between polypeptide and connector compound.

This exemplary phage for application in the invention is now described in more detail.

The disulfide-free phage of F X Schmid (domains D1-D2) comprises fd phage derived from vector fCKCBS (Krebber, C., 1997, J. Mol. Biol.). The vector fCKCBS is based on a fd phage vector that is derived from the American Type Culture Collection (ATCC: 15669-B2).

The amino acid sequence of the domains 1 and 2 of p3 of the wild-type fd phage is publicly available, for example in the PubMed database. For ease of reference, an exemplary sequence is:

```
                                           (SEQ ID No. 13)
AETVESCLAKPHTENSFTNVWKDDKTLDRYANYEGCLWNATGVVVCTGD

ETQCYGTWVPIGLAIPENEGGGSEGGGSEGGGSEGGGTKPPEYGDTPIP

GYTYINPLDGTYPPGTEQNPANPNPSLEESQPLNTFMFQNNRFRNRQGA

LTVYTGTVTQGTDPVKTYYQYTPVSSKAMYDAYWNGKFRDCAFHSGFNE

DPFVCEYQGQSSDLPQPPVNAPSG
```

F X Schmid and co-workers had evolutionarily stabilized the p3 of this phage (Martin, A. and Schmid, F X., 2003, J. Mol. Biol.) by mutating 4 amino acids. In a consecutive work F X Schmid and co-workers had mutated 6 cysteines to eliminate the 3 disulfide-bridges and inserted additional mutations to compensate for the loss of stability (Kather, I. and Schmid F X., 2005, J. Mol. Biol.). In multiple evolutionary cycles they had generated clones 19, 20, 21, and 23 which have all a disulfide-free p3 with varying thermal stabilities.

As explained in more detail in the examples section, the mutant 21 ('clone 21') can be made as described, or simply obtained from F X Schmid and co-workers. According to the publication of F X Schmid this clone contains the following mutations in the domains 1 and 2: C7S, T13I, N15G, R29W, C36I, N39K, C46I, C53V, G55A, T101I, Q129H, C188V, F199L, C201A, D209Y. In addition we found the following mutations in the domains 1 and 2 when we sequenced the clone and compared it to wild-type fd phage: P11S and P198L. Without wishing to be bound by theory it is assumed that these mutations were already present in the phage of vector fCKCBS.

The domains D1 and D2 of clone 21 have the following amino acid sequence:

```
                                           (SEQ ID No. 14)
AETVESSLAKSHIEGSFTNVWKDDKTLDWYANYEGILWKATGVVVITG

DETQVYATWVPIGLAIPENEGGGSEGGGSEGGGSEGGGTKPPEYGDTP

IPGYIYINPLDGTYPPGTEQNPANPNPSLEESHPLNTFMFQNNRFRNR

QGALTVYTGTVTQGTDPVKTYYQYTPVSSKAMYDAYWNGKFRDVAFHS

GFNEDLLVAEYQGQSSYLPQPPVNAPSG
```

The invention also relates to a library generated according to the invention.

The invention may be applied to the screening for molecules or entities binding to (or influencing binding to) a complex of the invention. An example of a complex of the invention is a target polypeptide with a connector compound attached thereto. Any conventional screening format may be adopted by the skilled worker. The particular format used will depend on the goals of the operator. For example, if a high throughput screen is desired then high density, rapid turnaround and simplicity of operation will be paramount. Typically techniques such as phage panning, mRNA display and the like may be equally applied to the present invention as they are applied in the art. The key benefits of the invention are the triple-covalent bonding of the connector compound to the polypeptide of interest and the particular format in which the resulting complexes are screened, (or the use of those complexes as candidate modulators of other interactions or in other screens), is a matter of choice for the person working the invention.

In one embodiment, screening may be performed by contacting a library of the invention with a target ligand and isolating one or more library member(s) that bind to said ligand.

In another embodiment, individual members of said library are contacted with a target ligand in a screen and members of said library that bind to said target ligand are identified.

In another embodiment, members of said library are simultaneously contacted with a target ligand and members of said library that bind to said target ligand are selected.

The target ligand(s) may be a peptide, a protein, a polysaccharide, a lipid, a DNA or an RNA.

The target ligand may be a receptor, a receptor ligand, an enzyme, a hormone or a cytokine.

The target ligand may be a prokaryotic protein, a eukaryotic protein, or an archeal protein. More specifically the target ligand may be a mammalian protein or an insect protein or a bacterial protein or a fungal protein or a viral protein.

The target ligand may be an enzyme, such as a protease. More specifically the target ligand may be an elastase, plasma kallikrein, cathepsin G or urokinase-type plasminogen activator.

It should be noted that the invention also embraces library member(s) isolated from a screen according to the invention. Suitably the screening method(s) of the invention further comprise the step of: manufacturing a quantity of the ligand isolated as capable of binding to the complex of the invention. When the screen is conducted in the opposite format (i.e. when complex(es) of the invention are identified by virtue of their capacity to bind to a provided ligand), suitably the screening method(s) of the invention further comprise the step of: manufacturing a quantity of the complex of the invention isolated as capable of binding to said ligand.

The invention also relates to library members which are, or are capable of being, isolated by a screen according to the present invention, wherein said member is subsequently generated/manufactured without the further use of the nucleic acid which encoded said polypeptide when part of the complex of the invention. For example, the methods of the invention suitable further comprise the additional step of manufacturing a quantity of a polypeptide isolated or identified by a method of the invention by attaching the connector compound to the polypeptide, wherein said polypeptide is recombinantly expressed or chemically synthesized. For example, when the polypeptide is recombinantly synthesised in this embodiment, the nucleic acid originally encoding it as part of a complex of the invention may no longer be directly present but may have been present in an intermediate step eg. PCR amplification or cloning of the original nucleic acid of the complex, leading to production of a template nucleic acid from which the polypeptide may be synthesised in this additional step.

Further Advantages

It is an advantage of the invention that the complexes themselves are capable of propagation. Thus the complexes or libraries of the invention may be grown-selected-(iteratively if desired)-enriched. This contrasts with prior art techniques which require to be deconvoluted after a single round of selection.

The present invention advantageously permits very large libraries to be built and screened.

Suitably the connector compound may be flexible or rigid, more suitably the connector compound is rigid. This has the advantage of greater molecular constraint on the product molecule.

In some embodiments the connector compound not only constrains the molecule by holding it at three or more bonds, but also by acting as a scaffold. Amino acids of the peptide can interact with the scaffold and form a compact structure. This phenomenon may also be found in antibodies where amino acids of the CDR's interact with amino acids of the scaffold. Thus the invention provides this advantageous feature for the first time on conjugated polypeptides such as those comprised by phage particles.

In some embodiments connector compounds with a symmetric geometry are used. This has the advantage that a single product is yielded rather than product mixtures (e.g. isomers).

Synthetic reactions have been established to link a connector compound to a peptide via at least three covalent linkages. Prior art chemical reaction conditions can not readily be applied to genetically encoded peptides. We disclose a set of specific conditions which find application in the conjugation whilst advantageously preserving infectivity.

It is an advantage of the invention that direct readout is obtained, in particular for a peptide+chemical (i.e. peptide+connector compound) combination.

It is an advantage of the invention that a synthetic chemical library is created which is susceptible to propagation. In other words, prior art techniques have created chemical libraries in ways in which it is not possible to amplify/read out the small molecule of interest in this manner i.e. even when nucleic acids have been present in the prior art chemical libraries, it has not been permissive of growth/propagation but has rather only permitted hybridisation or other such techniques.

Similar advantages flow from the techniques described herein such as the chemical conditions used to join the connector compound to the polypeptide which advantageously preserve infectivity of the complex when the complex comprises a phage particle.

Further Applications

The invention also provides a method for generating a genetically encoded combinatorial chemical library comprising polypeptides tethered to a molecular core, the method comprising: (a) generating a genetically encoded library of polypeptides comprising functional groups capable of forming covalent bonds with a molecular core; (b) chemically linking said library to said core by at least three covalent bonds.

In a broad aspect the invention relates to a polypeptide, comprising a connector compound attached to said polypeptide, wherein the connector compound is attached to the polypeptide by at least three discrete covalent bonds. In particular the invention relates to such polypeptides which are obtainable by, or obtained by, methods of the present invention.

The invention may also be applied to the design and/or selection of peptide mimetics or small molecule mimetics for use as drugs or drug targets.

The invention also provides methods for generating genetically encoded combinatorial chemical libraries and for isolating ligands thereof.

The invention may be applied to identification of target hits from DNA sequencing and identifying consensus sequences in the peptides of those target hits, and then synthesising the peptides. For example, a consensus peptide may be designed by this analysis, which consensus peptide may have an amino acid sequence not necessarily identical to any of the hits recovered from the screening phase, and this consensus peptide may then be synthesised according to the present invention.

The complex may comprise a phage particle.

Thus a method is provided for generating genetically encoded combinatorial chemical libraries wherein said libraries comprise polypeptides tethered to a molecular core via at least three covalent bonds. Libraries generated with said method are also provided. Furthermore, a method of contacting said libraries with a target ligand and isolating members that bind to said ligand is provided as are library members generated with said method.

In sharp contrast to the known methods of WO 2004/077062 and WO 2006/078161, the present invention provides methods for the generation and assaying of large libraries of complexes. According to WO 2004/077062 and WO 2004/077062 known methods are provided to produce and screen hundreds, or thousands of compounds. The present invention provides methods to genetically encode compound libraries. This allows to generate and assay millions, billions or more individual compounds.

In contrast to the known methods of WO 2004/077062 and WO 2006/078161, the present invention provides methods to assay large compound libraries in a single reaction compartment by using in vitro selection principles. In contrast to the compounds generated according to WO 2004/077062 and WO 2006/078161, the complexes of the present invention comprise a nucleic acid that allows identification of the isolated complexes; suitably said nucleic acid encodes the polypeptide of the complex.

The present invention provides reaction conditions such as connector compound concentration, reaction time, reaction temperature and the like that spare the nucleic acid of the complex as for example a phage particle, and in particular spare the infectivity of the phage particle. In other words, the chemistry presented herein preserves the function of the nucleic acid of the complex and preserves the biological function of the complex. In the example of the complex comprising a phage particle the chemistry presented herein advantageously enhances preserved functionality of the phage particle and renders it possible or more possible for it to be used in propagation of the nucleic acid after complex formation.

The present invention comprises also genetically encoded combinatorial compound libraries generated with the methods described.

The invention also relates to tricyclic polypeptides joined to a connector compound. These may be created for example by joining the N- and C-termini of a bicyclic polypeptide joined to a connector compound according to the present invention. In this manner, the joined N and C termini create a third loop, making a tricyclic polypeptide. This embodiment is suitably not carried out on phage, but is suitably carried out on a polypeptide-connector compound conjugate of the invention. Joining the N- and C-termini is a matter of routine peptide chemistry. In case any guidance is needed, the C-terminus may be activated and/or the N- and C-termini may be extended for example to add a cysteine to each end and then join them by disulphide bonding. Alternatively the joining may be accomplished by use of a linker region incorporated into the N/C termini. Alternatively the N and C termini may be joined by a conventional peptide bond. Alternatively any other suitable means for joining the N and C termini may be employed, for example N—C-cyclization could be done by standard techniques, for example as disclosed in Linde et al. Peptide Science 90, 671-682 (2008) "Structure-activity relationship and metabolic stability studies of backbone cyclization and N-methylation of melanocortin peptides", or as in Hess et al. J. Med. Chem. 51, 1026-1034 (2008) "backbone cyclic peptidomimetic melanocortin-4 receptor agonist as a novel orally administered drug lead for treating obesity". One advantage of such tricyclic molecules is the avoidance of proteolytic degradation of the free ends, in particular by exoprotease action. Another advantage of a tricyclic polypeptide of this nature is that the third loop may be utilised for generally applicable functions such as BSA binding, cell entry or transportation effects, tagging or any other such use. It will be noted that this third loop will not typically be available for selection (because it is not produced on the phage but only on the polypeptide-connector compound conjugate) and so its use for other such biological functions still advantageously leaves both loops 1 and 2 for selection/creation of specificity. Thus the invention also relates to such tricyclic polypeptides and their manufacture and uses.

The present invention provides further methods for contacting the genetically encoded compound libraries with a target ligand and for identifying ligands binding to said target ligand. The genetically encoded compound libraries are assayed by either screening or selection procedures.

In a screening procedure, individual members of the library are assayed. Multiple copies of an individual member of the library are for example incubated with a target ligand. The target ligand is immobilized before or after contacting the members of the library and unbound members are removed by washing. Bound ligands are for example detected in an enzyme linked immunosorbent assay (ELISA). The amino acid sequences of members of the library that bind to the target ligand are determined by sequencing of the genetic code.

In a selection procedure, multiple members of the encoded compound library are contacted with a target ligand. The target ligand is immobilized before or after contacting the members of the library and unbound members are removed by washing. The genetic code of bound ligands is sequenced. Selected ligands are alternatively propagated to perform further selection rounds.

In one embodiment of the invention, the compound libraries are encoded by phage display and selections are performed by phage panning.

The target ligand of the present invention may be a protein, a DNA, a RNA or a polysaccharide. The protein can be a receptor, an enzyme, a hormone, a cytokine or a viral protein. A possible protein target ligand is a protease wherein said protease can be elastase, plasma kallikrein, cathepsin G or urokinase-type plasminogen activator.

The present invention comprises also members of the encoded combinatorial chemical libraries isolated with methods of the invention. Said members can be produced with or without the genetic code attached. In a preferred embodiment, said members lacking the nucleic acid are used as drug or drug lead.

Several members of the encoded combinatorial chemical libraries that are capable of binding to a target ligand were isolated with a method of the present invention. Said members are composed of a mesitylene core and a polypeptide with the sequence $AC(X)_6C(X)_6CG$ (SEQ ID No. 6), wherein the polypeptide is tethered to the exo-cyclic methyl groups of the core via the cysteine residues forming three thioether bonds and wherein X stands for a natural amino acid, A for alanine, C for cysteine and G for glycine. The peptide portion of said members can be expressed recombinantly or be synthesized chemically.

The present invention provides inhibitors of human plasma kallikrein isolated with methods of the invention from encoded combinatorial chemical libraries of the invention. Said inhibitors have either of the polypeptide sequences GCSDRFRNCPADEALCG (SEQ ID No. 7), ACSDRFRNCPLWSGTCG (SEQ ID No. 1), ACSTERRYCPIEIFPCG (SEQ ID No. 2), ACAPWRTACYEDLMWCG (SEQ ID No. 3), ACGTGEGRCRVNWTPCG (SEQ ID No. 4) or related sequences wherein the thiol groups of the cysteines are linked to mesitylene cores.

The present invention provides also inhibitors of human cathepsin G isolated with methods of the invention form encoded combinatorial chemical libraries of the invention. Said inhibitors have either of the polypeptide sequences ACEYGDLWCGWDPPVCG (SEQ ID No. 8), ACIFDLGFCHNDWWNCG (SEQ ID No. 9), ACLRAQEDCVYDRGFCG (SEQ ID No. 10) or related sequences wherein the thiol groups of the cysteines are linked to mesitylene cores.

The present invention provides also inhibitors of human urokinase-type plasminogen activator isolated with methods of the invention form encoded combinatorial chemical libraries of the invention. Said inhibitors have either of the polypeptide sequences ACNSRFSGCQIDLLMCG (SEQ ID No. 11), ACSRYEVDCRGRGSACG (SEQ ID No. 12) or related sequences wherein the thiol groups of the cysteines are linked to mesitylene cores.

Biological Targets

It is important to create and assay as many molecules as possible since the chance to identify a ligand with desired properties increases when more molecules are tested. Also, in general, ligands with higher affinities are obtained when larger molecule repertoires are assayed.

Researchers typically evaluate molecules using screening or selection methodologies. Screening is a process by which compounds are individually assayed for their ability to modify a target. Screening processes are versatile and allow the assaying of molecule repertoires having a manifold of structures. Screening by individual assays, however, may be time-consuming and the number of unique molecules that can be tested for binding to a specific target generally does not exceed 10exp6 chemical entities. In contrast, selection methods generally allow the sampling of a much larger number of different molecules. Thus selection methods are more suitably used in application of the invention. In selection procedures, molecules are assayed in a single reaction vessel and the ones with favourable properties (i.e. binding) are physically separated from inactive molecules.

Selection strategies are available that allow to generate and assay simultaneously more than 10exp13 individual compounds. Examples for powerful affinity selection techniques are phage display, ribosome display, mRNA display, yeast display, bacterial display or RNA/DNA aptamer methods. These biological in vitro selection methods have in common that ligand repertoires are encoded by DNA or RNA. They allow the propagation and the identification of selected ligands by sequencing. Phage display technology has for example been used for the isolation of antibodies with very high binding affinities to virtually any target.

INDUSTRIAL APPLICATION

The present invention is applicable to the discovery of molecules that are useful in the fields of biology, biotechnology and pharmaceutical sciences. In particular the present invention relates to methods for the generation of drugs or drug leads.

The present invention comprises methods for the generation of genetically encoded combinatorial chemical libraries and methods for the isolation of members of said libraries. Furthermore, the invention comprises libraries generated with said methods and members of the libraries isolated with said methods.

The present invention provides a method for the generation of genetically encoded combinatorial chemical libraries wherein the members of said libraries comprise a central molecular core and multiple diversity elements that are appended to said core. Said genetically encoded libraries are generated in two steps: In the first step, genetically encoded polypeptide libraries comprising functional groups capable of forming covalent bonds with a molecular core are generated. In the second step, the genetically encoded polypeptide libraries are chemically cross-linked to said molecular core by at least three covalent bonds.

Molecules of the genetically encoded combinatorial chemical libraries of the present invention have a core structure that is expanded by various appendages. Unlike state of the art genetically encoded combinatorial chemical libraries generated with biological methods, the libraries of the present invention provide molecules with non-linear, branched architectures. Molecules with such branched structures are suitable for binding to target ligands since they can bind to the target through interaction of multiple appendages that point away from a central core.

In contrast to linear polymeric structures, the complexes of the present invention have less conformational flexibility. In solution they adopt only a limited set of conformations. As a consequence, binding of said complexes or polypeptides to a target ligand is not associated with a dramatic loss of entropy and high binding affinities can result.

The polypeptides of the complexes/libraries of the invention are genetically encoded. This allows very powerful biological encoding methods as for example phage display, ribosome display, yeast display, bacterial display or mRNA display can be applied for their production which allows to generate ligand libraries containing millions, billions or more individual members.

The sequences of the polypeptide appendages of members of the genetically encoded combinatorial chemical libraries can be varied. Exceptions are amino acids that harbour functional groups for cross-linking the polypeptide to a molecular core, which is explained in more detail herein. The polypeptide appendages can comprise very large combinatorial diversities. Representing large combinatorial repertoires is important since the probability of isolating high-affinity binders to target ligands increases with library size.

Unlike linear biopolymers as polypeptides, DNA or RNA aptamers, the complexes and members of the genetically encoded combinatorial chemical libraries of the invention do not form complex tertiary structures. The complexes and members of the genetically encoded combinatorial chemical libraries of the invention enjoy greatly reduced risk of inactivation through irreversible unfolding. The formation of aggregates due to unfolding is thus advantageously unlikely.

The genetically encoded libraries of the invention suitably comprise at least 10exp5 individual members. Preferentially, said libraries comprise millions or billions or more of individual members. The size of said libraries is determined by the methods that are used to link the nucleic acid encoding a polypeptide with that polypeptide. In a preferred embodiment of the invention, biological methods are used to generate genetically encoded polypeptide repertoires. The number of individual members of polypeptides that are linked to the encoding polynucleotide code may exceed 10exp13 depending on the methods used.

EXAMPLES

Overview

In these examples we demonstrate manufacture of phage encoded combinatorial chemical libraries.

The discovery of synthetic molecules with high affinity and specificity for biological targets is a central problem in drug discovery. While it became recently possible to isolate large molecular structures as antibodies or aptamers to virtually any target using in vitro selection techniques, the generation of small organic binders with high affinities remained a great challenge. In this invention, we disclose a strategy for the isolation of small molecule structures that are built of an organic molecule core (connector compound) that is decorated with peptidic moieties (e.g. polypeptide(s)). For convenience in these examples, phage display technology was used to encode the peptide fraction of the small molecules allowing the generation and selection of very large combinatorial chemical repertoires. Reaction conditions were chosen to selectively tether a 17 amino acid peptide via three thioether bonds to a benzene molecule but spare the coat proteins of the phage particles. Highly specific binders with sub-micromolar affinities were obtained against the two human serine proteases plasma kallikrein and cathepsin G. An affinity maturated inhibitor of human plasma kallikrein with an apparent $K_i$ of 1.5 nM efficiently suppressed contact activation in human plasma.

Background to the Examples

Molecules with high affinity and specificity for biological targets are needed to develop efficient and selective therapies against a wide range of diseases. The process of finding a new small organic molecule drug against a chosen target usually involves high-throughput screening, wherein large libraries of chemicals are tested for their ability to modify the target. The process, however, is time-consuming and costly and the number of unique molecules that can be tested against a specific target generally does not exceed a million chemical entities. The screens often only provide leads, which then require further improvement either by empirical methods or by chemical design. More powerful methods for the generation of binding molecules are biological in vitro selection techniques as phage display, ribosome display, mRNA display or RNA/DNA aptamer techniques. They allow the rapid generation of large combinatorial repertoires ($10^9$-$10^{13}$) of polypeptides, RNA or DNA and the subsequent isolation of binders with high affinities. However, the restriction of such methods to large biopolymer structures as antibodies or aptamers precludes their use for small-molecule discovery.

In order to apply in vitro selection to combinatorial chemistry libraries, various methodologies have been proposed to associate organic molecules with a tag that specifies its structure. Most approaches proposed the use of DNA tags to identify the small organic molecules after affinity selection. A process of parallel combinatorial synthesis to encode individual members of a large library of chemicals with unique nucleotide sequences on beads has been proposed (Brenner, S. and Lerner, R. A., PNAS, 1992). After the chemical entity is bound to the target, the genetic code is decoded by sequencing of the nucleotide tag. A small collection of organic molecules has been conjugated to DNA oligonucleotides and performed affinity selections with different antigens (Doyon, J. B. et al., JACS, 2003). Neri D. and co-workers had generated large repertoires of molecule pairs by self-assembly of smaller DNA encoded chemical sub-libraries through hybridization of two DNA strands (Melkko, S. et al., Nature Biotechnol., 2004). The methodology was successfully used for affinity maturation of small molecule ligands. Halpin D. R. and Harris P. B. developed a strategy for the in vitro evolution of combinatorial chemical libraries that involves amplification of selected compounds to perform multiple selection rounds (Halpin, D. R. and Harbury, P. B., PLOS Biology, 2004). Woiwode T. F. et al. attached libraries of synthetic compounds to coat proteins of bacteriophage particles such that the identity of the chemical structure is encoded in the genome of the phage (Woiwode, T. F., Chem. & Biol., 2003). All these strategies employing DNA encoded chemical compounds have proven to be efficient in model experiments and some have even yielded novel small molecule binders. However, it became apparent that the encoding of large compound libraries and the amplification of selected compounds is much more demanding than the equivalent procedures in biological selection systems.

In this invention we teach a strategy for encoding hybrid peptide-small molecule structures that are built of multiple polypeptide fragments tethered to a central small organic molecule. The peptide portion is encoded by phage particles allowing the generation and selection of very large and complex diversities. We envisioned the following reaction procedures to link peptide fragments to a small molecule (schematically depicted in FIG. 1). A chemical structure equipped with reactive groups is incubated with a phage displayed peptide. Specific amino acids in the peptide (e.g. cysteines) react with the functional groups of the small molecule to form covalent bonds wherein a first linkage accelerates consecutive linkages. The resulting molecules are then subjected to affinity selections. Alternatively, specific peptide bonds of the multi-cyclic structure are enzymatically cleaved to obtain small chemical structures decorated with discrete peptide entities. The attachment of phage displayed polypeptide repertoires to small molecular structures is not trivial as the reaction needs to be specific and selective to yield a single product. Also, the reactants suitably should not impair the phage particle. Furthermore, linking a small molecule via multiple sites to a peptide adds an additional level of complexity as product mixtures could easily be generated or phage particles could be cross-linked. In fact no example is known in the art where a small molecule was linked to a polypeptide displayed on phage via more than one bond.

Materials and Methods

Chemical Linkage of Peptide-D12 Fusion Proteins to a Chemical Scaffold

The domains D1-D2 of the g3p (comprising amino acid residues 2 to 217 of the mature fd-g3p) with and without the N-terminally fused peptide $^N$ACGSGCGSGCG$^C$ (SEQ ID No. 16) was expressed in *E. coli*. The pUC119 based expression vector with a leader sequence and the D1-D2 gene with a C-terminal hexa-histidine tag (here termed pUC119H6D12) was kindly provided by Phil Holliger from the laboratory of molecular biology (LMB) in Cambridge. A plasmid for expression of D1-D2 with the N-terminal peptide was cloned by PCR amplification of the D1-D2 gene with the primers pepd12ba (encoding the peptide sequence) and d12fo and ligation into the SfiI/NotI digested pUC119H6D12. The gene for expression of disulfide-free D1-D2 with a total of 20 amino acid mutations was kindly provided by Insa Kather and Franz Xaver Schmid from the University of Bayreuth. The gene was PCR amplified from the vector fdg3p0ss21 with either the primer pair d120ssba/d120ssfo, pepd120ssba/d120ssfo, P2cd120ssba/d120ssfo or P1cd120ssba/d120ssfo and SfiI/NotI ligated into pUC119H6D12 for expression of disulfide-free D1-D2 with and without the N-terminal fused peptides $^N$ACGSGCGS-GCG$^C$ (SEQ ID No. 16), $^N$AGSGCGSGCG$^C$ (SEQ ID No. 17) or $^N$AGSGKGSGCG$^C$ (SEQ ID No. 18). All 6 proteins were expressed in TG1 *E. coli* cells at 30° C. for 8 hours and the periplasmic fraction was purified stepwise by Ni-affinity chromatography and gel filtration on a Superdex 75 column in 20 mM NH$_4$HCO$_3$ pH 7.4.

Oxidized sulfhydryl groups were reduced by incubation of the protein (1-10 μM) with 1 mM TCEP in 20 mM NH$_4$HCO$_3$, pH 8 at 42° C. for 1 hr. The reducing agent was removed on a vivaspin 20 filter having a MWCO of 10'000 (Vivascience, Stonehouse, UK) using 20 mM NH$_4$HCO$_3$, 5 mM EDTA, pH 8 buffer. The thiol groups of the proteins were reacted by incubation with 10 μM TBMB in reaction buffer (20 mM NH$_4$HCO$_3$, 5 mM EDTA, pH 8, 20% ACN) at 30° C. for 1 hr. For removal of non-reacted TBMB and concentration the protein was filtered with a microcon YM-30 (Millipore, Bedford, Mass.). The molecular masses of the proteins (5-20 M) were determined by denaturing in 4 volumes of 50% MeOH, 1% formic acid and analysis on a time of flight mass spectrometer with electrospray ionization (Micromass, Milford, Mass., USA). Molecular masses were obtained by deconvoluting multiply charged protein mass spectra using MassLynx version 4.1. The performance of the chemical modification reaction in presence of phage was tested by addition of PEG purified phage to a final concentration of 10$^{10}$ t.u. to the protein before TCEP reduction. The phage was removed by gel filtration with a PD-10 column (Amersham Pharmacia, Uppsala, Sweden) after TBMB reaction.

Creation of a Phage Peptide Library

The genes encoding a semi-random peptide with the sequence Ala-Cys-(Xaa)$_6$-Cys-(Xaa)$_6$-Cys (SEQ ID No. 19), the linker Gly-Gly-Ser-Gly (SEQ ID No. 20) and the two disulfide-free domains D1 and D2 were cloned in the correct orientation into the phage vector fd0D$_{12}$ to obtain phage library 1. The vector fd0D$_{12}$, lacking the genes of the D1 and D2 domains of gene 3 and having a second SfiI restriction site was previously created by whole-plasmid PCR amplification of fdg3p0ss21 (Kather, I. et al., J. Mol. Biol., 2005) using the primer ecoG3pNba and pelbsfiecofo. The genes encoding the peptide repertoire and the two gene 3 domains were step-wise created in two consecutive PCR reactions. First, the genes of D1 and D2 were PCR amplified with the two primer prepcr and sfi2fo using the vector fdg3p0ss21 as a template. Second, the DNA encoding the random peptides was appended in a PCR reaction using the primer sficx6ba and sfi2fo. The ligation of 33 and 9 μg of SfiI digested fd0D$_{12}$ plasmid and PCR product yielded 4.4×10$^9$ colonies on 12 20×20 cm chloramphenicol (30 μg/ml) 2YT plates. Colonies were scraped off the plates with 2YT media, supplemented with 15% glycerol and stored at −80° C. Glycerol stocks were diluted to OD$_{600}$=0.1 in 1 liter 2YT/chloramphenicol (30 μg/ml) cultures and phage were expressed at 30° C. over night (12 to 16 hrs).

Chemical Linkage of a Phage Displayed Peptide to a Small Molecule

Typically 10$^{11}$-10$^{12}$ t.u. of PEG purified phage were reduced in 20 ml of 20 mM NH$_4$HCO$_3$, pH 8 with 1 mM TCEP at 42° C. for 1 hr. The phage were spun at 4000 rpm in a vivaspin-20 filter (MWCO of 10'000) to reduce the volume to 1 ml and washed twice with 10 ml ice cold reaction buffer (20 mM NH$_4$HCO$_3$, 5 mM EDTA, pH 8). The volume of the reduced phage was adjusted to 32 ml with reaction buffer and 8 ml of 50 μM TBMB in ACN were added to obtain a final concentration of 10 μM. The reaction was incubated at 30° C. for 1 hr before non-reacted TBMB was removed by precipitation of the phage with ⅕ volume of 20% PEG, 2.5 M NaCl on ice and centrifugation at 4000 rpm for 30 minutes.

Phage Selections with Human Plasma Kallikrein and Cathepsin G

Human plasma kallikrein (activated with factor XIIa) was purchased from Innovative Research (Southfiled, Mich., USA) and biotinylated at a concentration of 1.2 μM with a 5-fold molar excess of Sulfo-NHS-LC-biotin (Pierce, Rockford, Ill., USA) in PBS, pH 7.4/5% DMSO at RT for 1 hr. The biotinylated protein was purified on a PD-10 column using a buffer of 50 mM NaAc, pH 5.5, 200 mM NaCl. Readily biotinylated human cathepsin G was purchased from Lee Biosolutions (St. Louis, Mich., USA). Biotinylated antigens (5 to 20 μg) were incubated with 50 μl magnetic steptavidin beads (Dynal, M-280 from Invitrogen, Paisley, UK) for 20 minutes at 4° C. The antigen-coated beads were washed twice with washing buffer (10 mM Tris-Cl, pH 7.4, 150 mM NaCl, 10 mM MgCl$_2$, 1 mM CaCl$_2$) and blocked in 0.5 ml washing buffer containing 1% BSA and 0.1% tween 20 for 30 minutes. The chemically modified phage (typically 10$^{10}$-10$^{11}$ t.u. dissolved in 2 ml washing buffer) were blocked by addition of 1 ml of washing buffer containing 3% BSA and 0.3% tween 20. 3 ml blocked phage were pipetted to 0.5 ml blocked magnetic beads and incubated on a rotating wheel at RT. The beads were washed 8 times with washing buffer containing 0.1% tween 20 and twice with washing buffer before incubation with 100 μl of 50 μM glycine, pH 2.2 for 5 minutes. Eluted phage were transferred to 50 μl of 1 M Tris-Cl, pH 8 for neutralization, incubated with 50 ml TG1 cells at OD$_{600}$=0.4 for 90 minutes at 37° C. and the cells were plated on large 2YT/chloramphenicol plates. Two additional rounds of panning were performed using the same procedures. In the second round of selection, neutravidin-coated magnetic beads were used to prevent the enrichment of streptavidin-specific peptides. The neutravidin beads were prepared by reacting 0.8 mg neutravidin (Pierce, Rockford, Ill., USA) with 0.5 ml tosyl-activated magnetic beads (Dynal, M-280 from Invitrogen, Paisley, UK) according to the supplier's instructions.

Screening Procedure to Identify Protease Inhibitors

The plasmid DNA of clones selected after the second and third rounds of biopanning was PCR-amplified in a single tube with the primer 21seqba and flagfo and cloned into the vector pUC119H6D12 at the SfiI and NotI sites for the periplasmic expression of the peptides fused to the disulfide-free D1 and D2 domains with a C-terminal FLAG tag and a hexa-histidine-tag. The ligated plasmids were electroporated into TG1 cells and plated on 2YT/ampicillin (100 μg/ml) plates. Clones expressing the recombinant protein were identified as follows: 1 ml cultures of 2YT/ampicillin (100 μg/ml) in 96-deep well plates were inoculated with cells of individual colonies and incubated at 37° C. Protein expression was induced with 1 mM IPTG when the cultures were turbid and the plates were shaken 300 rpm at 30° C. o/n. The cells were pelleted by centrifugation at 3500 rpm for 30 minutes, lysed with washing buffer containing 1 mg/ml lysozyme and spun at 3500 rpm to pellet the cell debris. The supernatants were transferred to 96-well polysorp plates (Nunc, Roskilde, Denmark) for non-specific adsorption. The wells were rinsed twice with washing buffer containing 0.1% tween 20 and blocked with washing buffer containing 1% BSA and 0.1% tween 20 for 1 hr. Anti-FLAG M2-peroxidase conjugate (Sigma-Aldrich, St. Louis, Mo., USA) was 1:5000 diluted and blocked in washing buffer containing 1% BSA and 0.1% tween 20 and added to the plates for 1 hr. The wells were washed (5 times with washing buffer containing 0.1% tween 20 and once without detergent) and the bound peroxidase was detected with TMB substrate solution (eBiosciences, San Diego, USA). The plasmid DNA of protein expressing clones was sequenced (Geneservice, Cambridge, UK). Selected clones were expressed on an 800 ml scale and purified by Ni-affinity chromatography and gel filtration as described above. The peptides were chemically modified using the procedure described above and the concentrations of the products were determined by measuring the optical absorption at 280 nm. The IC$_{50}$ was measured by incubating various concentrations of the modified peptide fusion proteins (2-fold dilutions) with human plasma kallikrein (0.1 nM) or cathepsin G (20 nM) and determining the residual activity in 10 mM Tris-Cl, pH 7.4, 150 mM NaCl, 10 mM MgCl$_2$, 1 mM CaCl$_2$, 0.1% BSA, 0.01% triton-X100. Human plasma kallikrein activity was measured with the fluorogenic substrate Z-Phe-Arg-AMC (Bachem, Bubendorf, Switzerland) at a concentration of 100 µM on a Spectramax Gemini fluorescence plate reader (excitation at 355 nm, emission recording at 460 nm; Molecular Devices, Sunnyvale, Calif., USA). Human cathepsin G activity was measured with the colorimetric substrate N-Suc-Ala-Ala-Phe-Pro-(SEQ ID No. 21) pNA (Bachem, Bubendorf, Switzerland) at a concentration of 1 mM with a Spectramax absorption plate reader (recording at 410 nm; Molecular Devices, Sunnyvale, Calif., USA).

Phage Selections for Affinity Maturation of Human Plasma Kallikrein Inhibitors

Three peptide phage libraries were created essentially as the library 1 (see above) but using the degenerate primer sficx6abc (library 2), sficx6abb (library 3) and sficx6aba (library 4) instead of sficx6ba. Electroporation of the ligation reactions into TG1 cells yielded 9.5×10$^8$ (library 2), 1.1×10$^9$ (library 3) and 1.2×10$^9$ (library 4) transformants. Phage of each library were produced in 1 L cultures, purified, pooled and reacted with TBMB. Three rounds of panning were performed essentially as in the selections described above but using the biotinylated human plasma kallikrein at a lower concentration (1 nM in the 1$^{st}$ and 2$^{nd}$ rounds, 200 µM in the 3$^{rd}$ round).

Chemical Synthesis of Bicyclic Peptides

Peptides with a free amine at the N-terminus and an amide at the C-terminus were chemically synthesized on a 25 mg scale by solid phase chemistry (JPT Peptide Technologies, Berlin, Germany). The crude peptides in 1 ml 60% NH$_4$HCO$_3$, pH 8 and 30% ACN (1 mM) were reacted with TBMB (1.2 mM) for 1 hr at RT. The reaction product was purified by reversed-phase high-performance liquid chromatographic (HPLC) using a C18 column and gradient elution with a mobile phase composed of ACN and 0.1% aqueous trifluoroacetic acid (TFA) solution at a flow rate of 2 ml/min. The purified peptides were freeze-dried and dissolved in DMSO or a buffer of 50 mM Tris-Cl pH 7.8, 150 mM NaCl for activity measurements.

Activity and Specificity Measurement of Human Plasma Kallikrein Inhibitors

Inhibitory activities (IC$_{50}$) were determined by measuring residual activities of the enzyme upon incubation (30 min, RT) with different concentrations of inhibitor (typically ranging from 10 µM to 0.5 µM). The activities of human plasma kallikrein (0.1 nM) and factor XIa (0.8 nM; Innovative Research, Southfiled, Mich., USA) were measured with Z-Phe-Arg-AMC (100 µM) and the activity of human thrombin (2 nM; Innovative Research, Southfiled, Mich., USA) with Boc-Phe-Ser-Arg-AMC (100 µM) in 10 mM Tris-Cl, pH 7.4, 150 mM NaCl, 10 mM MgCl$_2$, 1 mM CaCl$_2$, 0.1% BSA, 0.01% triton X-100 and 5% DMSO. Recombinant mouse plasma kallikrein from R&D Systems (Minneapolis, Minn., USA) with a signal peptide was proteolytically activated with 0.5 mg/ml thermolysin at 37° C. for 1 hr. The activity of mouse plasma kallikrein (3 nM) was measured with Z-Phe-Arg-AMC (100 µM) in 50 mM Tris-Cl pH 7.5, 10 mM CaCl$_2$ and 250 mM NaCl, 0.1% BSA, 0.01% triton X-100 and 5% DMSO. Inhibitor hydrolysed in one binding loop was generated by incubation of TBMB modified peptide PK15 with human plasma kallikrein at a molar ration of 5:1 for 24 hours at 37° C. and subsequent heat inactivation of the enzyme at 60° C. (30 min). Apparent K$_i$ values were calculated according to the Cheng and Prusoff equation (Cheng, Y. and Prusoff, W. H., Biochem. Pharmacol., 1973).

Measurement of Contact Activation in Human Plasma

Normal human plasma from single donors was purchased from 3H Biomedical (Uppsala, Sweden). The plasma was centrifuged at 1500×g at 20° C. for 15 minutes to obtain platelet-poor plasma (PPP). Aliquots of the PPP were stored in polypropylene tubes at −80° C. Samples of 60 µl PPP containing 5, 50, 500 or 5000 nM of aprotinin (Roche, Mannheim, Germany) or TBMB modified peptide PK15 were prepared. The thrombin activation time was measured at 37° C. by addition of 20 µl of 1:10 diluted actin FS (Dade Behring, Marburg, Germany) and 20 µl of 20 mM hepes buffer pH 7.4, 100 mM CaCl$_2$, 50 mg/ml BSA and 1 mM Z-Gly-Gly-Arg (SEQ ID No. 22)-AMC to the plasma sample and monitoring of the fluorescence intensity with a fluorescence plate reader (excitation at 355 nm, emission recording at 460 nm; PHERAStar, Labtech, Offenburg, Germany). Activation of factor XIIa and human plasma kallikrein were measured as follows. 2 µg kaolin was added to the plasma samples, mixed well and incubated for 20 minutes at 37° C. The samples were diluted 250-fold in 50 mM Tris-Cl pH 7.8, 150 mM NaCl. Plasma kallikrein-like activity was measured with the chromogenic substrate H-D-Pro-Phe-Arg-pNA (100 µM; Bachem, Bubendorf, Switzerland) using an absorption plate reader (absorption at 450 nm; Molecular Devices, Sunnyvale, Calif., USA).

Structure Determination of TBMB Modified Peptide PK15

1 mg of TBMB modified peptide PK15 was dissolved in 550 µl 10 mM deuterated Tris HCl pH 6.6, 150 mM NaCl, 10 mM MgCl$_2$, 1 mM CaCl$_2$ to obtain an inhibitor concentration of 1 mM. Spectra of the inhibitor were recorded at 800 MHz (Bruker Avance with TCI cryoprobe). Spectral assignments were based on TOCSY and NOESY spectra. Distance restraints were from the NOESY spectra. 50 structure conformers were calculated. The program PyMOL was used for structure analysis and visualization of the molecular models.

Example 1

Making a Complex

In this example we demonstrate attaching phage displayed peptides to small molecules. The polypeptide in this example is a phage displayed peptide. The nucleic acid is comprised by the phage particle. The connector compound of this example is a small molecule (TBMB in this example).

We used the small organic compound tris-(bromomethyl) benzene (TBMB) as a scaffold to anchor peptides containing three cysteine residues (Kemp, D. S, and McNamara, P. E., J. Org. Chem., 1985; FIG. 1B). Halogene alkanes conjugated to an aromatic scaffold react specifically with thiol groups of cysteines in aqueous solvent at room temperature (Stefanova, H. I., Biochemistry, 1993). Meloen and coworkers had previously used bromomethyl-substituted synthetic scaffolds for the immobilization of peptides with multiple cysteines (Timmerman, P. et al., ChemBioChem, 2005). The mild conditions needed for the substitution reaction are convenient to spare the functionality of the phage (Olofsson, L., et al., J. of Molecular Recognition, 1998). We chose cysteines as anchoring points because their side chains have the most distinguished reactivity within the 20 natural amino acids. Also, cysteine residues are rare in proteins of the phage coat (8 cysteines in pill, one cysteine in pVI, pVII and pIX; Petrenko, V. A. and Smith, G. P., Phage Display in Biotechnology and Drug Discovery, 2005). The three-fold rotational symmetry of the TBMB molecule ensures the formation of a unique structural and spatial isomer upon reaction with three cysteines in a peptide.

Figure 2A:
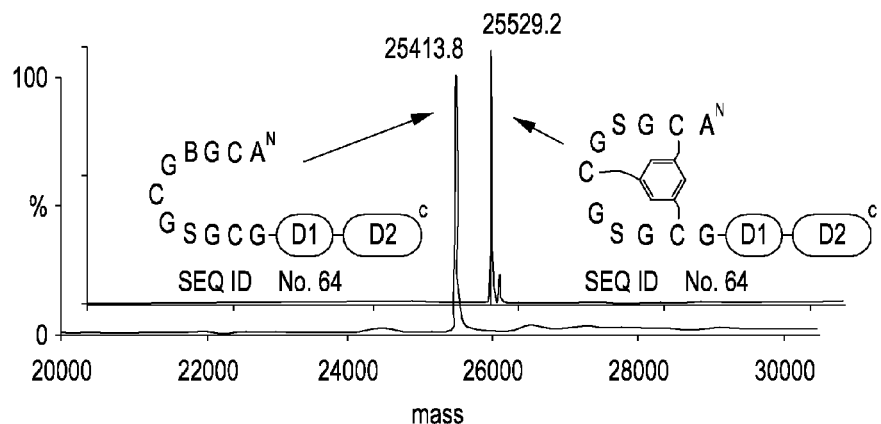
FIG. 2A: Molecular mass of the GCGSGCGSGCG (SEQ ID No. 15)-D1-D2 fusion protein before and after reaction with 10 μM TBMB in 20 mM $NH_4HCO_3$, 5 mM EDTA, pH 8, 20% ACN at 30° C. for 1 hour determined by mass spectrometry. The mass difference of the reacted and non-reacted peptide fusion protein corresponds to the mass of the small molecule core mesitylene.
Figure 7A:
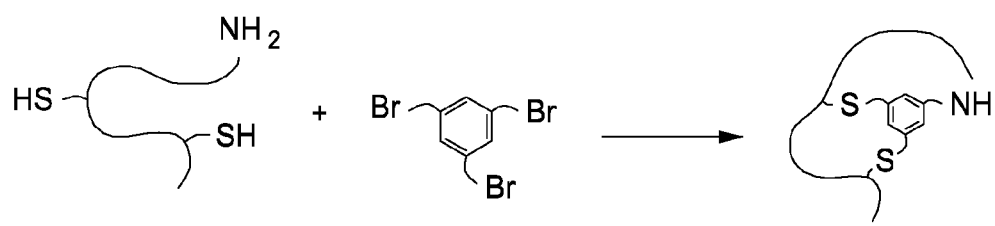
FIG. 7A: Plausible reaction mechanism of TBMB with a peptide fusion protein containing two cysteine residues.
Figure 7B:
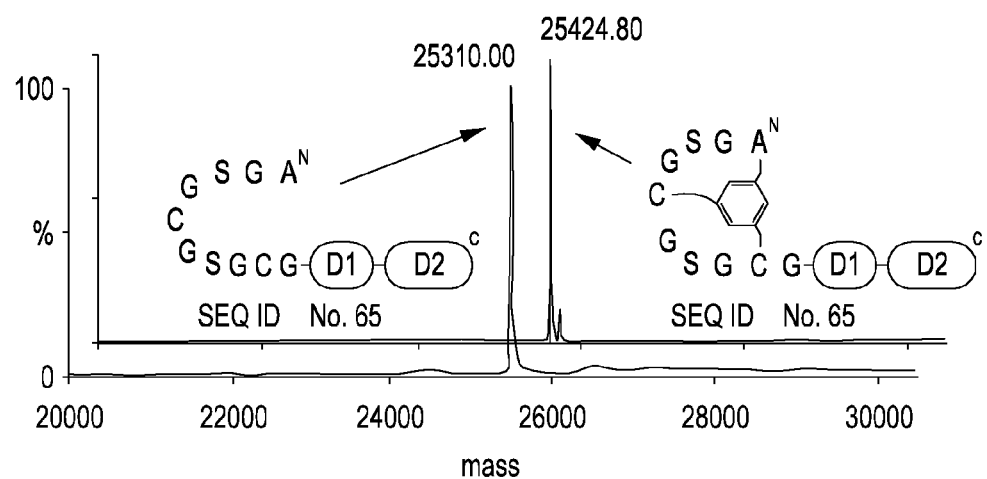
FIG. 7B: Mass spectra of a peptide fusion proteins with two cysteines before and after reaction with TBMB.
Figure 7C:
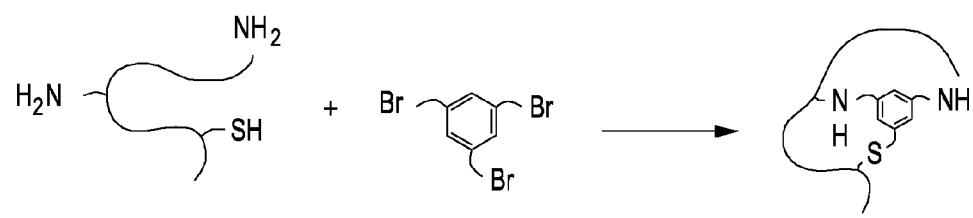
FIG. 7C: Plausible reaction mechanism of TBMB with a peptide fusion protein containing one cysteine residue.
Figure 7D:
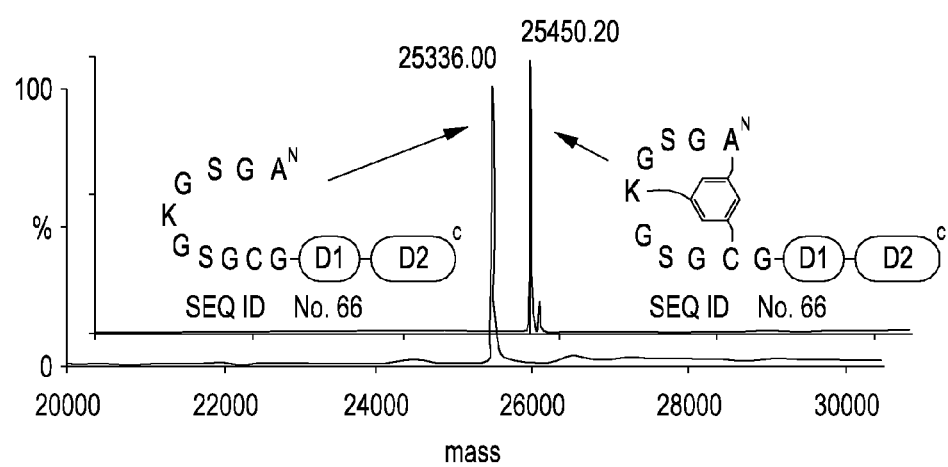
FIG. 7D: Mass spectra of a peptide fusion proteins with one cysteine before and after reaction with TBMB.

The reaction conditions for the modification of a peptide on phage were elaborated next. As it appeared difficult to detect the chemically modified peptide on phage with available techniques, we expressed the peptide $^N$G$^C$GSG$\underline{C}$GSG $\underline{C}$G$^C$ (SEQ ID No. 15) as an N-terminal fusion with the two soluble domains D1 and D2 of the minor phage coat protein pIII and analyzed the molecular weight of the protein before and after reaction with TBMB by mass spectrometry. Attempts to selectively link the three cysteines in the peptide to the scaffold but spare the three disulfide bridges of the D1 and D2 domains of pIII (C7-C36, C46-C53, C188-C201) failed. This prompted us to take advantage of a disulfide-free gene-3-protein recently developed by Schmidt F. X. and co-workers (Kather, I. et al., J. Mol. Biol., 2005). The peptide fused to the N-terminal domain of the cysteine-free gIII protein was reduced with tris(carboxyethyl)phosphine (TCEP). As the reducing agent was found to react with the bromomethyl groups of the TBMB scaffold, it was removed before the addition of TBMB to the protein. Re-oxidation of the thiol groups after removal of TCEP could be prevented by degassing of the reaction buffer and complexation of metal ions with 5 mM EDTA. Reaction of the thiol groups with TBMB at various concentrations and mass spectrometric analysis of the product revealed that a concentration of 10 µM TBMB is sufficient for quantitative modification of the peptide at 30° C. in one hour. Predominantly one product was formed with the expected molecular mass (Δ mass expected=114 Da; FIG. 2A). When the disulfide-free D1-D2 without a fused peptide was incubated with TBMB, its mass was not changed indicating that non-specific reactions with other amino acids do not occur. Addition of phage particles to the reactions ($10^{10}$ t.u. per milliliter) revealed that the high density of phage coat proteins in the vessel does not encumber the reaction of the peptide with TBMB. Unexpectedly, we found that reaction of TBMB with peptides containing only two cysteine residues ($^N$AGSG$\underline{C}$GSG$\underline{C}$GC(SEQ ID No. 17)-D1-D2) yields a product with a molecular mass that is consistent with the reaction of the remaining bromomethyl group with the primary amine of the N-terminus (FIGS. 7A and 7B). Similarly, the reaction of TBMB with a peptide having one cysteine and a lysine ($^N$AGSGKGSG$\underline{C}$G$^C$(SEQ ID No. 18)-D1-D2) yields a molecular mass that is expected when the primary amines of lysine and the N-terminus react with the remaining two bromomethyl groups (FIGS. 7C and 7D).

Figure 2B:
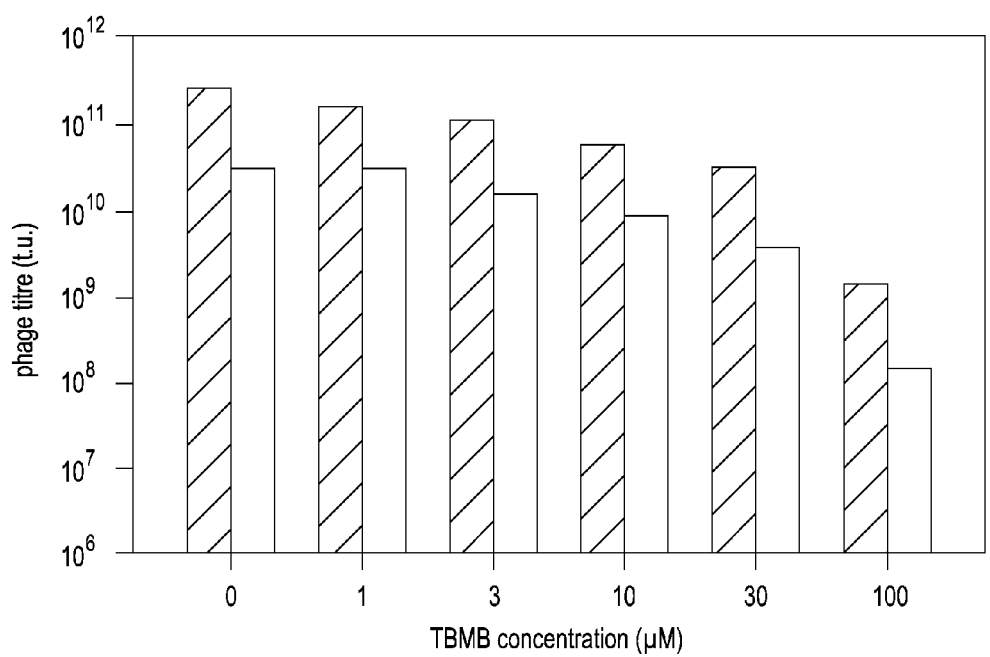
FIG. 2B: Titres (transducing units) of phage reduced and treated with various concentrations of TBMB in 20 mM $NH_4HCO_3$, 5 mM EDTA, pH 8, 20% ACN at 30° C. for 1 hour. Titres of phage from fdg3p0ss21 (black) and from library 1 (white) are shown.

Next, we tested whether phage modified with TBMB were still able to infect bacteria. We found that the higher the TBMB concentration in the reaction was, the fewer phage remained infective (FIG. 2B). At reaction conditions that allow the quantitative modification of the peptide (10 µM TBMB, 30° C., reaction for 1 hour) the number of infective phage dropped by a factor 5.

Example 2

Screening

This example shows affinity selection of inhibitors for human plasma kallikrein and cathepsin G.

The feasibility of selecting phage encoded peptide-small molecule hybrid structures was put to the test using the two human antigens plasma kallikrein and cathespin G. A library of phage displaying peptides on the minor coat protein pIII with a complexity of 4.4×10$^9$ variants was created. The peptides were designed to have two sequences of six random amino acids flanked by three cysteines (Cys-(Xaa)$_6$-Cys-(Xaa)$_6$-Cys (SEQ ID No. 231); FIG. 3A). An alanine was added to the N-terminus of the peptide to ensure a correct processing of the signal sequence. A Gly-Gly-Ser-Gly (SEQ ID No. 20) linker was placed between the third cysteine and the gene-3-protein. As phage with the disulfide-free gene-3-protein had about a 100-fold reduced infectivity compared to wild-type phage, large quantities of phage particles were produced. A 1-liter culture incubated over night at 30° C. yielded typically $10^{11}$-$10^{12}$ infective particles. About $10^{12}$ purified infective phage particles were chemically modified with the TBMB scaffold and incubated with either of the two biotinylated proteases. Binding phage were captured on magnetic streptavidin beads and subjected to two further selection rounds. Increasing numbers of phage captured in the second or third selection round indicated that specific binders were enriched. Sequencing of the peptides revealed various consensus sequences either in one or even both of the loops (FIGS. 3B and 3C). The DNA of the selected peptides was amplified by population PCR and inserted into a new plasmid for periplasmic expression of the peptides as D1-D2 fusion protein. Peptide fusion proteins that either showed sequence similarities to other selected clones or that were found in multiple copies, were expressed, purified, chemically modified and tested for their inhibitory activity. The best plasma kallikrein and cathepsin G inhibitors had an IC$_{50}$ of 400 nM (PK2 and PK4) and 100 nM (CG2 and CG4) respectively when tested as a D1-D2 fusion.

Example 3

Screening

In this example, affinity maturation of human plasma kallikrein inhibitors is described.

The comparison of the amino acid sequences of clones selected against human plasma kallikrein revealed that different groups of clones had high sequence similarity mainly in one of the potential binding loops. We assumed that the bi-cyclic molecules were predominately interacting with the conserved binding loop while the loop with diverse amino acid compositions had not evolved for optimal interaction with the protease. Therefore new phage libraries were created with peptides having both, a loop with a sequence of one of the three consensus regions found in the selection with plasma kallikrein and a loop with six random amino acids (FIG. 4A). Phage panning with higher selection pressure using lower antigen concentrations (1 nM to 200 µM), yielded clones having a consensus sequence in the second interaction loop (FIG. 4B). Inhibition assays revealed that the IC$_{50}$ of the best inhibitor (PK15) was improved by about a factor 20 (20 nM) when tested as a D1-D2 fusion.

Example 4

Characterisation of Complexes

Activity and specificity of chemically synthesized inhibitors is investigated.

Figure 5:
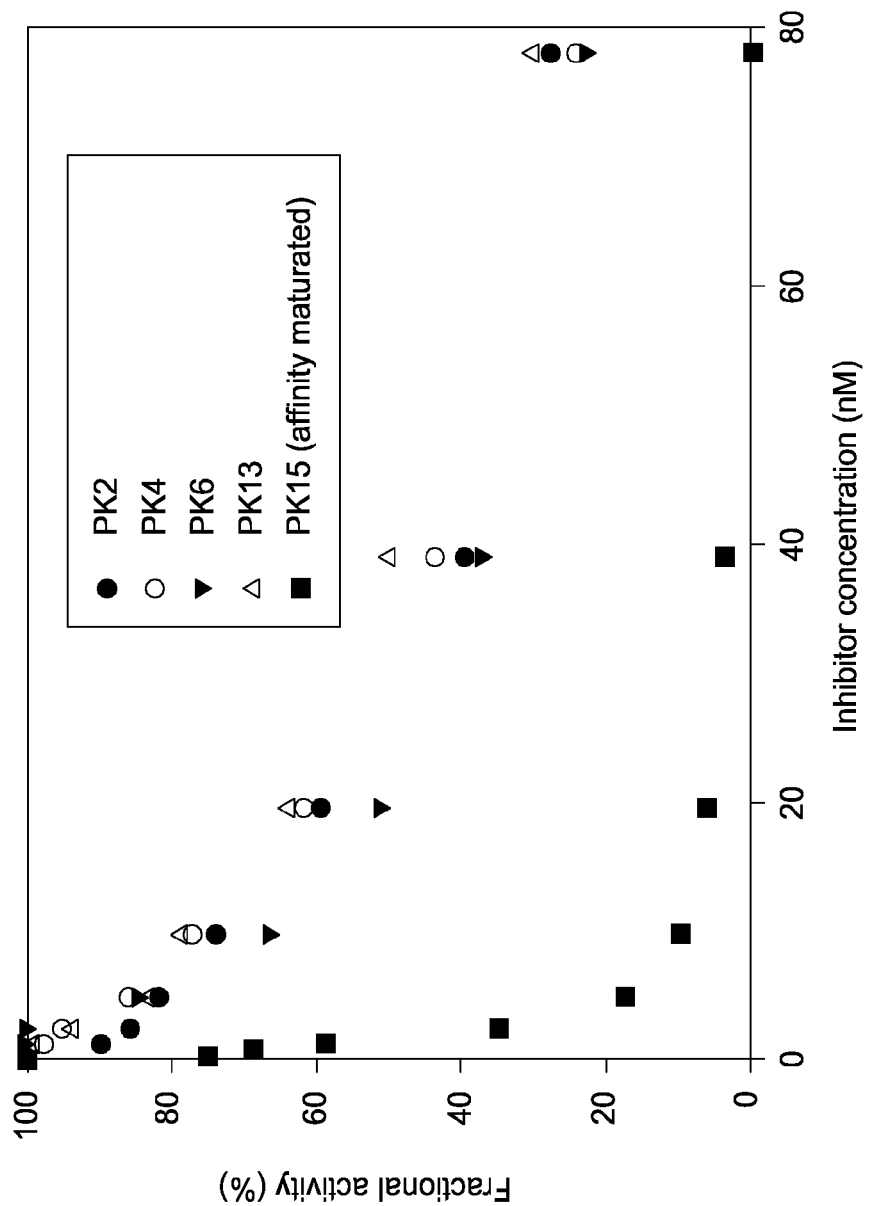
FIG. 5 shows inhibition of human plasma kallikrein by TBMB modified synthetic peptides. The inhibitory activity is expressed as the fractional activity (inhibited rate/uninhibited rate) at varying inhibitor concentrations.

Synthetic peptides of the four best human plasma kallikrein inhibitors isolated in the first selection (PK2, PK4, PK6, PK13) and of the best inhibitor from the affinity maturation selection (PK15) were produced by solid phase synthesis. The peptides were designed to have an alanine with a free amino group at the N-termini and an amidated glycine at the C-termini to represent exactly the charge and chemical environment of the phage displayed peptides. The synthetic TBMB reacted peptides were found to have about 10-fold lower $IC_{50}$'s than the corresponding TBMB reacted D1-D2 fusion peptides (Table A; FIG. 5). The lower affinity of the peptides as D1-D2 fusion may originates from intramolecular binding of the peptide to the gene-3-protein domains and hence a lower apparent inhibitor concentration. The apparent $K_i$ of the TBMB modified peptide PK15 was calculated with the equation of Cheng and Prusoff and was found to be 1.5 nM (Cheng, Y. and Prusoff, W. H., Biochem. Pharmacol., 1973). The $IC_{50}$'s of the linear, non-constrained peptides were at least 250-fold higher than the ones of the TBMB modified peptides (Table A):

TABLE A

| Clone | Amino acid sequence | Mass (Da) | | $IC_{50}$ (nM) | | |
| | | Linear peptide | Bi-cyclic peptide | Linear peptide | Bi-cyclic peptide | |
|---|---|---|---|---|---|---|
| PK2 | H-ACSDRFRNCPLWSGTCG-NH$_2$ | 1871.2 | 1985.3 | >10,000 | 28.6 | (SEQ ID No. 1) |
| PK4 | H-ACSTERRYCPIEIFPCG-NH$_2$ | 1942.9 | 2055.9 | 7181 | 33 | (SEQ ID No. 2) |
| PK6 | H-ACAPWRTACYEDLMWCG-NH$_2$ | 1974.8 | 2088.7 | 5707 | 21.2 | (SEQ ID No. 3) |
| PK13 | H-ACGTGEGRCRVNWTPCG-NH$_2$ | 1764.8 | 1879.1 | >10,000 | 39.1 | (SEQ ID No. 4) |
| PK15 | H-ACSDRFRNCPADEALCG-NH$_2$ | 1825 | 1939.4 | >10,000 | 1.7 | (SEQ ID No. 5) |

Mass spectrometric analysis of inhibitor incubated with human plasma kallikrein showed a mass drop of 18 Da suggesting that a peptide bond in one of the loops of the inhibitor was hydrolysed. The inhibitory activity ($IC_{50}$) of kallikrein-treated inhibitor, however, was as good as the one of the intact, bi-cyclic TBMB modified peptide PK15.

The specificities of the five inhibitors were tested by measuring the inhibitory activity towards mouse plasma kallikrein (79% sequence identity) or the homologous human serine proteases factor XIa (sharing the highest sequence identity with human plasma kallikrein within the human serine proteases; 63%) and thrombin (36% sequence identity). Neither the mouse plasma kallikrein nor one of the homologous human serum proteases were inhibited at the highest concentration tested (10 µM).

Example 5

Use of Entities Identified in Methods of the Invention

In this example, inhibition of contact activation in human plasma by a human plasma kallikrein inhibitor is demonstrated.

Figure 8A:
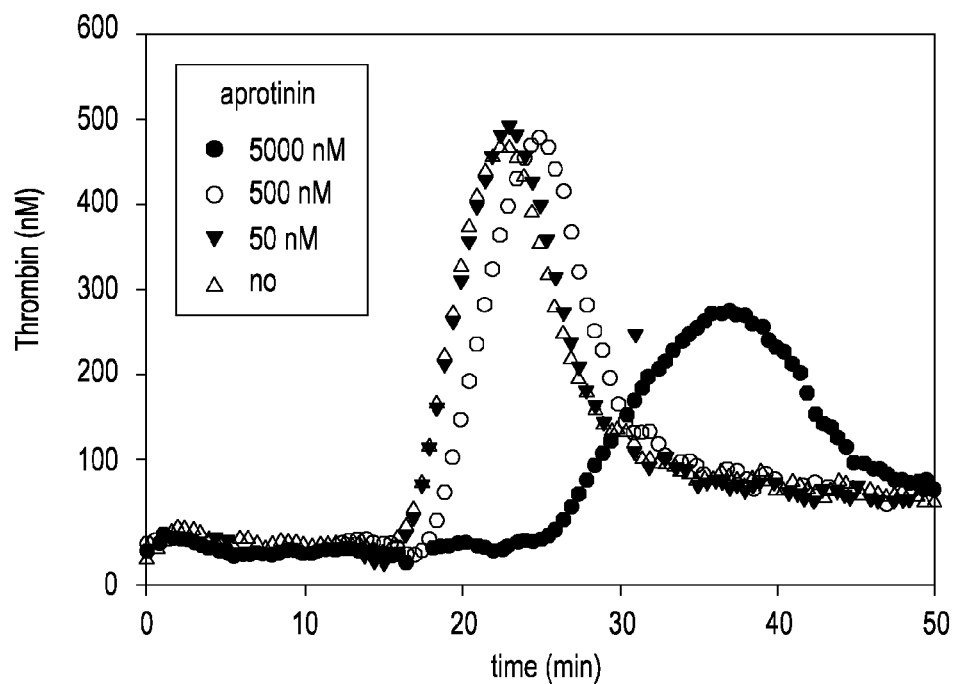
FIG. 8 shows inhibition of contact activation in human plasma by aprotinin and TBMB modified peptide PK15. Effect of aprotinin (FIG. 8A) and TBMB modified peptide PK15 (FIG. 8B) on thrombin generation triggered by actin. Both inhibitors cause dose-dependent prolongation of lag time compared to the control sample.
FIG. 8C: The sum of the activities of factor XIIa and plasma kallikrein was measured with the colorimetric substrate H-D-Pro-Phe-Arg-pNA in human plasma of three different donors treated with varying concentrations of inhibitor. Contact activation was initiated by addition of kaolin. Mean values and standard deviations are indicated.
Figure 8B:
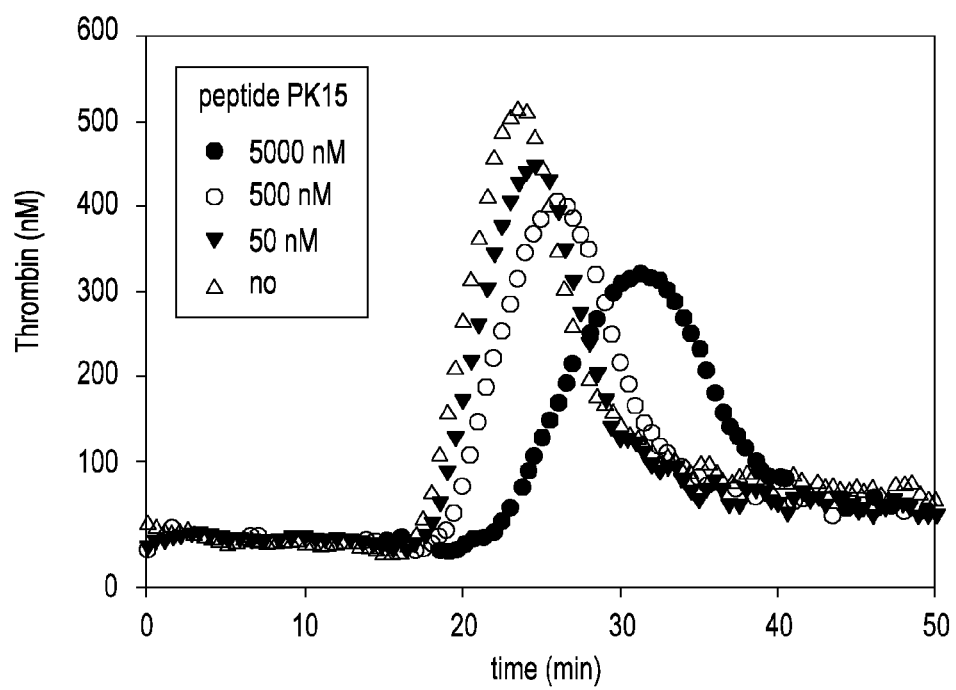
Figure 8C:
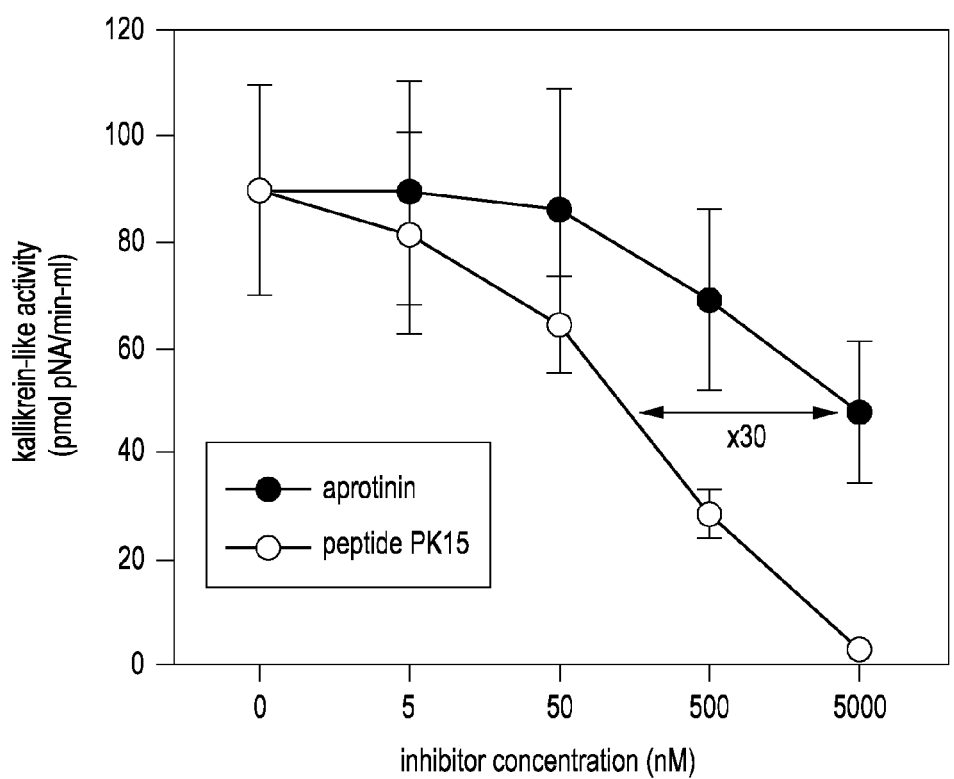

Human plasma kallikrein plays a key role in the first events in contact activation. The ability of TBMB modified peptide PK15 to inhibit contact activation was tested by measuring the prolongation of the thrombin activation time in human plasma in the presence of varying inhibitor concentrations. Thrombin is the last enzyme in the activation cascade of the blood coagulation pathway that is activated. At 50 nM inhibitor concentration, TBMB modified peptide PK15 delayed thrombin formation while aprotinin, a 6 kDa protein inhibitor of human plasma kallikrein had no effect (FIGS. 8A and 7B). At an inhibitor concentration as high as 5 µM the lag time of thrombin activation was more prolonged by aprotinin than by the small molecule inhibitor. Aprotinin is a broad spectrum inhibitor and may inhibit other proteases in the intrinsic pathway when used at a high concentration. In a different assay, we tested whether TBMB modified peptide PK15 can suppress the activation of factor XIIa and plasma kallikrein in human plasma of three different donors. The activation of the two proteases could essentially be suppressed at 5 µM of TBMB modified peptide PK15. We estimate that about a 30-fold higher concentration of aprotinin is necessary to obtain a same inhibition effect. (FIG. 8C).

Example 6

Structure Determination of TBMB Modified Peptide PK15

Figure 6:
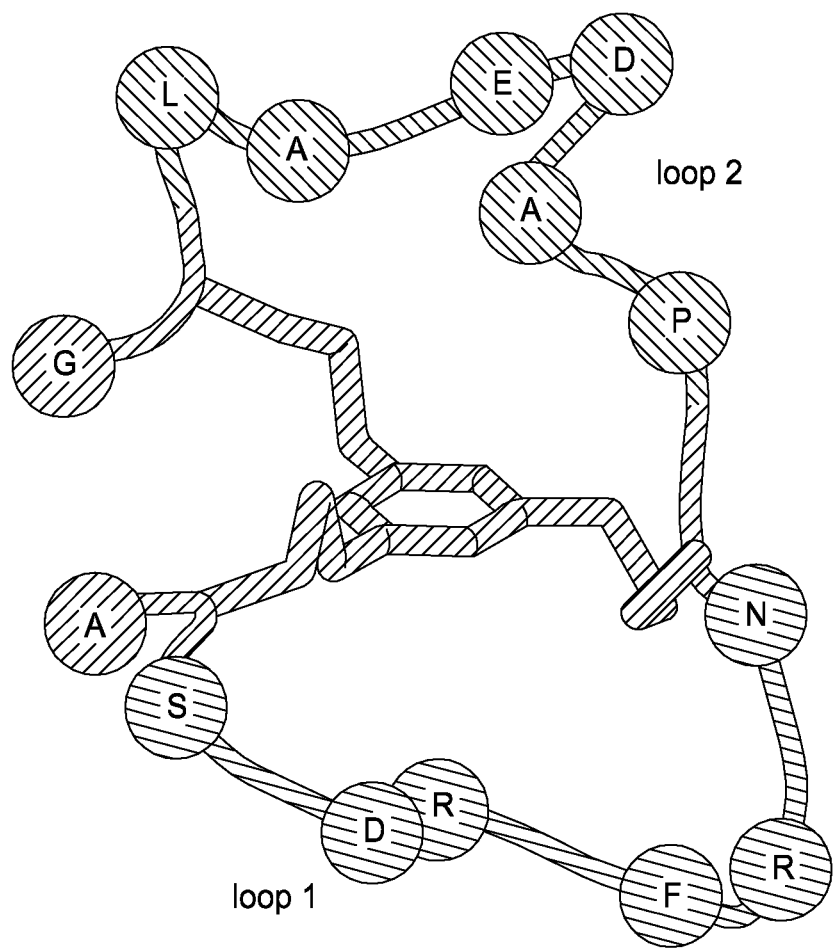
FIG. 6 shows representative NMR solution structure of TBMB modified peptide PK15 shown as a 'sausage' structure. The peptide loops 1 and 2 are shown. The alpha carbon atoms of the amino acids in the peptide loops and at the termini are shown as spheres.

The conformation of TBMB modified peptide PK15 was determined by 2D $^1$H NMR spectroscopy in aqueous solution at pH 6.6. Chemical shift assignments were achieved by standard methods. Analysis of the NOESY spectra provided evidence for a defined backbone conformation. Notable are the chemical shifts of the three protons of the central benzene ring that could be resolved as a result of their different spacial environments. Average solution structures were calculated using NOESY-derived distance restraints (FIG. 6).

Summary of Examples 1 to 6

We have demonstrated the invention with reference to phage display technology to encode the peptide fraction of non-natural small molecule structures (i.e. complexes according to the present invention). The genetic encoding allows the facile generation, selection and amplification of very large combinatorial repertoires. A major difficulty in this approach was to tether the phage encoded peptide repertoires to the small molecule core. We developed a convenient synthesis strategy and established optimal reaction conditions in a number of experiments. Reagent concentrations, solvent composition and reaction temperature had to be chosen carefully to attach specifically linear peptides on phage to small molecules while sparing the phage particles. A specific phage with disulfide-free gene-3-proteins is used to help prevent the generation of product mixtures through reaction of the small molecule with cysteine residues of the phage coat.

We have chosen human plasma kallikrein and cathepsin G as targets to test the efficiency of the in vitro selection techniques of the invention. Molecules with affinities in the lower nanomolar range were isolated against both targets and confirmed that the proposed selection strategy and the molecule design can yield high affinity binders. When assessing the specificity of the human plasma kallikrein inhibitors, we found that neither the mouse plasma kallikrein nor homologous human plasma proteases as factor XIa or thrombin were inhibited. This finding was pleasing since the generation of specific small molecular weight inhibitors to human plasma kallikrein (Young, W. B. et al., Bioorganic and Medicinal Chemistry Letters, 2006) and other human serine proteases is not trivial (reviewed in Abbenante, G. and Fairlie, D. P., Medicinal Chemistry, 2005 and Turk, B., Nature Rev. Drug Discovery, 2006). The access of the small molecule structures to chemical synthesis allows the replacing of specific amino acids with non-natural building blocks and hence the further improving of the affinity of the inhibitors.

Structure determination of one of the plasma kallikrein inhibitors by NMR in solution suggested that the molecule has a defined backbone conformation. As anticipated, the hydrophobic benzene ring forms the core of the molecule. However, none of the amino acid side chains densely packed with the benzene ring for this particular single polypeptide-connector compound combination. Alternative scaffolds with chemical structures that offer more possibilities to interact with the peptide backbone or amino acid side chains may advantageously be used to obtain a denser packing of the peptide fraction if desired. The hydrogen atoms of the 1,3,5-tris-(bromomethyl)-benzene scaffold at the ring positions 2, 4 and 6 could for example be replaced by three identical chemical substituents.

In the selections demonstrated herein, we used a molecule design in which a peptide is tethered via three linkages to a small molecule scaffold to obtain a bi-cyclic peptide structure. Of course, the creation of alternative molecule architectures in which the peptide loops are cleaved by proteases before selection to obtain small molecules with discrete peptide moieties may also be used in selection/screening embodiments. In fact, structures with two discrete peptide moieties were generated in this work when the TBMB modified inhibitor PK15 was cleaved by human plasma kallikrein upon incubation with the enzyme. The singly digested molecule was found to have an inhibitory activity that was as good as the non-hydrolized form. Cleavage of the peptide loops also offers the possibility to attach additional chemical structures to the nascent amino or carboxy termini through further chemical reactions.

We have assessed the therapeutic potential of the evolved human plasma kallikrein inhibitor by testing its ability to inhibit contact activation in human plasma. In cardiac surgery involving cardiopulmonary bypass (CPB) contact of blood with the artificial surface of the CPB machine and tubing activates multiple plasma protease pathways. Serious complications can result, including the systemic inflammatory response syndrome (SIRS), a whole body inflammatory state that can compromise heart and lung function in patients (Miller, B. E. et al., J. of Cardiothoracic and Vascular Anesthesia, 1997). Plasma kallikrein plays a key role in the first events of contact activation and in the amplification of other protease pathways, such as the fibrinolytic and complement systems. A common strategy to suppress contact activation during cardiac surgery is to block the activity of plasma kallikrein with aprotinin, a 6 kDa broad spectrum protease inhibitor from bovine lung tissue. The inhibitor binds plasma kallikrein with a $K_i$ of 30 nM and hence interrupts the intrinsic coagulation pathway through suppression of factor XII activation. Furthermore, inhibition of plasma kallikrein decreases the conversion of plasminogen to plasmin and hence reduces fibrinolysis and associated bleeding. Aprotinin is also a direct inhibitor of plasmin ($K_i$=3 nM). It is thought that direct inhibition of plasmin is the major mechanism of the antifibrinolytic effects leading to reduction of blood loss and reduced need of transfusion. The drug has also adverse effects as anaphylaxis and renal toxicity (reviewed in Mandy A. M. and Webster N. R., Br. J. Anaesth., 2004). An alternative plasma kallikrein inhibitor based on the human kunitz domain scaffold (6 kDa) has recently been developed (Markland, W, et al., Biochemistry, 1996). The drug has a significantly higher affinity ($K_i$=30 μM) and specificity for plasma kallikrein and is expected to be less immunogenic due to its human framework. It is currently tested in phase 2 clinical trials (Dyax Corp., www.dyax.com). Even though our newly developed lead inhibitor has about a 50-fold lower affinity for human plasma kallikrein than the product kunitz domain based inhibitor, it proved to suppress efficiently contact activation ex vivo. Its smaller size (2 kDa) allows not only the facile chemical synthesis but also advantageously minimises the risk of an immunogenic reaction and makes the compound an attractive lead inhibitor for development/for use in CPB operations.

Example 7

Non-Covalent Interactions

The connector compound of the invention provides the further advantage of influencing/stabilising or imposing conformational constraints on the target polypeptide by virtue of non-covalent bonds formed between the connector compound and the target polypeptide. These are advantageously provided in addition to the covalent bonds between the connector compound and the target polypeptide.

It should be noted that such bonding and constraints are not provided by prior art techniques such as crosslinking. Firstly, crosslinking agents are typically too small and/or too flexible to contribute conformational constraint. Secondly, in the specific example of known crosslinking discussed above (e.g. Roberts US2003/0235852A1) the bivalent linker is small (propyl) and highly flexible by intentional design and there is no evidence that this produced any non-covalent interactions or imposed any conformational constraint beyond the joining of two residues within the polypeptide. In any case, this prior art crosslinker is only bivalent.

In this example we demonstrate that advantageous non-covalent bonding between the connector compound and the target polypeptide of the invention is possible.

The structure of a human plasma kallikrein inhibitor generated with the method of the invention (see above examples) was solved by NMR. In the proposed structure, several carbon atoms of the polypeptide are in close proximity (<4 angstrom) to the carbon atoms of the connector compound. This suggests that noncovalent interactions are present, in this example hydrophobic interactions, between the core and the polypeptide of the invention.

These interactions are:

| | | |
|---|---|---|
| Ser3 CB | Rng C26 | 3.62 Å |
| Ser3 CB | Rng C2 | 4.0 Å |
| Ser3 CB | Rng CMe2 | 3.63 Å |
| Cys2 CB | Rng CMe2 | 2.56 Å |
| Cys9 CB | Rng C29 | 3.13 Å |
| Cys9 CB | Rng C9 | 3.32 Å |
| Pro10 CG | Rng CMe9 | 3.8 Å |

| | | |
|---|---|---|
| Pro10 CD | Rng CMe9 | 3.13 Å |
| Cys16 CB | Rng C16 | 3.43 Å |
| Cys16 CB | Rng C26 | 3.79 Å |

In addition, hydrogen-hydrogen interactions between hydrogen atoms of the polypeptide and hydrogen atoms of the connector compound were detected by 1H-NMR NOESY spectroscopy.

Thus, multiple classes of non-covalent interaction between the connector compound and target polypeptide of the invention are demonstrated. These advantageously provide further conformational constraint to the polypeptides of the invention.

Example 8

Phage Encoded Combinatorial Chemical Libraries

Overview

Phage display technology has previously proved effective for making therapeutic antibodies from combinatorial libraries but difficult to apply for making small molecule drugs. Here we describe a phage strategy for the selection of mimics of macrocyclic compounds produced by the non-ribosomal peptide synthases. The peptide repertoires were designed with three reactive cysteine residues, each spaced apart by several random amino acid residues, and fused to the phage gene-3-protein. Conjugation with a connector compound (in this example tris-(bromomethyl)benzene) via the reactive cysteines generated repertoires of peptide conjugates with two peptide loops anchored to a mesitylene core. Iterative affinity selections yielded several enzyme inhibitors; after further mutagenesis and selection, we isolated a lead inhibitor (PK15)($K_i$=1.5 nM) specific to human plasma kallikrein that efficiently interrupted the intrinsic coagulation pathway in human plasma tested ex vivo. Thus it is demonstrated that this approach provides a powerful means of generating and screening such macrocycle mimics.

Background

The discovery of novel ligands to receptor, enzyme and nucleic acid targets represents the first stage in the development of therapeutic drugs. For drugs based on small organic ligands, high throughput screening (HTS) has proved a popular strategy; large libraries of compounds are synthesized (or purchased) and each compound assayed for binding to the targets. With the use of robots it is possible to screen $10^5$-$10^6$ compounds per day, but the hits usually require further chemistry to improve their binding affinity and target specificity. For drugs based on nucleic acids, peptides or proteins, biological selection methods offer an alternative strategy. These methods (such as phage display, ribosome display, mRNA display or RNA/DNA aptamer technologies) rely on (a) creating a diverse library wherein the phenotype (binding to target) of each member of the library is linked to its genotype (the encoding DNA or RNA), and (b) an interative cycle in which library members are selected for binding to target, and then amplified (by replication in a host cell, or by copying of the encoded nucleic acid in vitro). At each round of selection the binders are thereby enriched over the non-binders. Very large libraries ($10^9$-$10^{13}$ members) can be efficiently screened by a few rounds of selection and lead hits can be refined by mutation and further selection[3]. The approach is very powerful and has been used to create therapeutic antibodies such as Humira™. Several attempts have been made to develop selection methods for the isolation of small organic ligands. Typically DNA is used as a tag that can be readily synthesized, sequenced, amplified and/or hybridized. For example, small molecules can each be conjugated to a unique DNA[6] (or bacteriophage[7]) tag, and the conjugates mixed together to create a tagged small molecule library. After selection of the library against the target, the small molecule "hits" can be identified by the sequences of their (amplified) tags. Alternatively the DNA tags can be introduced during the synthesis of combinatorial chemical libraries. For example, small molecules and a corresponding tag are synthesised in parallel on the same bead[8], or hybridisation of the tag is used to govern the route of chemical synthesis[9]. From such libraries the synthetic route (and thereby structure) of the selected hits can be deduced from the sequence of the tag. Notwithstanding their ingenuity, these methods suffer from a common disadvantage; the small molecule is linked to the DNA tag only during the first round of selection, rendering iterative cycles impossible (and limiting application to small libraries). Thus the prior art presents numerous difficulties.

Figure 9A:
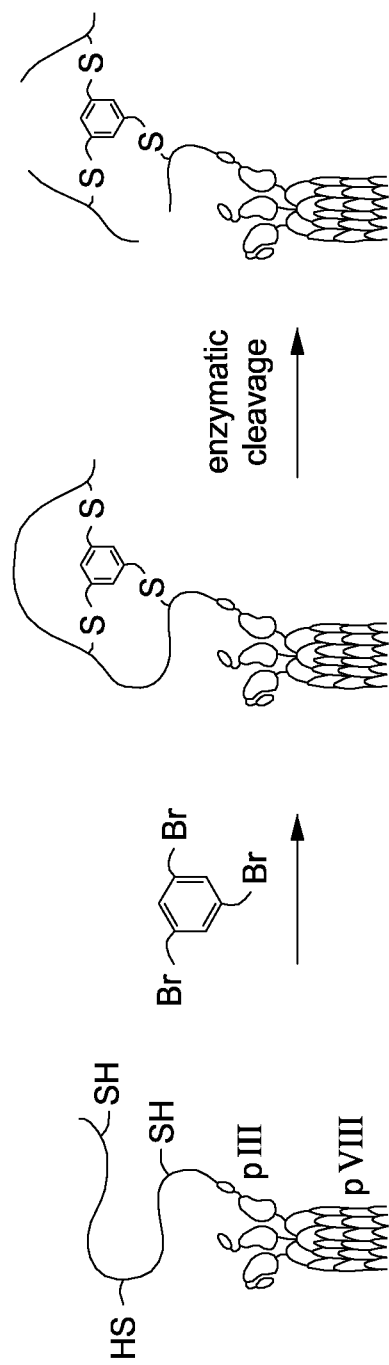
FIG. 9A shows generation of phage encoded combinatorial small chemical libraries. A phage encoded peptide with three cysteine residues is tethered to the tri-functional compound tris-(bromomethyl)benzene in a nucleophilic substitution reaction. The resulting chemical entities could optionally be further modified through enzymatic reactions.

In this example, we demonstrate that the invention can be used to chemically modify peptides on phage during the selection process to create mimics of peptide macrocyclic compounds. Recently methods have been described for tethering peptides through reactive side chains (eg. cysteines) to the functional groups of an organic scaffold[12], and thereby generating polycyclic peptide conjugates comprising an organic core decorated with peptide loops. As the structures are reminiscent of the peptide macrocyclic drugs, we explored the possibility of creating and selecting libraries of such conjugates on filamentous phage (FIG. 9a). Whereas peptide macrocycles are normally made in vivo by non-ribosomal peptide synthases, our strategy uses ribosomal synthesis in vivo then chemical conjugation ex vivo.

Results

Conjugation of Organic Scaffold to Peptides Displayed on Phage

We used the small organic compound tris-(bromomethyl)benzene (TBMB) as a scaffold (connector compound) to anchor peptides containing three cysteine residues[12,15] (FIG. 9a). The reaction occurs in aqueous solvents at room temperature, and the three-fold rotational symmetry of the TBMB molecule ensures the formation of a unique structural and spatial isomer.

Figure 10A:
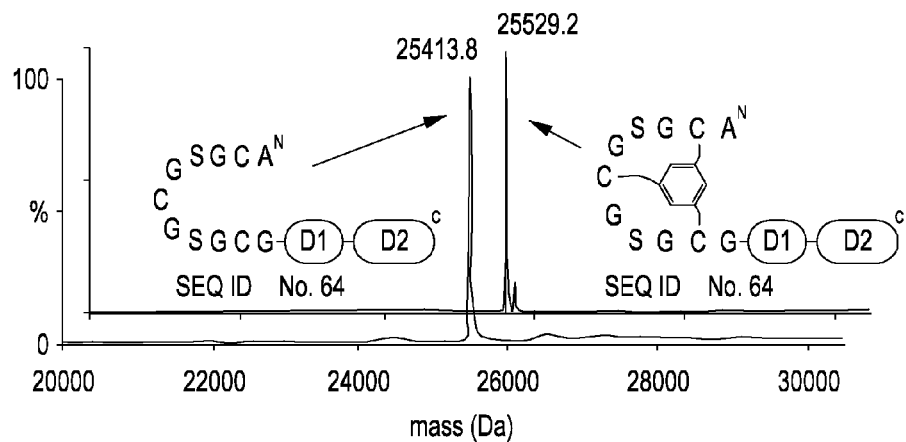
FIG. 10a: Molecular mass of the GCGS-GCGSGCG (SEQ ID No. 15)-D1-D2 fusion protein before and after reaction with 10 µM TBMB in 20 mM $NH_4HCO_3$, 5 mM EDTA, pH 8, 20% ACN at 30° C. for 1 hour determined by mass spectrometry. The mass difference of the reacted and non-reacted peptide fusion protein corresponds to the mass of the small molecule core mesitylene.
Figure 10B:
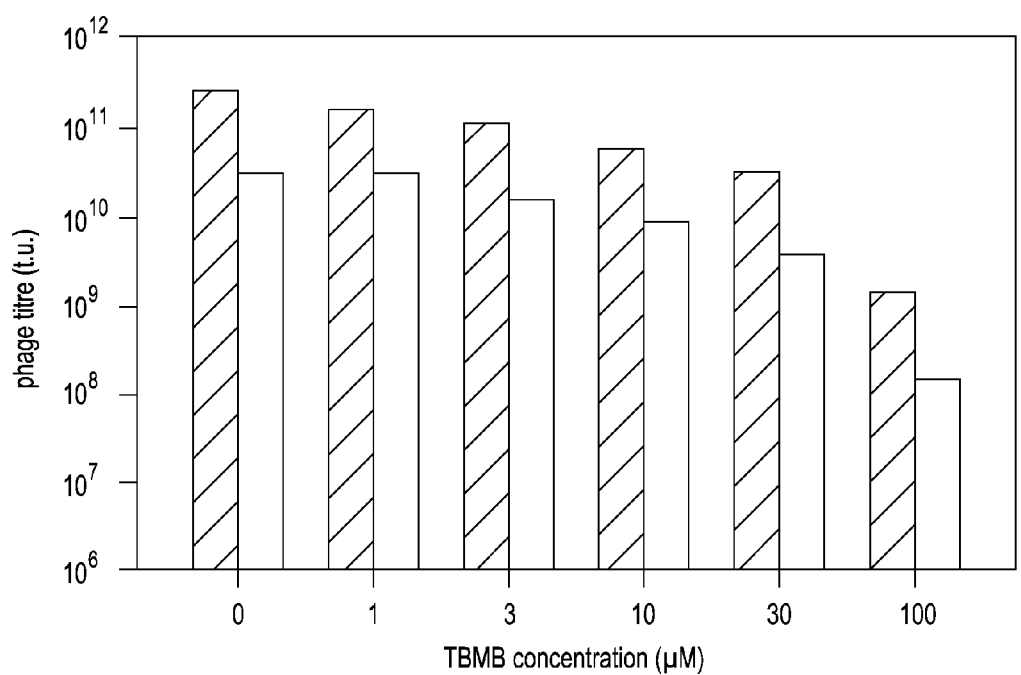
FIG. 10b: Titres (transducing units) of phage that were reduced and treated with various concentrations of TBMB in 20 mM $NH_4HCO_3$, 5 mM EDTA, pH 8, 20% ACN at 30° C. for 1 hour. Titres of phage from fdg3p0ss21 (black) and from library 1 (white) are shown.
Figure 15A:
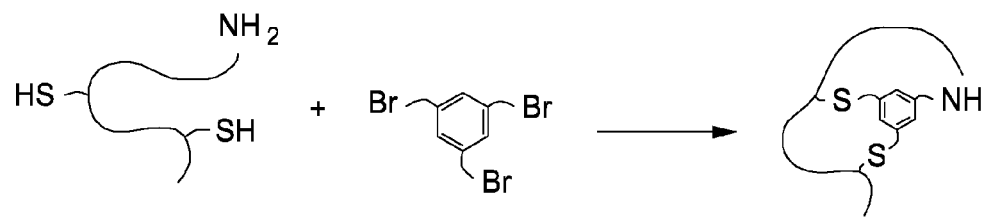
FIG. 15A: Plausible reaction mechanism of TBMB with a peptide fusion protein containing two cysteine residues.
Figure 15B:
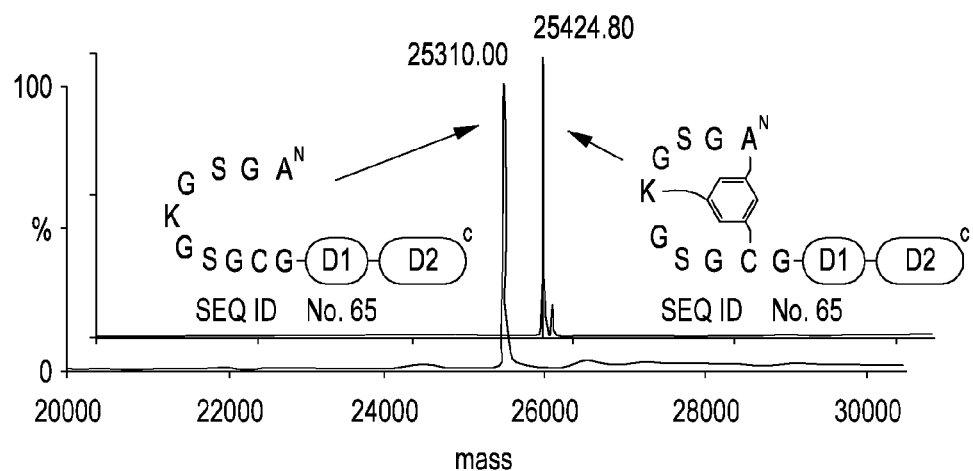
FIG. 15B: Mass spectra of a peptide fusion protein with two cysteines before and after reaction with TBMB.
Figure 15C:
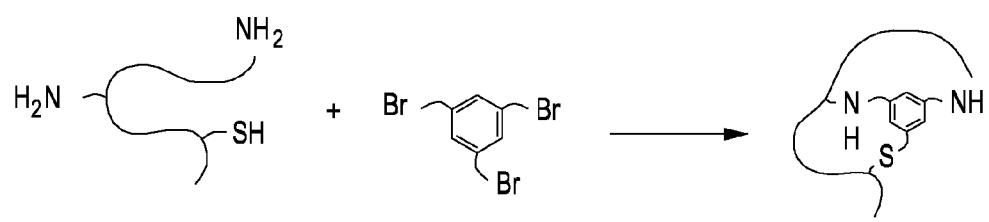
FIG. 15C: Plausible reaction mechanism of TBMB with a peptide fusion protein containing one cysteine and one lysine residue.
Figure 15D:
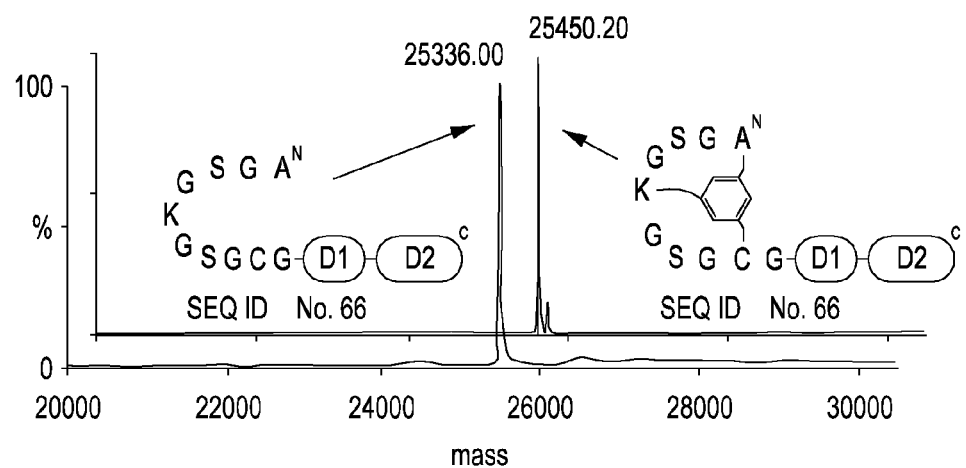
FIG. 15D: Mass spectra of a peptide fusion protein with one cysteine and one lysine residue before and after reaction with TBMB.

We first elaborated the reaction conditions for conjugation of the peptide $^N$GCGSGCGSGCG$^C$ (SEQ ID No. 15) fused to the soluble D1-D2 domains of the phage pIII, analysing the molecular weight of the products by mass spectrometry. However, we were unable to selectively conjugate the three cysteine residues of the peptide with TBMB while sparing the disulphide bridges of D1 and D2 (C7-C36, C46-C53, C188-C201). This prompted us to take advantage of a disulfide-free gene-3-protein recently developed by Schmidt F. X. and co-workers[16]. The peptide-D1-D2 (disulfide free) fusion protein was reduced with tris-(carboxyethyl)phosphine (TCEP), the TCEP removed and TBMB added. A concentration of 10 μM TBMB was sufficient for quantitative reaction with of peptide-fusion protein at 30° C. in one hour, giving predominantly one product with the expected molecular mass (Δ mass expected=114 Da; FIG. 10a). No product was detected with the (disulfide-free) D1-D2 protein. Unexpectedly, we found that reaction of TBMB with peptide-D1-D2 (disulfide-free) fusions containing only two cysteine residues ($^N$AGSGCGSGCG$^C$-(SEQ ID No. 17)D1-D2) yielded a product with a molecular mass consistent with reaction of both cysteines and the α-amino group at the peptide N-terminus (FIGS. 15a and 15b). Similarly, the reaction of TBMB with a peptide-D1-D2 (disulfide free) fusions having one cysteine and a lysine ($^N$AGSGKGSG CG$^C$(SEQ ID No. 18)-D1-D2) yielded a molecular mass consistent with the reaction of the cysteine, the α-amino group of the N-terminus and the ε-amino group of the lysine (FIGS. 15c and 15d). Having identified suitable conditions, we reacted TBMB with (disulfide-free p3) phage bearing the peptide $^N$GCGSGCGSGCG$^C$ (SEQ ID No. 15). This led to a small loss (5-fold) of phage infectivity (FIG. 10b).

Creation of Polycyclic Peptide Library and Affinity Selection

We designed a library of peptides comprising two sequences of six random amino acids flanked by three cysteines (Cys-(Xaa)$_6$-Cys-(Xaa)$_6$-Cys (SEQ ID No. 23); FIG. 11a) for display on the (disulphide-free p3) phage. An alanine residue was added to the N-terminus of the peptide to ensure a correct processing of the signal sequence. A Gly-Gly-Ser-Gly (SEQ ID No. 20) linker was placed between the third cysteine and the gene-3-protein. As the (disulfide-free p3) phage had a 100-fold reduced infectivity compared to wild-type phage, large quantities of phage particles were produced from the library (estimated 4.4×10$^9$ variants). A 1-liter culture incubated over night at 30° C. yielded typically 10$^{11}$-10$^{12}$ infective particles.

We tested the library of polycyclic peptides for binding and inhibition of the human proteases plasma kallikrein and cathepsin G. About 10$^{12}$ purified infective phage particles were chemically modified with TBMB and then incubated with the biotinylated target proteins. After capture on magnetic streptavidin or avidin beads, the enriched phage were treated to two further rounds of selection, each round comprising amplification (by bacterial infection), chemical conjugation and capture with the biotinylated targets. The phage titre increased after the second and third rounds suggesting enrichment of specific binders. DNA encoding the peptides was PCR-amplified from the selected population of phage in the third round, and recloned for periplasmic expression as peptide-D1-D2 (disulfide free D1-D2) fusion proteins and sequenced. This revealed consensus sequences in one or both of the peptide loops (FIGS. 11b and 11c) and several were expressed, purified, conjugated with TBMB and tested for their inhibitory activity to protease. The best plasma kallikrein and cathepsin G inhibitors had an IC$_{50}$ of 400 nM (PK2 and PK4) and 100 nM (CG2 and CG4) respectively when tested as a D1-D2 fusion. Since we screened the phage selected clones for inhibition (rather than binding) we can not state whether also molecules were selected that bind to the proteases but do not inhibit them. However, the finding that the vast majority of clones tested after the phage selection displayed inhibitory activities suggests that predominantly inhibitors were selected.

Affinity Maturation of Human Plasma Kallikrein Inhibitors

Most of the sequences of the kallikrein binders revealed consensus sequences in one or other of the peptide loops. Three new libraries were created with one of the three consensus regions in one loop and six random amino acids in the other loop (FIG. 12a). The libraries were mixed and phage panned under stringent conditions (1 nM to 200 μM biotinylated kallikrein). The random sequence converged to a new consensus, yielding clones with consensus sequences in both loops (FIG. 12b). Inhibition assays revealed that the IC$_{50}$ of the best inhibitor (PK15) was 20 nM when tested as a D1-D2 fusion.

Activity And Specificity of Chemically Synthesized Inhibitors

Synthetic peptides corresponding to four kallikrein inhibitors from the primary selection (PK2, PK4, PK6 and PK13) and the best inhibitor from the affinity maturation selection (PK15) were produced by solid phase chemical synthesis. The peptides had an alanine residue at the N-terminus and an amidated glycine at the C-terminus to represent the charge and chemical environment of the phage displayed peptides. The TBMB conjugated synthetic peptides were at least 250-fold more potent inhibitors of kallikrein activity than the unconjugated peptides (Table 1).

Table 1—Chemically synthesized peptide inhibitors. The amino acid sequences of five plasma kallikrein inhibitors (17-mers) are shown. The sequences of the synthetic peptides derive from the clones PK2, PK4, PK6, PK13 (isolated in phage selections using library 1) and from clone PK15 (an affinity matured clone isolated from library 2). Indicated are the molecular masses and the inhibitory activities before and after the modification of the peptides with TBMB:

TABLE 1

| Clone | Amino acid sequence | Mass (Da) Linear peptide | Mass (Da) Bi-cyclic peptide | IC$_{50}$ (nM) Linear peptide | IC$_{50}$ (nM) Bi-cyclic peptide | |
|---|---|---|---|---|---|---|
| PK2 | H-ACSDRFRNCPLWSGTCG-NH$_2$ | 1871.2 | 1985.3 | >10,000 | 28.6 | (SEQ ID No. 1) |
| PK4 | H-ACSTERRYCPIEIFPCG-NH$_2$ | 1942.9 | 2055.9 | 7181 | 33 | (SEQ ID No. 2) |
| PK6 | H-ACAPWRTACYEDLMWCG-NH$_2$ | 1974.8 | 2088.7 | 5707 | 21.2 | (SEQ ID No. 3) |
| PK13 | H-ACGTGEGRCRVNWTPCG-NH$_2$ | 1764.8 | 1879.1 | >10,000 | 39.1 | (SEQ ID No. 4) |
| PK15 | H-ACSDRFRNCPADEALCG-NH$_2$ | 1825 | 1939.4 | >10,000 | 1.7 | (SEQ ID No. 5) |

Figure 9B:
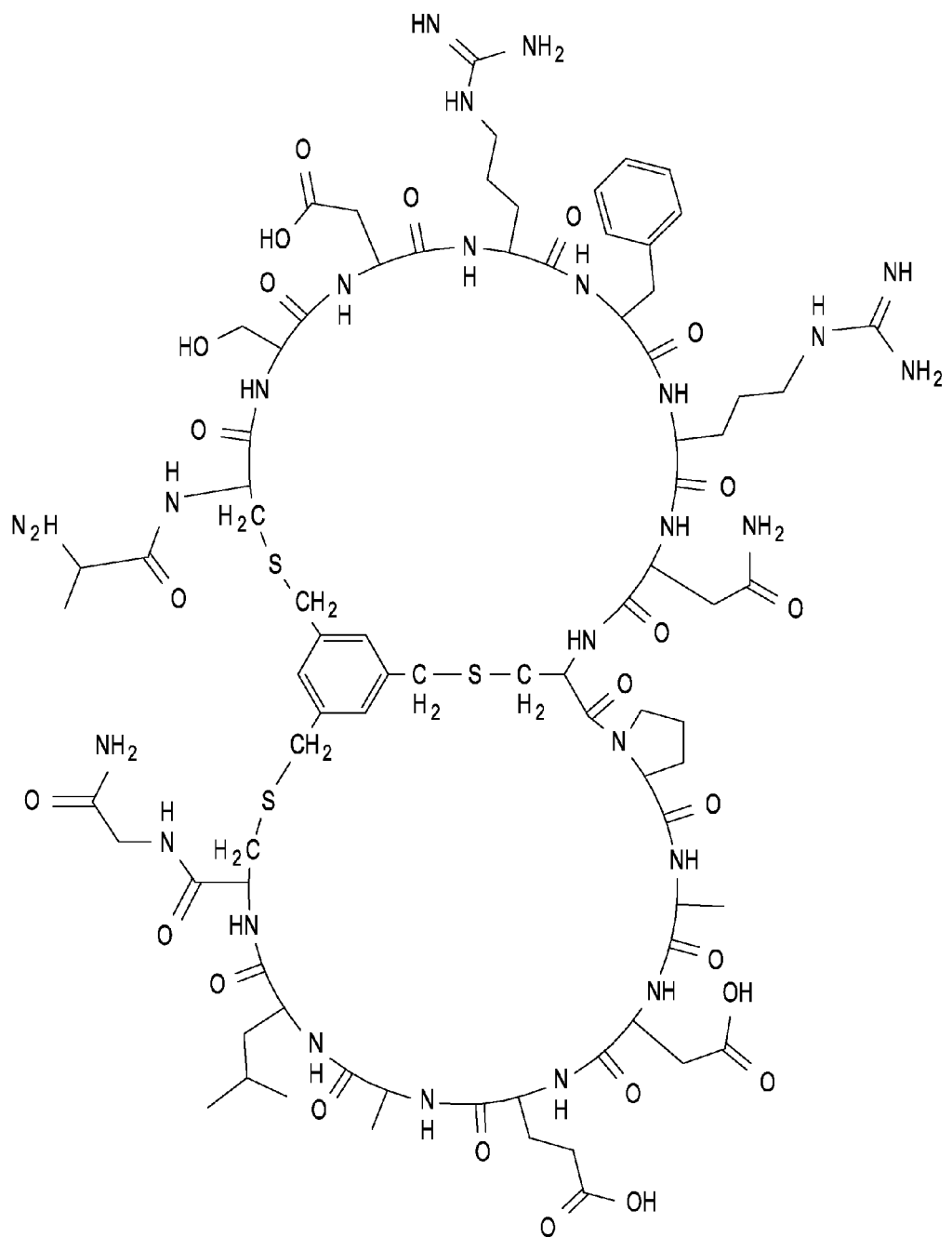
FIG. 9B: Chemical structure of a macrocyclic plasma kallikrein inhibitor isolated by phage display (PK15).
Figure 13:
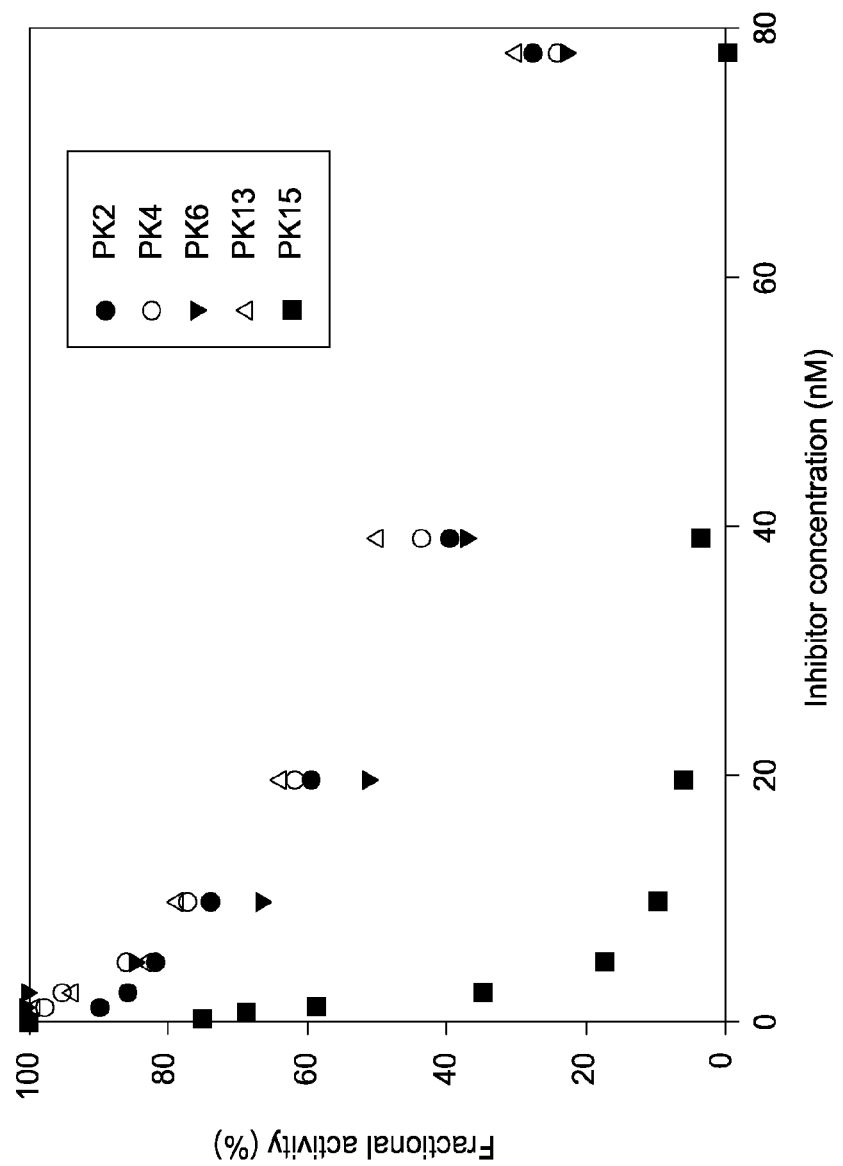
FIG. 13 shows inhibition of human plasma kallikrein by TBMB modified synthetic peptides. The inhibitory activity is expressed as the fractional activity (inhibited rate/uninhibited rate) at varying inhibitor concentrations. Clones PK2, PK4, PK6 and PK13 were isolated in phage selections using library 1. PK15 derives from library 2 and is an affinity matured inhibitor.

They were more potent inhibitors than the peptide-D1-D2 conjugates by a factor of more than ten (Table 1; FIG. 13); presumably this is due to binding of the conjugated peptide moiety to the D1-D2 moiety. The apparent inhibition constant (K$_i$) of the peptide conjugate PK15 (FIG. 9b) was calculated to be 1.5 nM using the equation of Cheng and Prusoff[17]. Incubation of the conjugate PK15 with kallikrein leads to hydrolysis of a peptide bond after prolonged incubation (90% cleavage after 24 h at 37° C.), as shown by a mass gain of 18 Da, but the inhibitory activities of cleaved and uncleaved samples proved similar (IC$_{50}$ 2.2 nM and 1.6 nM respectively).

The five inhibitors were also tested against mouse plasma kallikrein (79% sequence identity) or the homologous human serine proteases factor XIa (63% sequence identity) and thrombin (36% sequence identity). None inhibited these enzymes at the highest concentration tested (10 μM).

Figure 16:
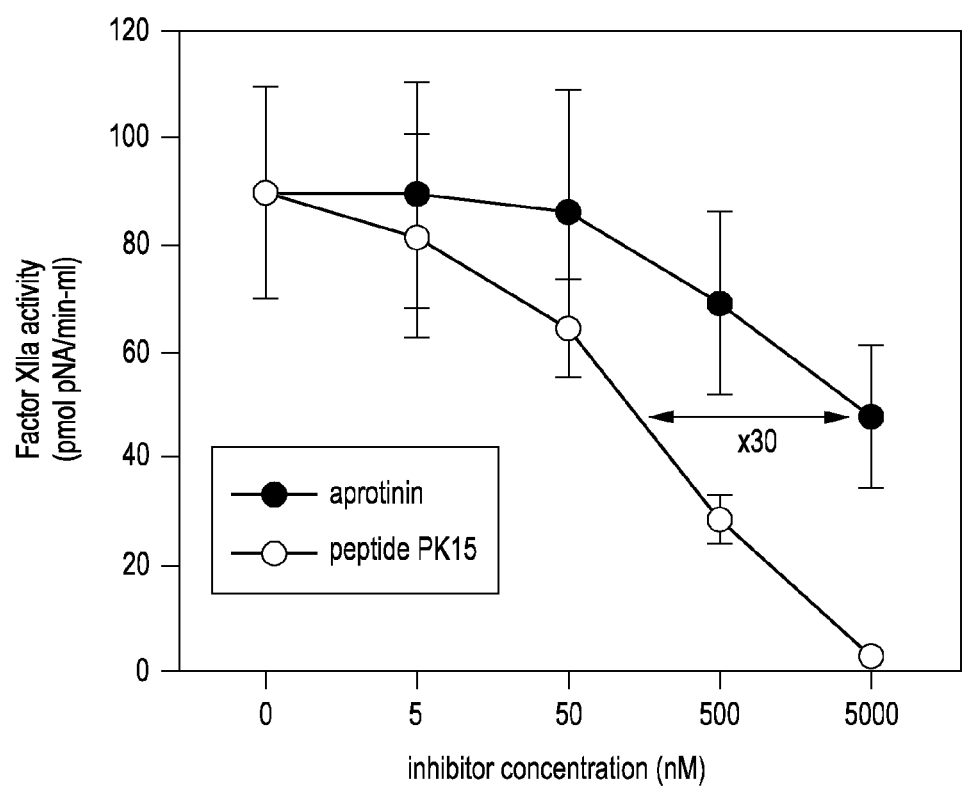
FIG. 16 shows suppression of factor XII activation in human plasma through the inhibition of plasma kallikrein with aprotinin or TBMB modified peptide PK15. The intrinsic coagulation pathway in human plasma of three different donors was initiated by addition of kaolin. The negatively charged surface of kaolin activates small amounts of factor XII. Prekallikrein is converted to kallikrein by activated factor XII (XIIa), and kallikrein exerts a positive feedback to activate more factor XII. The activity of factor XIIa was measured with the colorimetric substrate H-D-Pro-Phe-Arg (SEQ ID No. 37)-pNA. Mean values and standard deviations of factor XIIa activity are indicated.

Interruption of the Intrinsic Coagulation Pathway by a Human Plasma Kallikrein Inhibitor Human plasma kallikrein plays a key role in the first events of the intrinsic coagulation pathway by converting factor XII to factor XIIa which then acts on the next protease in the pathway. We tested whether conjugate PK15 could inhibit the activation of factor XIIa in human plasma samples. The pathway was triggered with caolin and the activity of factor XIIa was measured with a colorimetric substrate. The activity of XIIa was halved in the presence of 160 nM conjugate PK15 (FIG. 16). By comparison 5 µM of aprotinin, a 6 kDa bovine serine protease inhibitor also used clinically as a plasma kallikrein inhibitor ($K_i$=30 nM), was required for the same effect.

Structure Determination of TBMB Modified Peptide PK15

Figure 14:
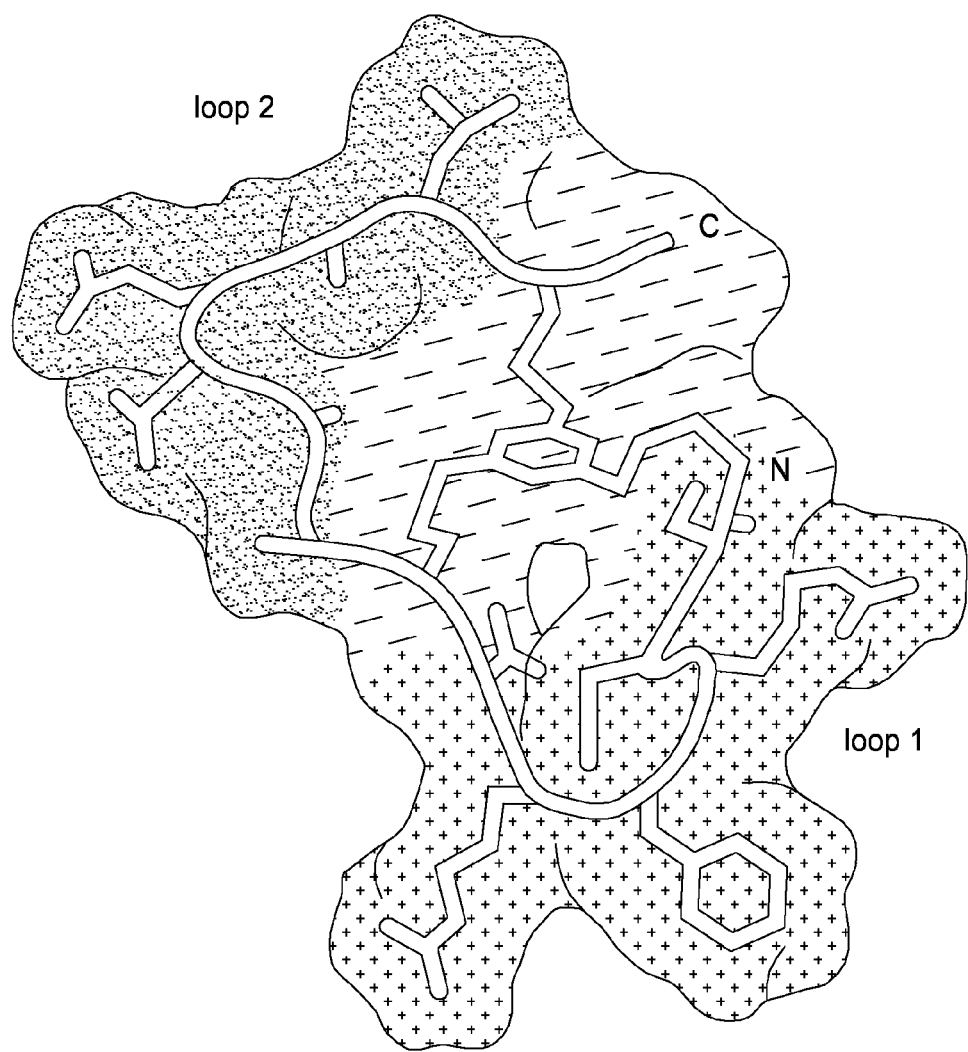
FIG. 14 shows NMR solution structure of TBMB modified peptide PK15. The peptide loops 1 and 2 are shown. The mesitylene core, the three cysteine residues and the terminal alanine (N-terminus) and glycine (C-terminus) are shown in the center of the struction in the area marked with dots. The backbone atoms of the peptide are represented as sausage and the side chains of the amino acids are shown as sticks.

2D $^1$H NMR spectra of the conjugate PK15 were recorded and a sequence specific alignment of the chemical shifts of the TOCSY and NOESY spectra was possible. A conformation of the inhibitor calculated on the NOESY-derived distance restraints is shown in FIG. 14. The two peptide loops are arranged around the mesitylene core to which they are covalently attached but do not interact with each other. The loops do not pack densely against the core but several carbon atoms of the polypeptide (Cys 9 CB, Cys16 CA, Gly 17 CA) are within 4 Å of atoms of the molecular core suggesting there may be some hydrophobic interactions.

Discussion of Example 8

We have shown how the reaction of tris-(bromomethyl) benzene (TBMB)[12] with libraries of cysteine-rich peptides displayed on filamentous bacteriophage generates conjugates (complexes according to the present invention) amenable to iterative selection. It was a challenge to conjugate the displayed peptide while sparing the phage, and we had to vary reagent concentrations, solvent composition and reaction temperature, and also use phage lacking disulfides in the gene-3-protein. From a library of >$10^9$ members and iterative selections we succeeded in isolating potent human plasma kallikrein inhibitors (<2000 Da). Our lead inhibitor (PK15) with $K_i$=1.5 nM efficiently interrupted the intrinsic coagulation pathway in human plasma tested ex vivo, and was highly specific: it did not inhibit mouse plasma kallikrein or the homologous human plasma proteases factor XIa and thrombin.

Our repertoire was built from 17 residue peptides with three cysteines, each spaced apart by six random amino acids. After conjugation with TBMB the peptides are expected to form two six-residue loops attached to a mesitylene core, as indeed confirmed by the structure of the PK15 kallikrein inhibitor solved by NMR (FIG. 14). Such polycyclic peptides should have advantages over both disulfide-bonded and linear peptides. The advantages of polycyclic peptides over disulfide bonded peptides are that the covalent carbon-sulfur bonds once formed are inert to exchange[18], and are also stable in reducing environments[18]. The advantage of polycyclic peptides over linear peptides is that they are cross-linked and more constrained. This has two main consequences: (a) constrained peptides are expected to bind more tightly to targets (due to the smaller loss of conformational entropy). Our literature review of peptide inhibitors isolated by phage display shows that the majority contain disulphides, and have inhibition constants in the micromolar range (Table 3).

TABLE 3

Phage selected peptide inhibitors. Indicated are the sequences of the peptides, the enzyme targets and the binding affinities. The cysteine residues that form disulfide bridges are underlined.

| Target | Peptide sequence | Affinity | Reference | |
|---|---|---|---|---|
| Prostate specific antigen (PSA) | CVAYCIEHHCWTC | $K_D$ = 2.9 µM | 1 | (SEQ ID No. 24) |
| Human kallikrein 2 | SRFKVWWAAF | $IC_{50}$ = 3.4 µM | 2 | (SEQ ID No. 25) |
| Urokinase-type plasminogen activator (uPA) | CSWRGLENHRMC | $K_I$ = 6.7 µM | 3 | (SEQ ID No. 26) |
| Urokinase-type plasminogen activator (uPA) | CPAYSRYLDC | $K_I$ = 0.4 µM | 4 | (SEQ ID No. 27) |
| Chymotrypsin | CCFSWRCRC | $K_I$ = 1 µM | 5 | (SEQ ID No. 28) |
| TF-fVII | EEWEVLCWTWETCER | $IC_{50}$ = 1.5 nM | 6 | (SEQ ID No. 29) |
| Angiotensin converting enzyme 2 (ACE2) | GDYSHCSPLRYYPWWKCTYPDP | $K_I$ = 2.8 nM | 7 | (SEQ ID No. 30) |
| ErbB-2 | KCCYSL | $K_I$ = 30 µM | 8 | (SEQ ID No. 31) |
| Urease | YDFYWW | $IC_{50}$ = 30 µM | 9 | (SEQ ID No. 32) |
| Pancreatic lipase | CQPHPGQTC | $IC_{50}$ = 16 µM | 10 | (SEQ ID No. 33) |
| Beta-lactamase | CVHSPNREC | $IC_{50}$ = 9 µM | 11 | (SEQ ID No. 34) |
| DNase II | CLRLLQWFLWAC | $K_I$ = 0.2 µM | 12 | (SEQ ID No. 35) |

Only two peptide inhibitors were as potent as PK15; both contained a disulfide bond and at least two tryptophan residues. This suggests that the constrained conformation and the possibility of hydrophobic interactions are key for these high affinities; (b) constrained (and cross-linked) peptides should also be more resistant to cleavage and/or inactivation than linear peptides. Indeed in our work the inhibitor PK15 was cleaved in one of the loops after prolonged incubation with human plasma kallikrein, but remained intact and active.

The polycyclic conjugates are amenable to both genetic and chemical engineering. The molecular weight of PK15 (1939.4 Da) is higher than several peptide macrocyclic drugs (Table 4), but it would be possible to use shorter loops. For example by altering the spacing of the cysteines, the loop length is readily varied, or even extra segments added to the peptide termini.

TABLE 4

Size comparison of macrocyclic drugs.

| Name | Cycle size(s) | Molecular mass (Da) | Application |
|---|---|---|---|
| Actionmycin | 16, 16 | 1255.42 | anticancer |
| Amphotericin B | 38 | 924.08 | antifungal |
| Azithromycin | 15 | 748.88 | antibiotic |
| Caspofungin | 21 | 1093.31 | antifungal |
| Cyclosporin | 32 | 1202.61 | immunosupression |
| Daptomycin | 31 | 1619.71 | antibiotic |
| Erythromycin | 14 | 733.93 | antibiotic |
| Ixabepilone | 16 | 506.70 | anticancer |
| Ocreotide | 20 | 1019.24 | hormone |
| Oxytoxin | 20 | 1007.19 | hormone |
| Polymyxin B | 23 | 1301.56 | antibiotic |
| Rapamyzin | 29 | 914.17 | immunosupression |
| Rifabutin | 27 | 847.01 | antibiotic |
| Vancomycin | 16, 16, 12 | 1449.30 | antibiotic |

Further variations could include mutagenesis of the loops (as with the affinity maturation of PK15); proteolytic cleavage in one or both loops to generate peptide segments "branched" at the cysteines; chemical conjugation to the nascent peptide termini after loop cleavage[21]; or the use of variant organic cores. For example, a larger organic core, or one with more functional groups could interact more extensively with the loops or with the target, and could also be used to introduce entirely new functions such as fluorescence. If these operations were performed on the phage-displayed conjugate, the variations would be selectable by an iterative process. As the peptide conjugates are also amenable to chemical synthesis, further variations (such as the substitution by unnatural amino acids) could be introduced synthetically.

Inhibitors of human plasma kallikrein are being developed clinically for treatment of hereditary angiodema and coronary bypass surgery, but it has proved difficult to make small molecules that are specific for the kallikrein (reviewed in 22,23). The fact that we so readily obtained a high affinity and highly specific inhibitor by iterative selection of polycyclic peptide conjugates on phage augers well for this strategy.

Materials and Methods

Chemical Modification of Peptide Repertoires with TBMB on Phage

Phage peptide libraries that are based on the plasmid fdg3p0ss2116 were cloned and produced as described below. Typically 1011-1012 t.u. of PEG purified phage were reduced in 20 ml of 20 mM $NH_4HCO_3$, pH 8 with 1 mM TCEP at 42° C. for 1 hr. The phage were spun at 4000 rpm in a vivaspin-20 filter (MWCO of 10'000) to reduce the volume of the reduction buffer to 1 ml and washed twice with 10 ml ice cold reaction buffer (20 mM $NH_4HCO_3$, 5 mM EDTA, pH 8). The volume of the reduced phage was adjusted to 32 ml with reaction buffer and 8 ml of 50 M TBMB in ACN were added to obtain a final TBMB concentration of 10 μM. The reaction was incubated at 30° C. for 1 hr before non-reacted TBMB was removed by precipitation of the phage with ⅕ volume of 20% PEG, 2.5 M NaCl on ice and centrifugation at 4000 rpm for 30 minutes.

Phage Selections with Human Plasma Kallikrein and Cathepsin G

Biotinylated human plasma kallikrein and cathepsin G (5 to 20 μg; the protocol used for the biotinylation can be found below) were blocked by incubation in 0.5 ml washing buffer (10 mM Tris-Cl, pH 7.4, 150 mM NaCl, 10 mM $MgCl_2$, 1 mM $CaCl_2$) containing 1% BSA and 0.1% tween 20 for 30 minutes. The chemically modified phage (typically $10^{10}$-$10^{11}$ t.u. dissolved in 2 ml washing buffer) were blocked by addition of 1 ml of washing buffer containing 3% BSA and 0.3% tween 20 and incubation for 30 minutes. 3 ml blocked phage were pipetted to 0.5 ml blocked antigen and incubated for 30 minutes on a rotating wheel at RT. 50 μl magnetic steptavidin beads (Dynal, M-280 from Invitrogen, Paisley, UK) were blocked by incubation in 0.5 ml of washing buffer containing 1% BSA and 0.1% tween 20 for 30 minutes. The blocked beads were added to the phage/antigen mixture and incubated for 5 minutes at RT on a rotating wheel. The beads were washed 8 times with washing buffer containing 0.1% tween 20 and twice with washing buffer before incubation with 100 μl of 50 μM glycine, pH 2.2 for 5 minutes. Eluted phage were transferred to 50 μl of 1 M Tris-Cl, pH 8 for neutralization, incubated with 50 ml TG1 cells at $OD_{600}=0.4$ for 90 minutes at 37° C. and the cells were plated on large 2YT/chloramphenicol plates. Two additional rounds of panning were performed using the same procedures. In the second round of selection, neutravidin-coated magnetic beads were used to prevent the enrichment of streptavidin-specific peptides. The neutravidin beads were prepared by reacting 0.8 mg neutravidin (Pierce, Rockford, Ill., USA) with 0.5 ml tosyl-activated magnetic beads (Dynal, M-280 from Invitrogen, Paisley, UK) according to the supplier's instructions.

Screening Selected Clones for Inhibitory Activity

The genes that encode the peptides selected in the second and third round of biopanning were cloned into a pUC119 based vector for expression of the peptide-D1-D2 fusion proteins (disulfide-free D1-D2 protein; the cloning and expression procedures are described below). Oxidized sulfhydryl groups of the peptides were reduced by incubation of the protein (1-10 μM) with 1 mM TCEP in 20 mM $NH_4HCO_3$, pH 8 at 42° C. for 1 hr. The reducing agent was removed by size exclusion chromatography with a PD-10 column (Amersham Pharmacia, Uppsala, Sweden) using 20 mM $NH_4HCO_3$, 5 mM EDTA, pH 8 buffer. The thiol groups of the proteins were reacted by incubation with 10 μM TBMB in reaction buffer (20 mM $NH_4HCO_3$, 5 mM EDTA, pH 8, 20% ACN) at 30° C. for 1 hr. For removal of non-reacted TBMB and concentration the protein was filtered with a microcon YM-30 (Millipore, Bedford, Mass.). The concentrations of the products were determined by measuring the optical absorption at 280 nm. The $IC_{50}$ was measured by incubating various concentrations of the modified peptide fusion proteins (2-fold dilutions) with human plasma kallikrein (0.1 nM) or cathepsin G (20 nM) and determining the residual activity in 10 mM Tris-Cl, pH 7.4, 150 mM NaCl, 10 mM $MgCl_2$, 1 mM $CaCl_2$, 0.1% BSA, 0.01% triton-X100. Human plasma kallikrein activity was measured with the fluorogenic substrate Z-Phe-Arg-AMC (Bachem, Bubendorf, Switzerland) at a concentration of 100 µM on a Spectramax Gemini fluorescence plate reader (excitation at 355 nm, emission recording at 460 nm; Molecular Devices, Sunnyvale, Calif., USA). Human cathepsin G activity was measured with the colorimetric substrate N-Suc-Ala-Ala-Phe-Pro-pNA (Bachem, Bubendorf, Switzerland) at a concentration of 1 mM with a Spectramax absorption plate reader (recording at 410 nm; Molecular Devices, Sunnyvale, Calif., USA).

Chemical Synthesis of Bicyclic Peptides

Peptides with a free amine at the N-terminus and an amide at the C-terminus were chemically synthesized on a 25 mg scale by solid phase chemistry (JPT Peptide Technologies, Berlin, Germany). The crude peptides in 1 ml 70% $NH_4HCO_3$, pH 8 and 30% ACN (1 mM) were reacted with TBMB (1.2 mM) for 1 hr at RT. The reaction product was purified by reversed-phase high-performance liquid chromatography (HPLC) using a C18 column and gradient elution with a mobile phase composed of ACN and 0.1% aqueous trifluoroacetic acid (TFA) solution at a flow rate of 2 ml/min. The purified peptides were freeze-dried and dissolved in DMSO or a buffer of 50 mM Tris-Cl pH 7.8, 150 mM NaCl for activity measurements.

Cloning and Expression of Peptide-D12 Fusion Proteins

The domains D1-D2 of the g3p (comprising amino acid residues 2 to 217 of the mature fd-g3p) with and without the N-terminally fused peptide $^N$ACGSGCGSGCG$^C$ (SEQ ID No. 16) were expressed in *E. coli*. The pUC119 based expression vector with a leader sequence and the D1-D2 gene with a C-terminal hexa-histidine tag (here termed pUC119H6D12) was kindly provided by Phil Holliger from the Laboratory of Molecular Biology (LMB) in Cambridge. A plasmid for expression of D1-D2 with the N-terminal peptide was cloned by PCR amplification of the D1-D2 gene with the primers pepd12ba (encoding the peptide sequence) and d12fo and ligation into the SfiI/NotI digested pUC119H6D12 vector. The gene for the expression of disulfide-free D1-D2 with a total of 20 amino acids was PCR amplified from the vector fdg3p0ss21 with either the primer pair d120ssba/d120ssfo, pepd120ssba/d120ssfo, P2cd120ssba/d120ssfo or P1cd120ssba/d120ssfo and SfiI/NotI ligated into pUC119H6D12 for expression of disulfide-free D1-D2 with and without the N-terminal fused peptides $^N$ACGSGCGSGCG$^C$ (SEQ ID No. 16), $^N$AGSGCGSGCG$^C$ (SEQ ID No. 17) or $^N$AGSGKGSGCG$^C$ (SEQ ID No. 18). All 6 proteins were expressed in TG1 *E. coli* cells at 30° C. for 8 hours and the periplasmic fraction was purified step-wise by Ni-affinity chromatography and gel filtration on a Superdex 75 column in 20 mM $NH_4HCO_3$ pH 7.4.

Mass Spectrometric Analysis of Peptide-D12 Fusion Proteins

The molecular masses of the proteins (5-20 µM) before and after modification with TBMB were determined by denaturing the proteins in 4 volumes of 50% MeOH, 1% formic acid and analysis on a time of flight mass spectrometer with electrospray ionization (Micromass, Milford, Mass., USA). Molecular masses were obtained by deconvoluting multiply charged protein mass spectra using MassLynx version 4.1.

Creation of the Phage Peptide Library 1

The genes encoding a semi-random peptide with the sequence Ala-Cys-(Xaa)$_6$-Cys-(Xaa)$_6$-Cys (SEQ ID No. 19), the linker Gly-Gly-Ser-Gly (SEQ ID No. 20) and the two disulfide-free domains D1 and D2 were cloned in the correct orientation into the phage vector fd0D$_{12}$ to obtain phage library 1. The vector fd0D$_{12}$, lacking the genes of the D1 and D2 domains of gene 3 and having a second SfiI restriction site was previously created by whole-plasmid PCR amplification of fdg3p0ss21 using the primer ecoG3pNba and pelbsfiecofo. The genes encoding the peptide repertoire and the two gene 3 domains were step-wise created in two consecutive PCR reactions. First, the genes of D1 and D2 were PCR amplified with the two primer prepcr and sfi2fo using the vector fdg3p0ss21 as a template. Second, the DNA encoding the random peptides was appended in a PCR reaction using the primer sficx6ba and sfi2fo. The ligation of 33 and 9 µg of SfiI digested fd0D$_{12}$ plasmid and PCR product yielded $4.4 \times 10^9$ colonies on 12 20×20 cm chloramphenicol (30 µg/ml) 2YT plates. Colonies were scraped off the plates with 2YT media, supplemented with 15% glycerol and stored at −80° C. Glycerol stocks were diluted to OD$_{600}$=0.1 in 1 liter 2YT/chloramphenicol (30 µg/ml) cultures and phage were expressed at 30° C. over night (12 to 16 hrs).

Biotinylation of Antigens

Human plasma kallikrein (activated with factor XIIa) was purchased from Innovative Research (Southfiled, Mich., USA) and biotinylated at a concentration of 1.2 µM with a 5-fold molar excess of Sulfo-NHS-LC-biotin (Pierce, Rockford, Ill., USA) in PBS, pH 7.4/5% DMSO at RT for 1 hr. The biotinylated protein was purified on a PD-10 column using a buffer of 50 mM NaAc, pH 5.5, 200 mM NaCl. Readily biotinylated human cathepsin G was purchased from Lee Biosolutions (St. Louis, Mich., USA).

Subcloning and Expression Screening of Phage Selected Clones

The plasmid DNA of clones selected after the second and third round of biopanning was PCR-amplified in a single tube with the primer 21seqba and flagfo and cloned into the vector pUC119H6D12 at the SfiI and NotI sites for the periplasmic expression of the peptides fused to the disulfide-free D1 and D2 domains with a C-terminal FLAG tag and a hexa-histidine-tag. The ligated plasmids were electroporated into TG1 cells and plated on 2YT/ampicillin (100 µg/ml) plates. Clones expressing the recombinant protein were identified as follows: Media (2YT with 100 µg/ml ampicillin) in 96-deep well plates (1 ml/well) was inoculated with cells of individual colonies and incubated at 37° C. Protein expression was induced with 1 mM IPTG when the cultures were turbid and the plates were shaken 300 rpm at 30° C. o/n. The cells were pelleted by centrifugation at 3500 rpm for 30 minutes, lysed with washing buffer containing 1 mg/ml lysozyme and spun at 3500 rpm to pellet the cell debris. The supernatants were transferred to 96-well polysorp plates (Nunc, Roskilde, Denmark) for non-specific adsorption. The wells were rinsed twice with washing buffer containing 0.1% tween 20 and blocked with washing buffer containing 1% BSA and 0.1% tween 20 for 1 hr. Anti-FLAG M2-peroxidase conjugate (Sigma-Aldrich, St. Louis, Mo., USA) was 1:5000 diluted and blocked in washing buffer containing 1% BSA and 0.1% tween 20 and added to the plates for 1 hr. The wells were washed (5 times with washing buffer containing 0.1% tween 20 and once without detergent) and the bound peroxidase was detected with TMB substrate solution (eBiosciences, San Diego, USA). The plasmid DNA of protein expressing clones was sequenced (Geneservice, Cambridge, UK).

Affinity Maturation of Human Plasma Kallikrein Inhibitors

Three peptide phage libraries were created essentially as the library 1 (see above) but using the degenerate primer sficx6abc (library 2), sficx6abb (library 3) and sficx6aba (library 4) instead of sficx6ba. Electroporation of the ligation reactions into TG1 cells yielded 9.5×10⁸ (library 2), 1.1×10⁹ (library 3) and 1.2×10⁹ (library 4) transformants. Phage of each library were produced in 1 L cultures, purified, pooled and reacted with TBMB. Three rounds of panning were performed essentially as in the selections described in the materials and methods section but using the biotinylated human plasma kallikrein at a lower concentration (1 nM in the 1st and 2nd round, 200 µM in the 3rd round).

Activity and Specificity Measurement of Human Plasma Kallikrein Inhibitors

Inhibitory activities (IC$_{50}$) were determined by measuring residual activities of the enzyme upon incubation (30 min, RT) with different concentrations of inhibitor (typically ranging from 10 µM to 0.5 nM). The activities of human plasma kallikrein (0.1 nM) and factor XIa (0.8 nM; Innovative Research, Southfiled, Mich., USA) were measured with Z-Phe-Arg-AMC (100 µM) and the activity of human thrombin (2 nM; Innovative Research, Southfiled, Mich., USA) with Boc-Phe-Ser-Arg-AMC (100 µM) in 10 mM Tris-Cl, pH 7.4, 150 mM NaCl, 10 mM MgCl$_2$, 1 mM CaCl$_2$, 0.1% BSA, 0.01% triton X-100 and 5% DMSO. Recombinant mouse plasma kallikrein from R&D Systems (Minneapolis, Minn., USA) with a signal peptide was proteolytically activated with 0.5 mg/ml thermolysin at 37° C. for 1 hr. The activity of mouse plasma kallikrein (3 nM) was measured with Z-Phe-Arg (SEQ ID No. 36)-AMC (100 µM) in 50 mM Tris-Cl pH 7.5, 10 mM CaCl$_2$ and 250 mM NaCl, 0.1% BSA, 0.01% triton X-100 and 5% DMSO. Inhibitor hydrolysed in one binding loop was generated by incubation of TBMB modified peptide PK15 with human plasma kallikrein at a molar ratio of 5:1 for 24 hours at 37° C. and subsequent heat inactivation of the enzyme at 60° C. (30 min). Apparent K$_i$ values were calculated according to the Cheng and Prusoff equation.

Measurement of Factor XII Activation in Human Plasma

Normal human plasma from single donors was purchased from 3H Biomedical (Uppsala, Sweden). The plasma was centrifuged at 1500×g at 20° C. for 15 minutes to obtain platelet-poor plasma (PPP). Aliquots of the PPP were stored in polypropylene tubes at −80° C. Samples of 60 µl PPP containing 5, 50, 500 or 5000 nM of aprotinin (Roche, Mannheim, Germany) or TBMB modified peptide PK15 were prepared. Activation of factor XIIa was measured as follows. 2 µg of kaolin was added to the plasma samples, mixed well and incubated for 20 minutes at 37° C. The samples were diluted 250-fold in 50 mM Tris-Cl pH 7.8, 150 mM NaCl. Plasma kallikrein-like activity was measured with the chromogenic substrate H-D-Pro-Phe-Arg (SEQ ID No. 37)-pNA (100 µM; Bachem, Bubendorf, Switzerland) using an absorption plate reader (absorption at 450 nm; Molecular Devices, Sunnyvale, Calif., USA). The same chromogenic substrate is also recognized and modified by plasma kallikrein. However, at the inhibitor concentrations required to reduce the factor XIIa activity by 50% (160 nM for the TBMB modified peptide PK15 and 5 µM for aprotinin), the plasma kallikrein is essentially inhibited and can not be measured with the substrate.

Structure Determination of TBMB Modified Peptide PK15

1 mg of TBMB modified peptide PK15 was dissolved in 550 µl 10 mM deuterated Tris-Cl pH 6.6, 150 mM NaCl, 10 mM MgCl$_2$, 1 mM CaCl$_2$ to obtain an inhibitor concentration of 1 mM. Spectra of the inhibitor were recorded at 800 MHz (Bruker Avance with TCI cryoprobe). Spectral assignments were based on TOCSY and NOESY spectra. There were a total of 199 NOE restraints, 77 of which were inter-residue, and 122 intra-residue. The structure shown in FIG. 6 is the average structure of 50 calculated structure conformers. The program PyMOL was used for structure analysis and visualization of the molecular models.

REFERENCES FOR MATERIALS AND METHODS SECTION

1. Wu, P., Leinonen, J., Koivunen, E., Lankinen, H. & Stenman, U. H. Identification of novel prostate-specific antigen-binding peptides modulating its enzyme activity. *Eur J Biochem* 267, 6212-20 (2000).
2. Hekim, C. et al. Novel peptide inhibitors of human kallikrein 2. *J Biol Chem* 281, 12555-60 (2006).
3. Hansen, M. et al. A urokinase-type plasminogen activator-inhibiting cyclic peptide with an unusual P2 residue and an extended protease binding surface demonstrates new modalities for enzyme inhibition. *J Biol Chem* 280, 38424-37 (2005).
4. Andersen, L. M., Wind, T., Hansen, H. D. & Andreasen, P. A. A cyclic peptidylic inhibitor of murine urokinase-type plasminogen activator: changing species specificity by substitution of a single residue. *Biochem J* 412, 447-57 (2008).
5. Krook, M., Lindbladh, C., Eriksen, J. A. & Mosbach, K. Selection of a cyclic nonapeptide inhibitor to alpha-chymotrypsin using a phage display peptide library. *Mol Divers* 3, 149-59 (1997).
6. Dennis, M. S. et al. Peptide exosite inhibitors of factor VIIa as anticoagulants. *Nature* 404, 465-70 (2000).
7. Huang, L. et al. Novel peptide inhibitors of angiotensin-converting enzyme 2. *J Biol Chem* 278, 15532-40 (2003).
8. Karasseva, N. G., Glinsky, V. V., Chen, N. X., Komatireddy, R. & Quinn, T. P. Identification and characterization of peptides that bind human ErbB-2 selected from a bacteriophage display library. *J Protein Chem* 21, 287-96 (2002).
9. Houimel, M., Mach, J. P., Corthesy-Theulaz, I., Corthesy, B. & Fisch, I. New inhibitors of *Helicobacter pylori* urease holoenzyme selected from phage-displayed peptide libraries. *Eur J Biochem* 262, 774-80 (1999).
10. Lunder, M., Bratkovic, T., Kreft, S. & Strukelj, B. Peptide inhibitor of pancreatic lipase selected by phage display using different elution strategies. *J Lipid Res* 46, 1512-6 (2005).
11. Sanschagrin, F. & Levesque, R. C. A specific peptide inhibitor of the class B metallo-beta-lactamase L-1 from *Stenotrophomonas maltophilia* identified using phage display. *J Antimicrob Chemother* 55, 252-5 (2005).
12. Sperinde, J. J., Choi, S. J. & Szoka, F. C., Jr. Phage display selection of a peptide DNase II inhibitor that enhances gene delivery. *J Gene Med* 3, 101-8 (2001).

REFERENCES TO EXAMPLE 8

1. Hüser, J. *High-Throughput Screening in Drug Discovery* (eds. Mannhold, R., Kubinyi, H. & Folkers, G.) (Wiley-VCH, Weinheim, 2006).
2. Bleicher, K. H., Bohm, H. J., Muller, K. & Alanine, A. I. Hit and lead generation: beyond high-throughput screening. *Nat Rev Drug Discov* 2, 369-78 (2003).
3. Marks, J. D., Hoogenboom, H. R., Griffiths, A. D. & Winter, G. Molecular evolution of proteins on filamentous phage. Mimicking the strategy of the immune system. *J Biol Chem* 267, 16007-10 (1992).
4. Jespers, L. S., Roberts, A., Mahler, S. M., Winter, G. & Hoogenboom, H. R. Guiding the selection of human antibodies from phage display repertoires to a single epitope of an antigen. *Biotechnology* (N Y) 12, 899-903 (1994).
5. Hudson, P. J. & Souriau, C. Engineered antibodies. *Nat Med* 9, 129-34 (2003).
6. Doyon, J. B., Snyder, T. M. & Liu, D. R. Highly sensitive in vitro selections for DNA-linked synthetic small molecules with protein binding affinity and specificity. *J Am Chem Soc* 125, 12372-3 (2003).
7. Woiwode, T. F. et al. Synthetic compound libraries displayed on the surface of encoded bacteriophage. *Chem Biol* 10, 847-58 (2003).
8. Brenner, S. & Lerner, R. A. Encoded combinatorial chemistry. *Proc Natl Acad Sci USA* 89, 5381-3 (1992).
9. Halpin, D. R. & Harbury, P. B. DNA display II. Genetic manipulation of combinatorial chemistry libraries for small-molecule evolution. *PLoS Biol* 2, E174 (2004).
10. Jespers, L., Bonnert, T. P. & Winter, G. Selection of optical biosensors from chemisynthetic antibody libraries. *Protein Eng Des Sel* 17, 709-13 (2004).
11. Jespers, L. S. A., Winter, G. P., Bonnert, T. P. & Simon, T. M. (PCT/GB94/01422).
12. Timmerman, P., Beld, J., Puijk, W. C. & Meloen, R. H. Rapid and quantitative cyclization of multiple peptide loops onto synthetic scaffolds for structural mimicry of protein surfaces. *Chembiochem* 6, 821-4 (2005).
13. Driggers, E. M., Hale, S. P., Lee, J. & Terrett, N. K. The exploration of macrocycles for drug discovery—an underexploited structural class. *Nat Rev Drug Discov* 7, 608-24 (2008).
14. Wessjohann, L. A., Ruijter, E., Garcia-Rivera, D. & Brandt, W. What can a chemist learn from nature's macrocycles?—a brief, conceptual view. *Mol Divers* 9, 171-86 (2005).
15. Kemp, D. S. & McNamara, P. E. Conformationally restricted cyclic nonapeptides derived from L-cysteine and LL-3-amino-2-piperidino-6-carboxylic acid (LL-acp), a potent b-turn-inducing dipeptide analogue. *Journal of Organic Chemistry* 50, 5834-5838 (1985).
16. Kather, I., Bippes, C. A. & Schmid, F. X. A stable disulfide-free gene-3-protein of phage fd generated by in vitro evolution. *J Mol Biol* 354, 666-78 (2005).
17. Cheng, Y. & Prusoff, W. H. Relationship between the inhibition constant (K1) and the concentration of inhibitor which causes 50 percent inhibition (150) of an enzymatic reaction. *Biochem Pharmacol* 22, 3099-108 (1973).
18. Cremlyn, R. J. *An introduction to organosulfur chemistry* (Wiley, 1996).
19. Huang, L. et al. Novel peptide inhibitors of angiotensin-converting enzyme 2. *J Biol Chem* 278, 15532-40 (2003).
20. Dennis, M. S. et al. Peptide exosite inhibitors of factor VIIa as anticoagulants. *Nature* 404, 465-70 (2000).
21. Jackson, D. Y. et al. A designed peptide ligase for total synthesis of ribonuclease A with unnatural catalytic residues. *Science* 266, 243-7 (1994).
22. Abbenante, G. & Fairlie, D. P. Protease inhibitors in the clinic. *Med Chem* 1, 71-104 (2005).
23. Turk, B. Targeting proteases: successes, failures and future prospects. *Nat Rev Drug Discov* 5, 785-99 (2006).
24. Melkko, S., Scheuermann, J., Dumelin, C. E. & Neri, D. Encoded self-assembling chemical libraries. *Nat Biotechnol* 22, 568-74 (2004).
25. Li, S. & Roberts, R. W. A novel strategy for in vitro selection of peptide-drug conjugates. *Chem Biol* 10, 233-9 (2003).
26. Millward, S. W., Takahashi, T. T. & Roberts, R. W. A general route for post-translational cyclization of mRNA display libraries. *J Am Chem Soc* 127, 14142-3 (2005).
27. Millward, S. W., Fiacco, S., Austin, R. J. & Roberts, R. W. Design of cyclic peptides that bind protein surfaces with antibody-like affinity. *ACS Chem Biol* 2, 625-34 (2007).

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A method for making a complex, said method comprising
   (a) displaying one or more polypeptides in a phage display system, wherein the polypeptide comprises the sequence (X)lC(X)mC(X)nC(X)o (SEQ ID NO. 67), wherein C represents the amino acid cysteine, X represents a random amino acid, m and n are numbers between 1 and 20 defining the length of intervening polypeptide segments and l and o are numbers between 0 and 20 defining the length of the flanking polypeptide segments;
   (b) reducing the cysteine amino acids of the displayed polypeptides;
   (c) the polypeptide comprising reduced cysteine amino acids is purified by filtration;
   (d) providing tris-(bromomethyl)benzene (TBMB); and
   (e) attaching TBMB to said reduced and purified polypeptide by formation of three discrete covalent bonds between said TBMB and said polypeptide via said cysteine amino acid residues, and form at least one loop which comprises a sequence of two or more amino acids subtended between two of said cysteine amino acid residues, thus forming the complex.

2. A method according to claim 1, wherein following the filtration purification step (c), the polypeptide is maintained in the reduced state for bonding to the connector compound by incubation in degassed buffer and in the presence of chelating agent.

3. A method according to claim 1, wherein step (e) comprises incubation of the polypeptide and connector compound together at 30° C. and at pH 8 in aqueous buffer comprising acetonitrile.

4. A method according to claim 1, said method comprising the further step of (f) cleaving one or more bonds of the polypeptide chain.

5. A method according to claim 4 wherein said cleavage step comprises contacting said polypeptide with a protease.

6. A method for identifying a complex according to claim 1 which is capable of binding to a ligand, the method comprising: (a) providing a complex according to claim 1 (b) contacting said complex with the ligand, and (c) selecting those complexes which bind said ligand.

7. A method for identifying a complex according to claim 1, wherein the the polypeptide comprises a sequence SEQ ID No. 1-5, 9, 10, or 36-63.

* * * * *

SEQUENCE LISTING

```
<160> NUMBER OF SEQ ID NOS: 67

<210> SEQ ID NO 1
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 1

Ala Cys Ser Asp Arg Phe Arg Asn Cys Pro Leu Trp Ser Gly Thr Cys
1               5                   10                  15

Gly

<210> SEQ ID NO 2
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 2
```

```
Ala Cys Ser Thr Glu Arg Arg Tyr Cys Pro Ile Glu Ile Phe Pro Cys
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 3

Ala Cys Gly Thr Gly Glu Gly Arg Cys Arg Val Asn Trp Thr Pro Cys
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 4

Ala Cys Ser Asp Arg Phe Arg Asn Cys Pro Ala Asp Glu Ala Leu Cys
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: XAA
<222> LOCATION: (3)..(8)
<223> OTHER INFORMATION: XAA = ANY AMINO ACID
<220> FEATURE:
<221> NAME/KEY: XAA
<222> LOCATION: (10)..(15)
<223> OTHER INFORMATION: XAA = ANY AMINO ACID

<400> SEQUENCE: 5

Ala Cys Xaa Xaa Xaa Xaa Xaa Xaa Cys Xaa Xaa Xaa Xaa Xaa Xaa Cys
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 6

Gly Cys Ser Asp Arg Phe Arg Asn Cys Pro Ala Asp Glu Ala Leu Cys
1               5                   10                  15

Gly

<210> SEQ ID NO 7
<211> LENGTH: 17
<212> TYPE: PRT
<213> ORGANISM: Artificial Sequence
```

```
<220> FEATURE:
<223> OTHER INFORMATION: SYNTHETIC PEPTIDE

<400> SEQUENCE: 7

Ala Cys Glu Tyr Gly Asp Leu Trp Cys Gly Trp Asp Pro Pro Val Cys
1               5                   10                  15
Gly

<210> SEQ ID NO 8
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 8

Ala Cys Ile Phe Asp Leu Gly Phe Cys His Asn Asp Trp Trp Asn Cys
1               5                   10                  15
Gly

<210> SEQ ID NO 9
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 9

Ala Cys Leu Arg Ala Gln Glu Asp Cys Val Tyr Asp Arg Gly Phe Cys
1               5                   10                  15
Gly

<210> SEQ ID NO 10
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 10

Ala Cys Asn Ser Arg Phe Ser Gly Cys Gln Ile Asp Leu Leu Met Cys
1               5                   10                  15
Gly

<210> SEQ ID NO 11
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 11

Ala Cys Ser Arg Tyr Glu Val Asp Cys Arg Gly Arg Gly Ser Ala Cys
1               5                   10                  15
Gly

<210> SEQ ID NO 12
<211> LENGTH: 220
<212> TYPE: PRT
<213> ORGANISM: Artificial Sequence
<220> FEATURE:
<223> OTHER INFORMATION: SYNTHETIC PEPTIDE

<400> SEQUENCE: 12
```

Ala Glu Thr Val Glu Ser Cys Leu Ala Lys Pro His Thr Glu Asn Ser
1               5                   10                  15

Phe Thr Asn Val Trp Lys Asp Asp Lys Thr Leu Asp Arg Tyr Ala Asn
            20                  25                  30

Tyr Glu Gly Cys Leu Trp Asn Ala Thr Gly Val Val Cys Thr Gly
        35                  40                  45

Asp Glu Thr Gln Cys Tyr Gly Thr Trp Val Pro Ile Gly Leu Ala Ile
    50                  55                  60

Pro Glu Asn Glu Gly Gly Ser Glu Gly Gly Ser Glu Gly Gly
65                  70                  75                  80

Gly Ser Glu Gly Gly Thr Lys Pro Pro Glu Tyr Gly Asp Thr Pro
            85                  90                  95

Ile Pro Gly Tyr Thr Tyr Ile Asn Pro Leu Asp Gly Thr Tyr Pro Pro
            100                 105                 110

Gly Thr Glu Gln Asn Pro Ala Asn Pro Asn Pro Ser Leu Glu Glu Ser
            115                 120                 125

Gln Pro Leu Asn Thr Phe Met Phe Gln Asn Asn Arg Phe Arg Asn Arg
    130                 135                 140

Gln Gly Ala Leu Thr Val Tyr Thr Gly Thr Val Thr Gln Gly Thr Asp
145                 150                 155                 160

Pro Val Lys Thr Tyr Tyr Gln Tyr Thr Pro Val Ser Ser Lys Ala Met
            165                 170                 175

Tyr Asp Ala Tyr Trp Asn Gly Lys Phe Arg Asp Cys Ala Phe His Ser
            180                 185                 190

Gly Phe Asn Glu Asp Pro Phe Val Cys Glu Tyr Gln Gly Gln Ser Ser
            195                 200                 205

Asp Leu Pro Gln Pro Pro Val Asn Ala Pro Ser Gly
    210                 215                 220

<210> SEQ ID NO 13
<211> LENGTH: 220
<212> TYPE: PRT
<213> ORGANISM: Artificial Sequence
<220> FEATURE:
<223> OTHER INFORMATION: SYNTHETIC PEPTIDE

<400> SEQUENCE: 13

Ala Glu Thr Val Glu Ser Ser Leu Ala Lys Ser His Ile Glu Gly Ser
1               5                   10                  15

Phe Thr Asn Val Trp Lys Asp Asp Lys Thr Leu Asp Trp Tyr Ala Asn
            20                  25                  30

Tyr Glu Gly Ile Leu Trp Lys Ala Thr Gly Val Val Ile Thr Gly
        35                  40                  45

Asp Glu Thr Gln Val Tyr Ala Thr Trp Val Pro Ile Gly Leu Ala Ile
    50                  55                  60

Pro Glu Asn Glu Gly Gly Ser Glu Gly Gly Ser Glu Gly Gly
65                  70                  75                  80

Gly Ser Glu Gly Gly Thr Lys Pro Pro Glu Tyr Gly Asp Thr Pro
            85                  90                  95

Ile Pro Gly Tyr Ile Tyr Ile Asn Pro Leu Asp Gly Thr Tyr Pro Pro
            100                 105                 110

Gly Thr Glu Gln Asn Pro Ala Asn Pro Asn Pro Ser Leu Glu Glu Ser
            115                 120                 125

His Pro Leu Asn Thr Phe Met Phe Gln Asn Asn Arg Phe Arg Asn Arg
    130                 135                 140

```
Gln Gly Ala Leu Thr Val Tyr Thr Gly Thr Val Gln Gly Thr Asp
145                 150                 155                 160

Pro Val Lys Thr Tyr Tyr Gln Tyr Thr Pro Val Ser Ser Lys Ala Met
            165                 170                 175

Tyr Asp Ala Tyr Trp Asn Gly Lys Phe Arg Asp Val Ala Phe His Ser
            180                 185                 190

Gly Phe Asn Glu Asp Leu Leu Val Ala Glu Tyr Gln Gly Gln Ser Ser
        195                 200                 205

Tyr Leu Pro Gln Pro Pro Val Asn Ala Pro Ser Gly
    210                 215                 220

<210> SEQ ID NO 14
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 14

Gly Cys Gly Ser Gly Cys Gly Ser Gly Cys Gly
1               5                   10

<210> SEQ ID NO 15
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 15

Ala Cys Gly Ser Gly Cys Gly Ser Gly Cys Gly
1               5                   10

<210> SEQ ID NO 16
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 16

Ala Gly Ser Gly Cys Gly Ser Gly Cys Gly
1               5                   10

<210> SEQ ID NO 17
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 17

Ala Gly Ser Gly Lys Gly Ser Gly Cys Gly
1               5                   10

<210> SEQ ID NO 18
<211> LENGTH: 16
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: XAA
<222> LOCATION: (3)..(8)
<223> OTHER INFORMATION: XAA = ANY AMINO ACID
```

```
<220> FEATURE:
<221> NAME/KEY: XAA
<222> LOCATION: (10)..(15)
<223> OTHER INFORMATION: XAA = ANY AMINO ACID

<400> SEQUENCE: 18

Ala Cys Xaa Xaa Xaa Xaa Xaa Xaa Cys Xaa Xaa Xaa Xaa Xaa Xaa Cys
1               5                   10                  15

<210> SEQ ID NO 19
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 19

Gly Gly Ser Gly
1

<210> SEQ ID NO 20
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 20

Ala Ala Phe Pro
1

<210> SEQ ID NO 21
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 21

Gly Gly Ala Ala
1

<210> SEQ ID NO 22
<211> LENGTH: 15
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: XAA
<222> LOCATION: (2)..(7)
<223> OTHER INFORMATION: XAA = ANY AMINO ACID
<220> FEATURE:
<221> NAME/KEY: XAA
<222> LOCATION: (8)..(14)
<223> OTHER INFORMATION: XAA = ANY AMINO ACID

<400> SEQUENCE: 22

Cys Xaa Xaa Xaa Xaa Xaa Xaa Cys Xaa Xaa Xaa Xaa Xaa Xaa Cys
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: SYNTHETIC PEPTIDE

<400> SEQUENCE: 23
```

```
Cys Val Ala Tyr Cys Ile Glu His His Cys Trp Thr
1               5                   10
```

<210> SEQ ID NO 24
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 24

```
Ser Arg Phe Lys Val Trp Trp Ala Ala Phe
1               5                   10
```

<210> SEQ ID NO 25
<211> LENGTH: 12
<212> TYPE: PRT
<213> ORGANISM: Artificial Sequence
<220> FEATURE:
<223> OTHER INFORMATION: SYNTHETIC PEPTIDE

<400> SEQUENCE: 25

```
Cys Ser Trp Arg Gly Leu Glu Asn His Arg Met Cys
1               5                   10
```

<210> SEQ ID NO 26
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 26

```
Cys Pro Ala Tyr Ser Arg Tyr Leu Asp Cys
1               5                   10
```

<210> SEQ ID NO 27
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 27

```
Cys Cys Phe Ser Trp Arg Cys Arg Cys
1               5
```

<210> SEQ ID NO 28
<211> LENGTH: 15
<212> TYPE: PRT
<213> ORGANISM: Artificial Sequence
<220> FEATURE:
<223> OTHER INFORMATION: SYNTHETIC PEPTIDE

<400> SEQUENCE: 28

```
Glu Glu Trp Glu Val Leu Cys Trp Thr Trp Glu Thr Cys Glu Arg
1               5                   10                  15
```

<210> SEQ ID NO 29
<211> LENGTH: 22
<212> TYPE: PRT
<213> ORGANISM: Artificial Sequence
<220> FEATURE:
<223> OTHER INFORMATION: SYNTHETIC PEPTIDE

<400> SEQUENCE: 29

```
Gly Asp Tyr Ser His Cys Ser Pro Leu Arg Tyr Tyr Pro Trp Trp Lys
1               5                   10                  15

Cys Thr Tyr Pro Asp Pro
            20
```

<210> SEQ ID NO 30
<211> LENGTH: 6
<212> TYPE: PRT
<213> ORGANISM: Artificial Sequence
<220> FEATURE:
<223> OTHER INFORMATION: SYNTHETIC PEPTIDE

<400> SEQUENCE: 30

```
Lys Cys Cys Tyr Ser Leu
1               5
```

<210> SEQ ID NO 31
<211> LENGTH: 6
<212> TYPE: PRT
<213> ORGANISM: Artificial Sequence
<220> FEATURE:
<223> OTHER INFORMATION: SYNTHETIC PEPTIDE

<400> SEQUENCE: 31

```
Tyr Asp Phe Tyr Trp Trp
1               5
```

<210> SEQ ID NO 32
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 32

```
Cys Gln Pro His Pro Gly Gln Thr Cys
1               5
```

<210> SEQ ID NO 33
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 33

```
Cys Val His Ser Pro Asn Arg Glu Cys
1               5
```

<210> SEQ ID NO 34
<211> LENGTH: 12
<212> TYPE: PRT
<213> ORGANISM: Artificial Sequence
<220> FEATURE:
<223> OTHER INFORMATION: SYNTHETIC PEPTIDE

<400> SEQUENCE: 34

```
Cys Leu Arg Leu Leu Gln Trp Phe Leu Trp Ala Cys
1               5                   10
```

<210> SEQ ID NO 35
<211> LENGTH: 12
<212> TYPE: PRT
<213> ORGANISM: Artificial Sequence
<220> FEATURE:
<223> OTHER INFORMATION: SYNTHETIC PEPTIDE

```
<400> SEQUENCE: 35

Cys Leu Arg Leu Leu Gln Trp Phe Leu Trp Ala Cys
1               5                   10

<210> SEQ ID NO 36
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 36

Ala Cys Asp Ser Arg Phe Arg Asn Cys Pro Trp Ser Met Ser Gly Cys
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 37

Ala Cys Arg Asp Ile Arg Phe Arg Cys Asn Tyr Asp Val Ala Val Cys
1               5                   10                  15

Gly

<210> SEQ ID NO 38
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 38

Ala Cys Ala Pro Trp Arg Thr Met Cys Leu Asn Ile Asp Gly Pro Cys
1               5                   10                  15

Gly

<210> SEQ ID NO 39
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 39

Ala Cys Pro Val Trp Arg Thr Leu Cys Met Glu Ser Glu Gly Val Cys
1               5                   10                  15

Gly

<210> SEQ ID NO 40
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 40

Ala Cys Phe Pro Leu Trp Arg Thr Cys Val His Glu Pro Thr Met Cys
1               5                   10                  15

Cys
```

<210> SEQ ID NO 41
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 41

Ala Cys Trp Gln Val Gln Val Asn Cys Arg Val Asn Phe Gly Lys Cys
1               5                   10                  15

Gly

<210> SEQ ID NO 42
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 42

Ala Cys Gly Gly Asn Ser Asp Arg Cys Arg Val Asn Asn Ile Ser Cys
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 43

Ala Cys Gly Arg Gly Asp Gln Thr Cys Arg Val Asn Trp His Pro Cys
1               5                   10                  15

Gly

<210> SEQ ID NO 44
<211> LENGTH: 15
<212> TYPE: PRT
<213> ORGANISM: Artificial Sequence
<220> FEATURE:
<223> OTHER INFORMATION: SYNTHETIC PEPTIDE

<400> SEQUENCE: 44

Ala Cys Val His Asn Tyr Cys Arg Val Asn Trp Thr Pro Cys Gly
1               5                   10                  15

<210> SEQ ID NO 45
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 45

Ala Cys Glu Tyr Gly Asp Leu Trp Cys Gly Trp Asp Pro Pro Val Cys
1               5                   10                  15

Gly

<210> SEQ ID NO 46
<211> LENGTH: 17
<212> TYPE: PRT
<213> ORGANISM: Artificial Sequence

```
<220> FEATURE:
<223> OTHER INFORMATION: SYNTHETIC PEPTIDE

<400> SEQUENCE: 46

Ala Cys Glu Tyr Asp Val Gly Phe Cys Trp Asp Gly Gly Phe Gln Cys
1               5                   10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 47

Ala Cys Leu Phe Asp Ala Gly Phe Cys Gln Gln His Ser Thr Glu Cys
1               5                   10                  15

Gly

<210> SEQ ID NO 48
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 48

Ala Cys Leu Phe Asp Leu Gly Phe Cys Gly Gly Gly Glu Gly Pro Cys
1               5                   10                  15

Gly

<210> SEQ ID NO 49
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 49

Ala Cys Pro Arg Ile Glu Gly Phe Cys Leu Pro Ile Phe Ser Asp Cys
1               5                   10                  15

Gly

<210> SEQ ID NO 50
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 50

Ala Cys Thr Arg Gly Ser Gly Asp Cys Thr Tyr Asp Phe Gly Phe Cys
1               5                   10                  15

Gly

<210> SEQ ID NO 51
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 51
```

Ala Cys Ser Asp Arg Phe Arg Asn Cys Pro Ala Asp Glu Arg Glu Cys
1               5                   10                  15

Gly

<210> SEQ ID NO 52
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 52

Ala Cys Ser Asp Arg Phe Arg Asn Cys Pro Val Asp Glu Ala Leu Cys
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 53

Ala Cys Ser Asp Arg Phe Arg Asn Cys Pro Val Asp Glu Trp Leu Cys
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 54

Ala Cys Ser Asp Arg Phe Arg Asn Cys Pro Gly Asp Glu Ser Leu Cys
1               5                   10                  15

Gly

<210> SEQ ID NO 55
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 55

Ala Cys Ser Asp Arg Phe Arg Asn Cys Pro Tyr Thr Leu His Asp Cys
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 56

Ala Cys Ser Asp Arg Phe Arg Asn Cys Pro Tyr Val Ser Ser Asp Cys
1               5                   10                  15

Gly

<210> SEQ ID NO 57
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 57

Ala Cys Ser Asp Arg Phe Arg Asn Cys Pro Tyr Ser Glu Gly Asp Cys
1               5                   10                  15

Gly

<210> SEQ ID NO 58
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 58

Ala Cys Ser Asp Arg Phe Arg Asn Cys Pro Val Trp Asp Ser Ser Cys
1               5                   10                  15

Gly

<210> SEQ ID NO 59
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 59

Ala Cys Ser Asp Arg Phe Arg Asn Cys Pro Val Ser Glu Ser Ala Cys
1               5                   10                  15

Gly

<210> SEQ ID NO 60
<211> LENGTH: 26
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: XAA
<222> LOCATION: (7)..(12)
<223> OTHER INFORMATION: XAA = ANY AMINO ACID
<220> FEATURE:
<221> NAME/KEY: XAA
<222> LOCATION: (14)..(19)
<223> OTHER INFORMATION: XAA = ANY AMINO ACID

<400> SEQUENCE: 60

Pro Ala Met Ala Ala Cys Xaa Xaa Xaa Xaa Xaa Xaa Cys Xaa Xaa Xaa
1               5                   10                  15

Xaa Xaa Xaa Cys Gly Gly Ser Gly Ala Glu
            20                  25

<210> SEQ ID NO 61
<211> LENGTH: 26
<212> TYPE: PRT
<213> ORGANISM: Artificial Sequence
<220> FEATURE:
<223> OTHER INFORMATION: SYNTHETIC PEPTIDE
<220> FEATURE:

```
<221> NAME/KEY: XAA
<222> LOCATION: (14)..(19)
<223> OTHER INFORMATION: XAA = ANY AMINO ACID

<400> SEQUENCE: 61

Pro Ala Met Ala Ala Cys Ser Asp Arg Phe Arg Asn Cys Xaa Xaa Xaa
1               5                   10                  15

Xaa Xaa Xaa Cys Gly Gly Ser Gly Ala Glu
            20                  25

<210> SEQ ID NO 62
<211> LENGTH: 26
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: XAA
<222> LOCATION: (14)..(19)
<223> OTHER INFORMATION: XAA = ANY AMINO ACID

<400> SEQUENCE: 62

Pro Ala Met Ala Ala Cys Ala Pro Trp Arg Thr Ala Cys Xaa Xaa Xaa
1               5                   10                  15

Xaa Xaa Xaa Cys Gly Gly Ser Gly Ala Glu
            20                  25

<210> SEQ ID NO 63
<211> LENGTH: 26
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: XAA
<222> LOCATION: (7)..(12)
<223> OTHER INFORMATION: XAA = ANY AMINO ACID

<400> SEQUENCE: 63

Pro Ala Met Ala Ala Cys Xaa Xaa Xaa Xaa Xaa Xaa Cys Arg Val Asn
1               5                   10                  15

Trp Thr Pro Cys Gly Gly Ser Gly Ala Glu
            20                  25

<210> SEQ ID NO 64
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 64

Gly Cys Gly Ser Gly Cys Gly Ser Gly Cys Ala
1               5                   10

<210> SEQ ID NO 65
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 65

Gly Cys Gly Ser Gly Cys Gly Ser Gly Ala
1               5                   10
```

```
<210> SEQ ID NO 66
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 66

Gly Cys Gly Ser Gly Lys Gly Ser Gly Ala
1               5                   10

<210> SEQ ID NO 67
<211> LENGTH: 85
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: XAA
<222> LOCATION: (1)..(20)
<223> OTHER INFORMATION: XAA = 20 OF ANY AMINO ACID OR LESS THAN TWENTY,
      INCLUDING 0-20
<220> FEATURE:
<221> NAME/KEY: XAA
<222> LOCATION: (22)..(41)
<223> OTHER INFORMATION: XAA = 20 OF ANY AMINO ACID OR LESS THAN TWENTY,
      INCLUDING 1-20
<220> FEATURE:
<221> NAME/KEY: XAA
<222> LOCATION: (43)..(62)
<223> OTHER INFORMATION: XAA = 20 OF ANY AMINO ACID OR LESS THAN TWENTY,
      INCLUDING 1-20
<220> FEATURE:
<221> NAME/KEY: XAA
<222> LOCATION: (64)..(85)
<223> OTHER INFORMATION: XAA = 20 OF ANY AMINO ACID OR LESS THAN TWENTY,
      INCLUDING 0-20

<400> SEQUENCE: 67

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Xaa Xaa Xaa Xaa Xaa Xaa Xaa Xaa Xaa
            20                  25                  30

Xaa Xaa Xaa Xaa Xaa Xaa Xaa Xaa Xaa Cys Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Cys Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa
                85
```